(12) United States Patent
Tateno et al.

(10) Patent No.: US 12,227,509 B2
(45) Date of Patent: Feb. 18, 2025

(54) DIHYDROPYRAZOLOPYRAZINONE DERIVATIVE HAVING MGAT2 INHIBITORY ACTIVITY

(71) Applicant: Shionogi & Co., Ltd., Osaka (JP)

(72) Inventors: Yusuke Tateno, Osaka (JP); Manabu Katou, Toyonaka (JP); Toshihiro Wada, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 821 days.

(21) Appl. No.: 17/422,108

(22) PCT Filed: Jan. 10, 2020

(86) PCT No.: PCT/JP2020/000553
§ 371 (c)(1),
(2) Date: Jul. 9, 2021

(87) PCT Pub. No.: WO2020/145369
PCT Pub. Date: Jul. 16, 2020

(65) Prior Publication Data
US 2022/0135577 A1 May 5, 2022

(30) Foreign Application Priority Data
Jan. 11, 2019 (JP) .................................. 2019-003073

(51) Int. Cl.
*C07D 487/10* (2006.01)
*A61P 3/04* (2006.01)
*C07D 491/20* (2006.01)

(52) U.S. Cl.
CPC .............. *C07D 487/10* (2013.01); *A61P 3/04* (2018.01); *C07D 491/20* (2013.01)

(58) Field of Classification Search
CPC ........ C07D 487/10; C07D 491/20; A61P 3/04
See application file for complete search history.

(56) References Cited

U.S. PATENT DOCUMENTS

2015/0368242 A1 12/2015 Suzuki et al.
2018/0370945 A1* 12/2018 Ahmad ................... A61P 43/00

FOREIGN PATENT DOCUMENTS

CN 103012397 3/2017
CN 104109160 12/2017
(Continued)

OTHER PUBLICATIONS

Google Patents_WO 2017/069224 A1—English Machine Translation (Year: 2017).*

(Continued)

*Primary Examiner* — Clinton A Brooks
*Assistant Examiner* — Josmalen M. Ramos-Lewis
(74) *Attorney, Agent, or Firm* — Wenderoth, Lind & Ponack, L.L.P.

(57) ABSTRACT

The present invention provides a compound represented by a following formula.

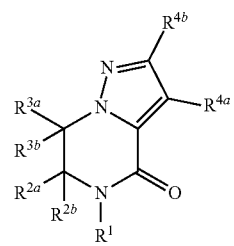

A compound represented by, wherein
$R^1$ is hydrogen, hydroxy, or the like;
$R^{2a}$ and $R^{2b}$ may be taken together with an adjacent carbon atom to form ring B,
ring B is a substituted or unsubstituted non-aromatic carbocycle or a substituted or unsubstituted non-aromatic heterocycle;
$R^{3a}$ is hydrogen, halogen, hydroxy, or the like;
$R^{3b}$ is hydrogen, halogen, hydroxy, or the like;
$R^{4a}$ is a group represented by formula:

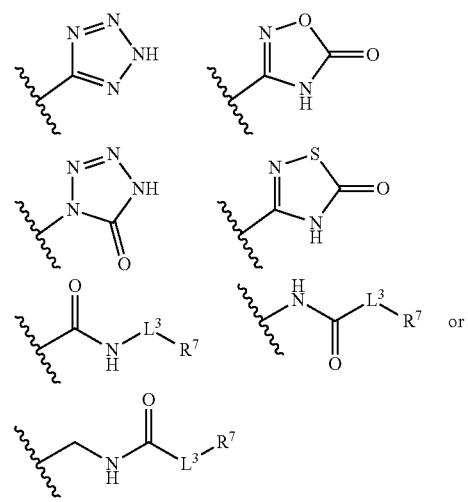

$L^3$ is a single bond or substituted or unsubstituted alkylene,
$R^7$ is hydrogen, halogen, hydroxy, or the like, and
$R^{4b}$ is halogen, cyano, carboxy, or the like, or its pharmaceutically acceptable salt.

28 Claims, No Drawings

(56) References Cited

FOREIGN PATENT DOCUMENTS

| | | |
|---|---|---|
| EP | 2 078 719 | 7/2009 |
| EP | 3 112 369 | 1/2017 |
| EP | 3 653 625 | 5/2020 |
| JP | 2013-67595 | 4/2013 |
| JP | 2014-5245 | 1/2014 |
| JP | 2014-9165 | 1/2014 |
| JP | 2016-164154 | 9/2016 |
| KR | 10-2010-0097077 | 9/2010 |
| WO | 2004/058176 | 7/2004 |
| WO | 2004/058762 | 7/2004 |
| WO | 2007/117180 | 10/2007 |
| WO | 2008/085509 | 7/2008 |
| WO | 2009/126584 | 10/2009 |
| WO | 2010/095767 | 8/2010 |
| WO | 2011/079051 | 6/2011 |
| WO | 2012/091010 | 7/2012 |
| WO | 2012/117027 | 9/2012 |
| WO | 2013/045400 | 4/2013 |
| WO | 2013/082345 | 6/2013 |
| WO | 2013/130660 | 9/2013 |
| WO | 2013/175417 | 11/2013 |
| WO | 2014/054053 | 4/2014 |
| WO | 2014/074365 | 5/2014 |
| WO | 2014/154586 | 10/2014 |
| WO | 2014/193884 | 12/2014 |
| WO | 2015/073763 | 5/2015 |
| WO | 2015/073767 | 5/2015 |
| WO | 2015/112754 | 7/2015 |
| WO | 2015/129845 | 9/2015 |
| WO | 2015/134699 | 9/2015 |
| WO | 2015/134701 | 9/2015 |
| WO | 2015/144799 | 10/2015 |
| WO | 2015/191681 | 12/2015 |
| WO | 2016/024598 | 2/2016 |
| WO | 2016/090382 | 6/2016 |
| WO | 2016/106009 | 6/2016 |
| WO | 2016/121782 | 8/2016 |
| WO | 2017/069224 | 4/2017 |
| WO | WO-2017069224 A1 * | 4/2017 |

OTHER PUBLICATIONS

WO 2017/069224 A1—English Machine Translation (Year: 2017).*
International Search Report issued Mar. 17, 2020 in International (PCT) Application No. PCT/JP2020/000553.
Cao et al., "A Predominant Role of Acyl-CoA: monoacylglycerol Acyltransferase-2 in Dietary Fat Absorption Implicated by Tissue Distribution, Subcellular Localization, and Up-regulation by High Fat Diet", The Journal of Biological Chemistry, vol. 279, No. 18, Issue of Apr. 30, 2004, pp. 18878-18886.
Yen et al., "Deficiency of the intestinal enzyme acyl CoA: monoacylglycerol acyltransferase-2 protects mice from metabolic disorders induced by high-fat feeding", Nature Medicine, vol. 15, No. 4, Apr. 2009, pp. 442-446.
Barlind et al., "Identification and design of a novel series of MGAT2 inhibitors", Bioorganic & Medicinal Chemistry Letters 23 (2013) pp. 2721-2726.
Scott et al., "Achieving improved permeability by hydrogen bond donor modulation in a series of MGAT2 inhibitors", Med. Chem. Commun., 2013, vol. 4, pp. 1305-1311.
Busujima et al., "Identification of 2-[2-(4-*tert*-butylphenyl)ethyl]-*N*-(4-fluorophenyl)-1,2,3,4-tetrahydroisoquinoline-6-sulfonamide (29) as an orally available MGAT2 inhibitor", Bioorganic & Medicinal Chemistry vol. 23, 2015, pp. 5922-5931.
Sato et al., "Optimization of a novel series of *N*-phenylindoline-5-sulfonamide-based acyl CoA: monoacylglycerol acyltransferase-2 inhibitors: Mitigation of CYP3A4 time-dependent inhibition and phototoxic liabilities", Bioorganic & Medicinal Chemistry, vol. 23, 2015, pp. 4544-4560.
Okuma et al., "JTP-103237, a novel monoacylglycerol acyltransferase inhibitor, modulates fat absorption and prevents diet-induced obesity", European Journal of Pharmacology, vol. 758, 2015, pp. 72-81.
Sato et al., "Discovery of a Novel Series of *N*-Phenylindoline-5-sulfonamide Derivatives as Potent, Selective, and Orally Bioavailable Acyl CoA: Monoacylglycerol Acyltransferase-2 Inhibitors", J. Med. Chem., 2015, vol. 58, pp. 3892-3909.
Adachi et al., "Pharmacological characterization of a series of aryl-sulfonamide derivatives that potently and selectively inhibit monoacylglycerol *acyltransferase* 2", European Journal of Pharmacology, vol. 791, 2016, pp. 569-577.
Ma et al., "Characterization of monoacylglycerol acyltransferase 2 inhibitors by a novel probe in binding assays", Analytical Biochemistry vol. 501, 2016, pp. 48-55.
Devasthale et al., "Monoacylglycerol Acyltransferase 2 (MGAT2) Inhibitors for the Treatment of Metabolic Diseases and Nonalcoholic Steatohepatitis (NASH)", J. Med. Chem. 2018, vol. 61, pp. 9879-9888.
Pettus et al., "Discovery and Optimization of Quinazolinone-pyrrolopyrrolones as Potent and Orally Bioavailable Pan-Pim Kinase Inhibitors", J. Med. Chem. 2016, vol. 59, pp. 6407-6430.
International Preliminary Report on Patentability and Written Opinion of the International Search Authority issued Jul. 22, 2021 in International (PCT) Application No. PCT/JP2020/000553.

* cited by examiner

DIHYDROPYRAZOLOPYRAZINONE DERIVATIVE HAVING MGAT2 INHIBITORY ACTIVITY

TECHNICAL FIELD

The present invention relates to a compound having monoacylglycerol acyltransferase 2 (hereinafter, also referred to as "MGAT2") inhibitory activity or its pharmaceutically acceptable salt, and a pharmaceutical composition including thereof.

BACKGROUND ART

Obesity is defined as an excessively high amount of body fat or adipose tissue in relation to lean body mass and recognized as a major risk factor for health problems. Body mass index (BMI) is a simple index of weight-for-height that is commonly used in classifying overweight and obesity in adult (age 15 and over) populations and individuals. It is defined as the weight in kilograms divided by the square of the height in meters ($kg/m^2$). World Health Organization defines "overweight" as a BMI of 25 $kg/m^2$ or greater and "obesity" as a BMI of 30 $kg/m^2$ or greater. On the other hand, Japan Society for the Study of Obesity defines "obesity" as a BMI of 25 $kg/m^2$ or greater. This is because the number of obesity-related disorders including diabetes and dyslipidemia increases in accordance with BMI, and the mean number of obesity-related disorders is 1.0 or greater at a BMI of 25 $kg/m^2$. World Health Organization reported that about 1600 million and at least 400 million people were classified as overweight and obesity around the world in 2005, respectively. Obesity is mainly caused by taking in more calories than using up in physical activity and daily life. The number of obese people has been increasing by taking in more food including high fat and/or sugar, and it is estimated that 700 million people or more would be diagnosed as obesity around the world in 2015. Diet therapy, exercise therapy, drug therapy, and so on are performed for treatment of obesity. In the drug therapy, drugs including orlistat, mazindol, and sibutramine are used. However, they are not satisfactory in both aspects of efficacy and side effects.

One of the causes for obesity is excessive intake of neutral fat. Neutral fat (triglycerol) taken in meals is decomposed into 2-monoacylglycerol and free fatty acids by the action of pancreatic lipase in the digestive tract, and they are absorbed by small intestinal epithelial cells. An acyl group is transferred from the free fatty acids to the 2-monoacylglycerol by the action of monoacylglycerol acyltransferase (MGAT). The diacylglycerol formed is further converted into neutral fat by the action of diacylglycerol acyltransferase (DGAT).

Three isoforms of MGAT, namely, MGAT1, MGAT2, and MGAT3 have been identified. Among them, MGAT2 and MGAT3 are highly expressed in the small intestine, and believed to be involved in fat absorption in the small intestine.

It has been reported that an experiment with MGAT2 knock-out mice has demonstrated that high-fat diet promotes expression of MGAT2 in the small intestine to increase the MGAT activity (Non-patent Document 1). In addition, reduction of weight gain caused by high-fat diet, suppression of induction of insulin resistance, reduction of increase of blood cholesterol, prevention of fatty liver formation or the like, and promotion of energy consumption have been found for MGAT2 knock-out mice (Non-patent Document 2).

Although compounds having MGAT2 inhibitory activity have been previously reported (Patent Documents 1 to 19, Non-patent Documents 3 to 13), compounds of the present invention as described below have not been disclosed.

PRIOR ART REFERENCES

Patent Documents

[Patent Document 1] International Publication WO 2010/095767 A
[Patent Document 2] International Publication WO 2012/091010 A
[Patent Document 3] International Publication WO 2012/124744 A
[Patent Document 4] International Publication WO 2013/082345 A
[Patent Document 5] International Publication WO 2013/112323 A
[Patent Document 6] International Publication WO 2013/116065 A
[Patent Document 7] International Publication WO 2013/116075 A
[Patent Document 8] International Publication WO 2014/074365 A
[Patent Document 9] International Publication WO 2014/133134 A
[Patent Document 10] International Publication WO 2014/193884 A
[Patent Document 11] JP 2014-5245 A
[Patent Document 12] JP 2014-9165 A
[Patent Document 13] International Publication WO 2015/112465 A
[Patent Document 14] International Publication WO 2015/129845 A
[Patent Document 15] International Publication WO 2015/134699 A
[Patent Document 16] International Publication WO 2015/134701 A
[Patent Document 17] International Publication WO 2015/191681 A
[Patent Document 18] International Publication WO 2016/121782 A
[Patent Document 19] International Publication WO 2017/069224 A

Non-Patent Document

[Non-patent Document 1] Journal of Biological Chemistry (2004), 279, 18878-18886
[Non-patent Document 2] Nature Medicine (2009), 15, (4), 442-446
[Non-patent Document 3] Bioorganic & Medicinal Chemistry Letter (2013), 23, 2721-2726
[Non-patent Document 4] Med. Chem. Commun (2013), 4, 1305-1311
[Non-patent Document 5] Bioorganic & Medicinal Chemistry Letter (2015), 23, 5922-5931
[Non-patent Document 6] Bioorganic & Medicinal Chemistry Letter (2015), 23, 4544-4560
[Non-patent Document 7] Journal of Lipid Research 2015, 56, 747-753
[Non-patent Document 8] European Journal of Pharmacology, 2015, 758, 72-81
[Non-patent Document 9] Journal of Medicinal Chemistry (2015), 58, 3892-3909

[Non-patent Document 10] HETEROCYCLES 2016, 92, 470-484

[Non-patent Document 11] Chemical and Pharmaceutical Bulletin, 2016, 64, 228-238

[Non-patent Document 12] European Journal of Pharmacology, 2016, 791, 569-577

[Non-patent Document 13] Analytical Biochemistry, 2016, 501, 48-55

SUMMARY OF THE INVENTION

Problems to be Solved by the Invention

An object of the present invention is to provide a compound having MGAT2 inhibitory activity or its pharmaceutically acceptable salt, and a pharmaceutical composition including thereof.

Means for Solving the Problem

The present inventors have diligently studied, and succeeded in synthesizing superior compounds having MGAT2 inhibitory activity. This invention includes the followings.

[1]

A compound represented by formula (I):

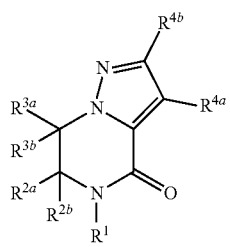

wherein $R^1$ is hydrogen, hydroxy, substituted or unsubstituted carbamoyl, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$R^{2a}$ is a group represented by formula:

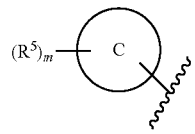

wherein ring C is an aromatic carbocycle, an aromatic heterocycle, a non-aromatic carbocycle, or a non-aromatic heterocycle;

$R^5$s are each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$, and m is an integer of 1 to 5, R$^{2b}$ is hydrogen, cyano, substituted or unsubstituted carbamoyl, substituted or unsubstituted alkyl, substituted or unsubstituted alkenyl, substituted or unsubstituted alkynyl, or substituted or unsubstituted alkylsulfonyl, or R$^{2a}$ and R$^{2b}$ may be taken together with an adjacent carbon atom to form ring B, ring B is a substituted or unsubstituted non-aromatic carbocycle or a substituted or unsubstituted non-aromatic heterocycle;

R$^{3a}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, R$^{3b}$ is hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, R$^{3a}$ and R$^{3b}$ may be taken together with an adjacent carbon atom to form a substituted or unsubstituted non-aromatic carbocycle or a substituted or unsubstituted non-aromatic heterocycle, or R$^{2b}$ and R$^{3b}$ may be taken together with adjacent carbon atoms to form a substituted or unsubstituted non-aromatic carbocycle or a substituted or unsubstituted non-aromatic heterocycle;

R$^{4a}$ is a group represented by formula:

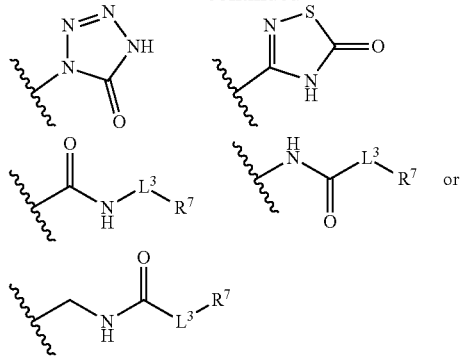

L$^3$ is a single bond or substituted or unsubstituted alkylene,

R$^7$ is hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^{N}$)—R$^{S1}$, a group represented by formula: —N=S(=N—R$^{N}$)—(R$^{S1}$)—R$^{S2}$ or a group represented by formula: —S(=N—R$^{N}$)$_2$—R$^{S1}$, provided that, when L$^3$ is a single bond, R$^7$ is not hydrogen or halogen, R$^{4b}$ is halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^{N}$)—R$^{S1}$, a group represented by formula: —N=S(=N—R$^{N}$)(—R$^{S1}$)—R$^{S2}$, or a group represented by formula: —S(=N—R$^{N}$)$_2$—R$^{S1}$, L is each independently a single bond, alkylene, or C(=O), R$^{S1}$ and R$^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or R$^{S1}$ and R$^{S2}$ bonding to the same sulfur atom may be taken together with the sulfur atom to form a substituted or unsubstituted non-aromatic heterocycle;

R$^{N}$s are each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl, or its pharmaceutically acceptable salt.

[2]

The compound or its pharmaceutically acceptable salt according to [1], wherein ring B is represented by any one of formulas:

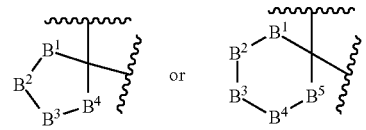

wherein

B$^1$ is CR$^{11a}$R$^{11b}$, NR$^{11c}$, O, or S,
B$^2$ is CR$^{12a}$R$^{12b}$, NR$^{12c}$, O, or S,
B$^3$ is CR$^{13a}$R$^{13b}$, NR$^{13c}$, O, or S,
B$^4$ is CR$^{14a}$R$^{14b}$, NR$^{14c}$, O, or S, and
B$^5$ is CR$^{15a}$R$^{15b}$, NR$^{15c}$, O, or S, R$^{11a}$, R$^{12a}$, R$^{13a}$, R$^{14a}$, and R$^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)—($R^{S1}$)—$R^{S2}$ or a group represented by formula: —S(=N—$R^N$)$_2$—$R^{S1}$, $R^{11b}$, $R^{12b}$, $R^{13b}$, $R^{14b}$ and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)—($R^{S1}$)—$R^{S2}$ or a group represented by formula: —S(=N—$R^N$)$_2$—$R^{S1}$, $R^{11c}$, $R^{12c}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or, $R^{11a}$ and $R^{12a}$, $R^{12a}$ and $R^{13a}$, $R^{13a}$ and $R^{14a}$, and/or $R^{14a}$ and $R^{15a}$ may be taken together with adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and/or, $R^{11c}$ and $R^{12a}$, $R^{11a}$ and $R^{12c}$, $R^{12c}$ and $R^{11a}$, $R^{12c}$ and $R^{13a}$, $R^{12c}$ and $R^{13c}$, $R^{13c}$ and $R^{12a}$, $R^{13c}$ and $R^{14a}$, $R^{13c}$ and $R^{14c}$, $R^{14c}$ and $R^{13a}$, $R^{14c}$ and $R^{15a}$, $R^{14c}$ and $R^{15c}$, and/or, $R^{15c}$ and $R^{14a}$ may be taken together with adjacent atoms to form a substituted or unsubstituted aromatic heterocycle or a substituted or unsubstituted non-aromatic heterocycle, and/or, $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$ may be taken together to form a C2-C4 bridge optionally containing heteroatom(s), and/or, $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ may be taken together to form a bond, and other symbols are as described in [1].

[3]

The compound or its pharmaceutically acceptable salt according to [1] or [2], wherein ring B is represented by any one of formulas:

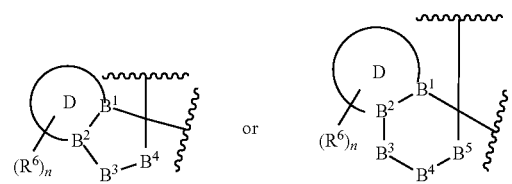

wherein
$B^1$ is C, $CR^{11a}$ or N,
$B^2$ is C, $CR^{12a}$ or N,
$B^3$ is $CR^{13a}R^{13b}$, $NR^{13c}$, O or S,
$B^4$ is $CR^{14a}R^{14b}$, $NR^{14c}$, O or S,
$B^5$ is $CR^{15a}R^{15b}$, $NR^{15c}$, O or S,
$R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)($-R^{S1}$)—$R^{S2}$, a group represented by formula: -L-S(=O)(=N—$R^N$)—$R^{S1}$, a group represented by formula: —N=S(=N—$R^N$)—($R^{S1}$)—$R^{S2}$, or a group represented by formula: —S(=N—$R^N$)$_2$—$R^{S1}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, and/or, $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$ may be taken together to form a C2-C4 bridge optionally containing heteroatom(s), and/or, $R^{11a}$ and $R^{12a}$, $R^{12a}$ and $R^{13b}$, $R^{12a}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ may be taken together to form a bond, ring D is an aromatic carbocycle, a non-aromatic carbocycle, an aromatic heterocycle, or a non-aromatic heterocycle, $R^6$s are each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)—($R^{S1}$)—$R^{S2}$ or a group represented by formula: —S(=N—$R^N$)$_2$—$R^{S1}$, n is an integer of 1 to 4, and other symbols are as described in [1].

[4]

The compound or its pharmaceutically acceptable salt according to any one of [1] to [3], wherein ring B is represented by any one of formulas:

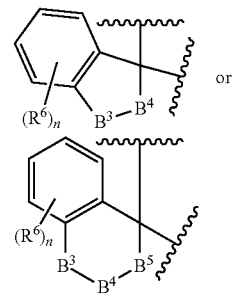

wherein $B^3$, $B^4$, $B^5$, $R^6$ and n are as described in [3].

[5]

The compound or its pharmaceutically acceptable salt according to any one of [1] to [4], wherein ring B is represented by any one of formulas:

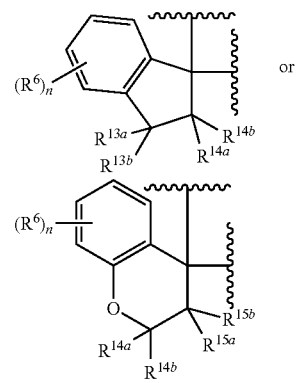

wherein $R^6$, $R^{13a}$, $R^{13b}$, $R^{14a}$, $R^{14b}$, $R^{15a}$, $R^{15b}$, and n are as described in [3].

[6]

The compound or its pharmaceutically acceptable salt according to [3] or [4], wherein $R^6$s is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

[7]

The compound or its pharmaceutically acceptable salt according to any one of [3] to [5], wherein $R^6$s are each independently halogen, or substituted or unsubstituted alkyloxy.

[8]

The compound or its pharmaceutically acceptable salt according to any one of [3] to [5], wherein ring B is represented by any one of formulas:

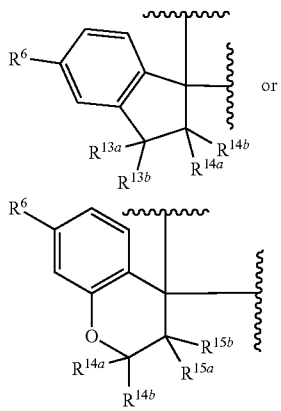

wherein R$^6$s are each independently substituted or unsubstituted alkyloxy, and R$^{13a}$, R$^{13b}$, R$^{14a}$, R$^{14b}$, R$^{15a}$, and R$^{15b}$ are as described in [3].

[9]

The compound or its pharmaceutically acceptable salt according to any one of [3] to [5], wherein ring B is represented by any one of formulas:

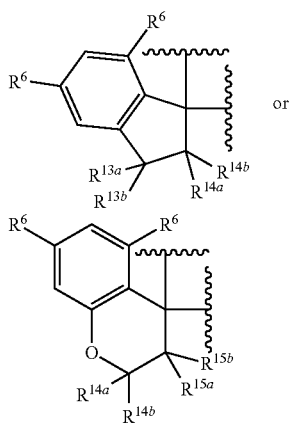

wherein R$^6$s are each independently halogen, or substituted or unsubstituted alkyloxy, and R$^{13a}$, R$^{13b}$, R$^{14a}$, R$^{14b}$, R$^{15a}$, and R$^{15b}$ are as described in [3].

[10]

The compound or its pharmaceutically acceptable salt according to [1], wherein ring C is an aromatic carbocycle or an aromatic heterocycle.

[11]

The compound or its pharmaceutically acceptable salt according to [1] or [10], wherein R$^5$s are each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl, and m is 1 to 3.

[12]

The compound or its pharmaceutically acceptable salt according to any one of [1], [10] and [11], wherein R$^{2b}$ is substituted or unsubstituted alkyl.

[13]

The compound or its pharmaceutically acceptable salt according to any one of [1] to [12], wherein R$^{4a}$ is a group represented by formula:

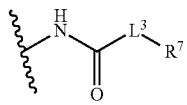

wherein
L$^3$ and R$^7$ are as described in [1].

[14]

The compound or its pharmaceutically acceptable salt according to any one of [1] to [13], wherein L$^3$ is substituted or unsubstituted alkylene.

[15]

The compound or its pharmaceutically acceptable salt according to [14], wherein R$^7$ is halogen, substituted or unsubstituted sulfamoyl, substituted or unsubstituted alkyl, substituted or unsubstituted alkyloxy, substituted or unsubstituted alkylsulfonyl, or a group represented by formula: -L-S(=O)(=N—R$^N$)—R$^{S1}$.

[16]

The compound or its pharmaceutically acceptable salt according to any one of [1] to [13], wherein L$^3$ is a single bond.

[17]

The compound or its pharmaceutically acceptable salt according to [16], wherein R$^7$ is substituted or unsubstituted aromatic heterocyclyl, or substituted or unsubstituted non-aromatic heterocyclyl.

[18]

The compound or its pharmaceutically acceptable salt according to any one of [1] to [17], wherein R$^{4b}$ is substituted or unsubstituted alkyl, substituted or unsubstituted aromatic carbocyclyl, or substituted or unsubstituted aromatic heterocyclyl.

[19]

The compound or its pharmaceutically acceptable salt according to any one of [1] to [18], wherein R$^{3a}$ and R$^{3b}$ are each hydrogen.

[20]

The compound or its pharmaceutically acceptable salt according to [1], selected from the group consisting of Compounds I-6, I-13, I-14, I-20, I-33, I-46, I-58, I-61, I-66, I-79, I-126, I-130, I-133, I-137, and I-142.

[20-1]

The compound or its pharmaceutically acceptable salt according to [1], selected from the group consisting of Compounds I-123, I-124, I-136, I-139, I-141, I-143, I-145, and I-147.

[20-2]

The compound or its pharmaceutically acceptable salt according to [1], selected from the group consisting of Compounds I-151 and I-153.

[21]

A pharmaceutical composition comprising the compound or its pharmaceutically acceptable salt according to any one of [1] to [20] and [20-1] to [20-2].

[22]

The pharmaceutical composition according to [21], having MGAT2 inhibitory activity.

[23]

The pharmaceutical composition according to [21] or [22], for use in treating or preventing an MGAT2-associated disease.

[24]

The pharmaceutical composition according to [23], for use in treating or preventing obesity, metabolic syndrome, hyperlipidemia, hypertriglyceridemia, hyper-VLDL-triglyceridemia, hyperfattyacidemia, diabetes mellitus, or arteriosclerosis.

[25]

A method for treating or preventing an MGAT2-associated disease, comprising administering the compound or its pharmaceutically acceptable salt according to any one of [1] to [20] and [20-1] to [20-2].

[26]

The compound or its pharmaceutically acceptable salt according to any one of [1] to [20] and [20-1] to [20-2] for treating or preventing an MGAT2-associated disease.

[27]

A use of the compound according to any one of [1] to [20] and [20-1] to [20-2], or its pharmaceutically acceptable salt, for treating or preventing an MGAT2-associated disease.

[1']

A compound represented by formula (I):

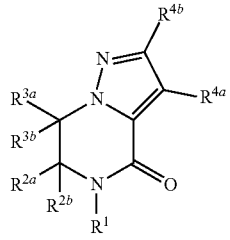

(I)

wherein

R$^1$ is hydrogen;

R$^{2a}$ and R$^{2b}$ are taken together with an adjacent carbon atom to form ring B, ring B is represented by formula:

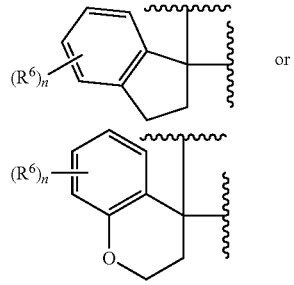

wherein R$^6$s are each independently halogen, or substituted or unsubstituted alkyloxy, and n is 1 or 2;

R$^{3a}$ is hydrogen;

R$^{3b}$ is hydrogen;

R$^{4a}$ is a group represented by formula:

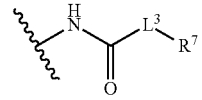

wherein

L$^3$ is a single bond or substituted or unsubstituted alkylene,

R$^7$ is halogen, substituted or unsubstituted sulfamoyl, substituted or unsubstituted alkyloxy, substituted or unsubstituted alkylsulfonyl, substituted or unsubstituted aromatic heterocyclyl, substituted or unsubstituted non-aromatic heterocyclyl, or a group represented by a group represented by formula: —S(=O)(=N—R$^N$)—R$^{S1}$, R$^N$ is hydrogen, and R$^{S1}$ is substituted or unsubstituted alkyl; and R$^{4b}$ is substituted or unsubstituted alkyl, substituted or unsubstituted aromatic carbocyclyl, or substituted or unsubstituted aromatic heterocyclyl, or its pharmaceutically acceptable salt.

[2']

The compound or its pharmaceutically acceptable salt according to [1'], wherein ring B is represented by any one of formulas:

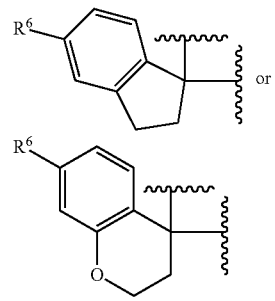

wherein R$^6$s are each independently substituted or unsubstituted alkyloxy.

[3']

The compound or its pharmaceutically acceptable salt according to [1'], wherein ring B is represented by any one of formulas:

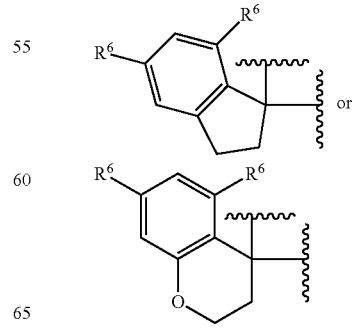

wherein R⁶s are each independently halogen, or substituted or unsubstituted alkyloxy.

[4']
The compound or its pharmaceutically acceptable salt according to any one of [1'] to [3'], wherein L³ is substituted or unsubstituted alkylene.

[5']
The compound or its pharmaceutically acceptable salt according to [4'], wherein R⁷ is halogen, substituted or unsubstituted sulfamoyl, substituted or unsubstituted alkyloxy, substituted or unsubstituted alkylsulfonyl, or a group represented by formula: —S(=O)(=N—R$^N$)—R$^{S1}$.

[6']
The compound or its pharmaceutically acceptable salt according to any one of [1'] to [3'], wherein L³ is a single bond.

[7']
The compound or its pharmaceutically acceptable salt according to [6'], wherein R⁷ is substituted or unsubstituted aromatic heterocyclyl, or substituted or unsubstituted non-aromatic heterocyclyl.

[8']
A compound or its pharmaceutically acceptable salt according to [1'], selected from the group consisting of Compounds I-6, I-13, I-14, I-20, I-33, I-46, I-58, I-61, I-66, I-79, I-126, I-130, I-133, I-137, and I-142.

[8'-1]
The compound or its pharmaceutically acceptable salt according to [1'], selected from the group consisting of Compounds I-123, I-124, I-136, I-139, I-141, I-143, I-145, and I-147.

[8'-2]
The compound or its pharmaceutically acceptable salt according to [1'], selected from the group consisting of Compounds I-151 and I-153.

[9']A pharmaceutical composition comprising the compound or its pharmaceutically acceptable salt according to any one of [1'] to [8'] and [8'-1] to [8'-2].

[10']
The pharmaceutical composition according to [9'], having MGAT2 inhibitory activity.

[11']
The pharmaceutical composition according to [9'] or [10'], for use in treating or preventing an MGAT2-associated disease.

[12']
The pharmaceutical composition according to [11'], for use in treating or preventing obesity, metabolic syndrome, hyperlipidemia, hypertriglyceridemia, hyper-VLDL-triglyceridemia, hyperfattyacidemia, diabetes mellitus, or arteriosclerosis.

[13']
A method for treating or preventing an MGAT2-associated disease, comprising administering the compound or its pharmaceutically acceptable salt according to any one of [1'] to [8'] and [8'-1] to [8'-2].

[14']
The compound or its pharmaceutically acceptable salt according to any one of [1'] to [8'] and [8'-1] to [8'-2] for treating or preventing an MGAT2-associated disease.

[15']
A use of the compound according to any one of [1'] to [8'] and [8'-1] to [8'-2], or its pharmaceutically acceptable salt, for treating or preventing an MGAT2-associated disease.

Effect of the Invention

The compound according to the present invention has MGAT2 inhibitory activity, and is useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

MODE FOR CARRYING OUT THE INVENTION

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

The term "halogen" includes a fluorine atom, a chlorine atom, a bromine atom and an iodine atom. In particular, a fluorine atom and a chlorine atom are preferable.

The term "alkyl" includes a C1 to C15, preferably a C1 to C10, more preferably a C1 to C6, and further preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6, and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

A preferred embodiment of "alkenyl" is vinyl, allyl, propenyl, isopropenyl or butenyl.

The term "alkynyl" includes a C2 to C10, preferably a C2 to C8, more preferably a C2 to C6, and further preferably a C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

The term "alkylene" includes a C1 to C15, preferably a C1 to C10, more preferably a C1 to C6, and further preferably a C1 to C4 liner or branched divalent hydrocarbon group. Examples include methylene, ethylene, propylene, tetramethylene, pentamethylene, and hexamethylene.

The term "aromatic carbocyclyl" means a cyclic aromatic hydrocarbon group which is monocyclic or polycyclic having two or more rings. Examples include phenyl, naphthyl, anthryl, and phenanthryl.

A preferred embodiment of "aromatic carbocyclyl" is phenyl.

The term "non-aromatic carbocyclyl" means a cyclic saturated hydrocarbon group or a cyclic unsaturated non-aromatic hydrocarbon group, which is monocyclic or polycyclic having two or more rings. The "non-aromatic carbocyclyl" which is polycyclic having two or more rings includes a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

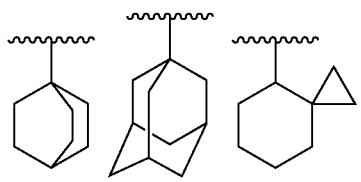

The non-aromatic carbocyclyl which is monocyclic is preferably C3 to C16 carbocyclyl, more preferably C3 to C12 carbocyclyl, and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

A non-aromatic carbocyclyl which is polycyclic having two or more rings is preferably C8 to C20 carbocyclyl, and more preferably C8 to C16 carbocyclyl. Examples include indanyl, indenyl, acenaphthyl, tetrahydronaphthyl, and fluorenyl.

The term "aromatic carbocycle" includes a cyclic aromatic hydrocarbon which is monocyclic or polycyclic having two or more rings. Examples include a benzene ring, a naphthalene ring, an anthracene ring, and a phenanthrene ring.

An embodiment of "aromatic carbocycle" is a benzene ring and a naphthalene ring. Another embodiment thereof includes a benzene ring.

The term "non-aromatic carbocycle" includes a cyclic saturated hydrocarbon or a cyclic unsaturated non-aromatic hydrocarbon, which is monocyclic or polycyclic having two or more rings. The "non-aromatic carbocycle", which is polycyclic having two or more rings, includes a fused ring wherein the non-aromatic carbocycle, which is monocyclic or polycyclic having two or more rings, is fused with a ring of the above "aromatic carbocycle".

In addition, examples of the "non-aromatic carbocycle" also include a ring having a bridge or a ring to form a spiro ring as follows:

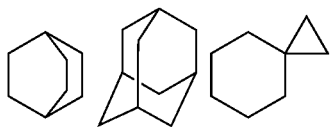

The non-aromatic carbocycle which is monocyclic is preferably a C3 to C16 carbocycle, more preferably a C3 to C12 carbocycle, and further preferably a C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, and cyclohexadiene.

A non-aromatic carbocycle which is polycyclic having two or more rings is preferably a C8 to C20 carbocycle, and more preferably a C8 to C16 carbocycle. Examples include indane, indene, acenaphthene, tetrahydronaphthalene, and fluorene.

The term "aromatic heterocyclyl" means an aromatic cyclyl, which is monocyclic or polycyclic having two or more rings, containing one or more, same or different heteroatom(s) selected independently from O, S and N. The "aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered ring, and more preferably a 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

An aromatic heterocyclyl which is bicyclic is preferably an 8- to 10-membered ring, and more preferably a 9- or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

Examples of aromatic heterocyclyl, which is polycyclic having three or more rings, include carbazolyl, acridinyl, xanthenyl, phenothiazinyl, phenoxathiinyl, phenoxazinyl, and dibenzofuryl.

The term "non-aromatic heterocyclyl" means a non-aromatic cyclyl, which is monocyclic or polycyclic having two or more rings, containing one or more, same or different heteroatom(s) selected independently from O, S and N. Non-aromatic heterocyclyl, which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl", and includes a fused ring group wherein a ring of the above "aromatic heterocyclyl" is fused with the above "non-aromatic carbocyclyl", which is monocyclic or polycyclic having two or more ring(s).

In addition, examples of the "non-aromatic heterocyclyl" also include a group having a bridge or a group to form a spiro ring as follows:

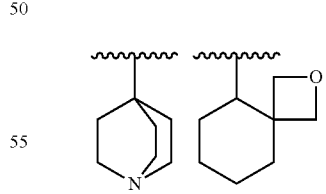

The non-aromatic heterocyclyl, which is monocyclic, is preferably a 3- to 8-membered, and more preferably a 5- to 6-membered. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolynyl, oxepanyl, thiolanyl, thiinyl, and thiazinyl.

A non-aromatic heterocyclyl which is polycyclic having two or more rings is preferably an 8- to 20-membered, and more preferably an 8- to 10-membered. Examples include indolinyl, isoindolinyl, chromanyl, and isochromanyl.

The term "aromatic heterocycle" includes an aromatic ring, which is monocyclic or polycyclic having two or more rings, containing one or more, same or different heteroatom(s) selected independently from O, S and N.

The "aromatic heterocycle", which is polycyclic having two or more rings, includes a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered ring, and more preferably a 5- or 6-membered ring. Examples include pyrrole, imidazole, pyrazole, pyridine, pyridazine, pyrimidine, pyrazine, triazole, triazine, tetrazole, furan, thiophen, isoxazole, oxazole, oxadiazole, isothiazole, thiazole, and thiadiazole.

The aromatic heterocycle, which is bicyclic, is preferably an 8- to 10-membered, and more preferably a 9- or 10-membered. Examples include indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, and thiazolopyridine.

The aromatic heterocycle, which is polycyclic having three or more rings, is preferably a 11- to 26-membered ring, and more preferably a 13- or 14-membered ring. Examples include carbazole, acridine, xanthene, phenothiazine, phenoxathiine, phenoxazine, and dibenzofuran.

The term "non-aromatic heterocycle" includes a cyclic non-aromatic ring, which is monocyclic or polycyclic having two or more rings, containing one or more, same or different heteroatom(s) selected independently from an oxygen atom, a sulfur atom, and a nitrogen atom.

The "non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, the "non-aromatic heterocycle" also includes a ring having a bridge or a ring to form a spiro ring as follows:

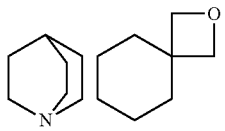

The non-aromatic heterocycle which is monocyclic is preferably a 3 to 8-membered ring, and more preferably a 5 or 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyrane, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxole, oxepane, thiolane, thiine, and thiazine.

A non-aromatic heterocycle which is polycyclic having two or more rings is preferably an 8- to 20-membered, and more preferably an 8- to 10-membered. Examples include indoline, isoindoline, chroman, and isochroman.

The substituents of "substituted carbamoyl", "substituted thiocarbamoyl", "substituted amidino", "substituted amino", "substituted ureido", "substituted guanidino", "substituted sulfamoyl", "substituted alkyl", "substituted alkenyl", "substituted alkynyl", "substituted alkylene", "substituted alkyloxy", "substituted alkenyloxy", "substituted alkylcarbonyloxy", "substituted alkenylcarbonyloxy", "substituted alkylcarbonyl", "substituted alkenylcarbonyl", "substituted alkyloxycarbonyl", "substituted alkenyloxycarbonyl", "substituted alkylsulfanyl", "substituted alkenylsulfanyl", "substituted alkylsulfinyl", "substituted alkenylsulfinyl", "substituted alkylsulfonyl", and "substituted alkenylsulfonyl" include the substituents given below. A carbon atom or nitrogen atom at any position(s) may be bonded to one or more group(s) selected from the following substituents.

Substituent group: halogen, hydroxy, cyano, formyl, formyl oxy, thioformyl, carboxy, thiocarboxy, dithiocarboxy, carbamoyl thiocarbamoyl, amidino, amino, hydroxyamino, azido, hydradino, ureido, guanidino, pentafluorothio, thiol, sulfino, sulfo, sulfamoyl, trialkylsilyl, alkyl, alkenyl, alkynyl, haloalkyl, haloalkenyl, haloalkynyl, alkyloxy, alkenyloxy, alkynyloxy, haloalkyloxy, haloalkyloxyalkyl, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, dialkylamino, dialkenylamino, dialkynylamino, monoalkylcarbonylamino, monoalkenylcarbonylamino, monoalkynylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarbamoyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl optionally substituted with Substituent Group A, non-aromatic carbocyclyl optionally substituted with Substituent Group A, aromatic heterocyclyl optionally substituted with Substituent Group A, non-aromatic heterocyclyl optionally substituted with Substituent Group A, aromatic carbocyclyloxy optionally substituted with Substituent Group A, non-aromatic carbocyclyloxy optionally substituted with Substituent Group A, aromatic heterocyclyloxy optionally substituted with Substituent Group A, non-aromatic heterocyclyloxy optionally substituted with Substituent Group A, aromatic carbocyclylcarbonyloxy optionally substituted with Substituent Group A, non-aromatic carbocyclylcarbonyloxy optionally substituted with Substituent Group A, aromatic heterocyclylcarbonyloxy optionally substituted with Substituent Group A, non-aromatic heterocyclylcarbonyloxy optionally substituted with Substituent Group A, aromatic carbocyclylcarbonyl optionally substituted with Substituent Group A, non-aromatic carbocyclylcarbonyl optionally substituted with Substituent Group A, aromatic heterocyclylcarbonyl optionally substituted with Substituent Group A, non-aromatic heterocyclylcarbonyl optionally substituted with Substituent Group A, aromatic carbocyclyloxycarbonyl optionally substituted with Substituent Group A, non-aromatic carbocyclyloxycarbonyl optionally substituted with Substituent Group A, aromatic heterocyclyloxycarbonyl optionally substituted with Substituent Group A, non-aromatic heterocyclyloxycarbonyl optionally substituted with Substituent Group A, aromatic carbocyclylsulfanyl optionally substituted with Substituent Group A, non-aromatic carbocyclylsulfanyl optionally substituted with Substituent Group A, aromatic heterocyclylsulfanyl optionally substituted with Substituent Group A, non-aromatic heterocyclylsulfanyl optionally substituted with Substituent Group A, aromatic carbocyclylsulfinyl optionally substituted with Substituent Group A, non-aromatic carbocyclylsulfinyl optionally substituted with Substituent Group A, aromatic heterocyclylsulfinyl optionally substituted with Substituent Group A, non-aromatic heterocyclylsulfinyl optionally substituted with Substituent Group A, aromatic carbocyclylsulfonyl optionally substituted with Substituent Group A, non-aromatic carbocyclylsulfonyl optionally substituted with Substituent Group A, aromatic heterocyclylsulfonyl optionally substituted with Substituent Group A, non-aromatic heterocyclylsulfonyl optionally substituted with Substituent Group A, aromatic carbocyclylalkyl optionally substituted with Substituent Group A, non-aromatic carbocyclylalkyl optionally substituted with Substituent Group A, aromatic heterocyclylalkyl optionally substituted with Substituent Group A, non-aromatic heterocyclylalkyl optionally substituted with Substituent Group A, aromatic carbocyclylalkyloxy optionally substituted with Substituent Group A, non-aromatic carbocyclylalkyloxy optionally substituted with Substituent Group A, aromatic heterocyclylalkyloxy optionally substituted with Substituent Group A, non-aromatic heterocyclylalkyloxy optionally substituted with Substituent Group A, aromatic carbocyclylalkylcarbonyl optionally substituted with Substituent Group A, non-aromatic carbocyclylalkylcarbonyl optionally substituted with Substituent Group A, aromatic heterocyclylalkylcarbonyl optionally substituted with Substituent Group A, non-aromatic heterocyclylalkylcarbonyl optionally substituted with Substituent Group A, aromatic carbocyclylalkyloxycarbonyl optionally substituted with Substituent Group A, non-aromatic carbocyclylalkyloxycarbonyl, aromatic heterocyclylalkyloxycarbonyl optionally substituted with Substituent Group A, non-aromatic heterocyclylalkyloxycarbonyl optionally substituted with Substituent Group A, aromatic carbocyclylalkylsulfanyl optionally substituted with Substituent Group A, non-aromatic carbocyclylalkylsulfanyl optionally substituted with Substituent Group A, aromatic heterocyclylalkylsulfanyl optionally substituted with Substituent Group A, non-aromatic heterocyclylalkylsulfanyl optionally substituted with Substituent Group A, aromatic carbocyclylalkylsulfinyl optionally substituted with Substituent Group A, non-aromatic carbocyclylalkylsulfinyl optionally substituted with Substituent Group A, aromatic heterocyclylalkylsulfinyl optionally substituted with Substituent Group A, non-aromatic heterocyclylalkylsulfinyl optionally substituted with Substituent Group A, aromatic carbocyclylalkylsulfonyl optionally substituted with Substituent Group A, non-aromatic carbocyclylalkylsulfonyl optionally substituted with Substituent Group A, aromatic heterocyclylalkylsulfonyl optionally substituted with Substituent Group A, non-aromatic heterocyclylalkylsulfonyl optionally substituted with Substituent Group A, aromatic carbocyclylalkylamino optionally substituted with Substituent Group A, non-aromatic carbocyclylalkylamino optionally substituted with Substituent Group A, aromatic heterocyclylalkylamino optionally substituted with Substituent Group A, non-aromatic heterocyclylalkylamino optionally substituted with Substituent Group A, aromatic carbocyclylalkylcarbonylamino optionally substituted with Substituent Group A, non-aromatic carbocyclylalkylcarbonylamino optionally substituted with Substituent Group A, aromatic heterocyclylalkylcarbonylamino optionally substituted with Substituent Group A, non-aromatic heterocyclylalkylcarbonylamino optionally substituted with Substituent Group A, aromatic carbocyclylalkyloxycarbonylamino optionally substituted with Substituent Group A, non-aromatic carbocyclylalkyloxycarbonylamino optionally substituted with Substituent Group A, aromatic heterocyclylalkyloxycarbonylamino optionally substituted with Substituent Group A, non-aromatic heterocyclylalkyloxycarbonylamino optionally substituted with Substituent Group A, aromatic carbocyclylalkylsulfonylamino optionally substituted with Substituent Group A, non-aromatic carbocyclylalkylsulfonylamino optionally substituted with Substituent Group A, aromatic heterocyclylalkylsulfonylamino optionally substituted with Substituent Group A, non-aromatic heterocyclylalkylsulfonylamino optionally substituted with Substituent Group A, aromatic carbocyclyloxyalkylamino optionally substituted with Substituent Group A, non-aromatic carbocyclyloxyalkylamino optionally substituted with Substituent Group A, aromatic heterocyclyloxyalkylamino optionally substituted with Substituent Group A, and non-aromatic heterocyclyloxyalkylamino optionally substituted with Substituent Group A.

The term "optionally substituted with Substituent Group A" means that a carbon atom, nitrogen atom or sulfur atom at any position may be bonded to one or more groups selected from Substituent Group A.

Substituent Group A: oxo, halogen, hydroxy, alkyl, haloalkyl, hydroxyalkyl, alkyloxy, haloalkyloxy, alkyloxycarbonylalkyl, monoalkylamino, dialkylamino, aromatic carbocyclyl, aromatic heterocyclyl, and aromatic carbocyclyloxy.

Hereinafter, the same applies to the term "optionally substituted with Substituent Group B".

Substituent Group B: halogen, alkyl, and haloalkyl.

The substituents on the ring of "aromatic carbocycle", "non-aromatic carbocycle", "aromatic heterocycle", or "non-aromatic heterocycle" of "substituted non-aromatic carbocycle", "substituted non-aromatic heterocycle", "substituted aromatic carbocyclyl", "substituted non-aromatic carbocyclyl", "substituted aromatic heterocyclyl", "substituted non-aromatic heterocyclyl", "substituted aromatic carbocyclyloxy", "substituted non-aromatic carbocyclyloxy", "substituted aromatic heterocyclyloxy", "substituted non-aromatic heterocyclyloxy", "substituted aromatic carbocyclylcarbonyloxy", "substituted non-aromatic carbocyclylcarbonyloxy", "substituted aromatic heterocyclylcarbonyloxy", "substituted non-aromatic heterocyclylcarbonyloxy", "substituted aromatic carbocyclylcarbonyl", "substituted non-aromatic carbocyclylcarbonyl", "substituted aromatic heterocyclylcarbonyl", "substituted non-aromatic heterocyclylcarbonyl", "substituted aromatic carbocyclyloxycarbonyl", "substituted non-aromatic carbocyclyloxycarbonyl", "substituted aromatic heterocyclyloxycarbonyl", "substituted non-aromatic heterocyclyloxycarbonyl", "substituted aromatic carbocyclylsulfanyl", "substituted non-aromatic carbocyclylsulfanyl", "substituted aromatic heterocyclylsulfanyl", "substituted non-aromatic heterocyclylsulfanyl", "substituted aromatic carbocyclylsulfinyl", "substituted non-aromatic carbocyclylsulfinyl", "substituted aromatic heterocyclylsulfinyl", "substituted non-aromatic heterocyclylsulfinyl", "substituted aromatic carbocyclylsulfonyl", "substituted non-aromatic carbocyclylsulfonyl", "substituted aromatic heterocyclylsulfonyl", and "substituted non-aromatic heterocyclylsulfonyl" include the substituents given below. An atom at any position(s) on the ring may be bonded to one or more group(s) selected from the following substituents.

Substituents: oxo, halogen, hydroxy, cyano, formyl, formyloxy, thioformyl, carboxy, thiocarboxy, dithiocarboxy, carbamoyl, thiocarbamoyl, amidino, amino, hydroxyamino, imino, hydroxyimino, azide, hydrazino, ureido, guanidino, pentafluorothio, thiol, sulfino, sulfo, sulfamoyl, trialkylsilyl, alkyl, alkenyl, alkynyl, haloalkyl, alkyloxy, alkenyloxy, alkynyloxy, haloalkyloxy, haloalkenyloxy, haloalkynyloxy, alkyloxyalkyloxy, haloalkyloxyalkyloxy, hydroxyalkyl, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, monohaloalkylamino, dialkylamino, dialkenylamino, dialkynylamino, monoalkylcarbonylamino, monoalkenylcarbonylamino, monoalkynylcarbonylamino, monohaloalkylcarbonylamino, dialkylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, alkylimino, alkenylimino, alkynylimino, alkyloxyimino, alkenyloxyimino, alkynyloxyimino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarbamoyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl optionally substituted with Substituent Group A, non-aromatic carbocyclyl optionally substituted with Substituent Group A, aromatic heterocyclyl optionally substituted with Substituent Group A, non-aromatic heterocyclyl optionally substituted with Substituent Group A, aromatic carbocyclyloxy optionally substituted with Substituent Group A, non-aromatic carbocyclyloxy optionally substituted with Substituent Group A, aromatic heterocyclyloxy optionally substituted with Substituent Group A, non-aromatic heterocyclyloxy optionally substituted with Substituent Group A, aromatic carbocyclylcarbonyloxy optionally substituted with Substituent Group A, non-aromatic carbocyclylcarbonyloxy optionally substituted with Substituent Group A, aromatic heterocyclylcarbonyloxy optionally substituted with Substituent Group A, non-aromatic heterocyclylcarbonyloxy optionally substituted with Substituent Group A, aromatic carbocyclylcarbonyl optionally substituted with Substituent Group A, non-aromatic carbocyclylcarbonyl optionally substituted with Substituent Group A, aromatic heterocyclylcarbonyl optionally substituted with Substituent Group A, non-aromatic heterocyclylcarbonyl optionally substituted with Substituent Group A, aromatic carbocyclyloxycarbonyl optionally substituted with Substituent Group A, non-aromatic carbocyclyloxycarbonyl optionally substituted with Substituent Group A, aromatic heterocyclyloxycarbonyl optionally substituted with Substituent Group A, non-aromatic heterocyclyloxycarbonyl optionally substituted with Substituent Group A, aromatic carbocyclylsulfanyl optionally substituted with Substituent Group A, non-aromatic carbocyclylsulfanyl optionally substituted with Substituent Group A, aromatic heterocyclylsulfanyl optionally substituted with Substituent Group A, non-aromatic heterocyclylsulfanyl optionally substituted with Substituent Group A, aromatic carbocyclylsulfinyl optionally substituted with Substituent Group A, non-aromatic carbocyclylsulfinyl optionally substituted with Substituent Group A, aromatic heterocyclylsulfinyl optionally substituted with Substituent Group A, non-aromatic heterocyclylsulfinyl optionally substituted with Substituent Group A, aromatic carbocyclylsulfonyl optionally substituted with Substituent Group A, non-aromatic carbocyclylsulfonyl optionally substituted with Substituent Group A, aromatic heterocyclylsulfonyl optionally substituted with Substituent Group A, non-aromatic heterocyclylsulfonyl optionally substituted with Substituent Group A, aromatic carbocyclylamino optionally substituted with Substituent Group A, non-aromatic carbocyclylamino optionally substituted with Substituent Group A, aromatic heterocyclylamino optionally substituted with Substituent Group A, non-aromatic heterocyclylamino optionally substituted with Substituent Group A, aromatic carbocyclylalkyl optionally substituted with Substituent Group A, non-aromatic carbocyclylalkyl optionally substituted with Substituent Group A, aromatic heterocyclylalkyl optionally substituted with Substituent Group A, non-aromatic heterocyclylalkyl optionally substituted with Substituent Group A, aromatic carbocyclylalkyloxy optionally substituted with Substituent Group A, non-aromatic carbocyclylalkyloxy optionally substituted with Substituent Group A, aromatic heterocyclylalkyloxy optionally substituted with Substituent Group A, non-aromatic heterocyclylalkyloxy optionally substituted with Substituent Group A, aromatic carbocyclylalkylcarbonyl optionally substituted with Substituent Group A, non-aromatic carbocyclylalkylcarbonyl optionally substituted with Substituent Group A, aromatic heterocyclylalkylcarbonyl optionally substituted with Substituent Group A, non-aromatic heterocyclylalkylcarbonyl optionally substituted with Substituent Group A, aromatic carbocyclylalkyloxycarbonyl optionally substituted with Substituent Group A, non-aromatic carbocyclylalkyloxycarbonyl, aromatic heterocyclylalkyloxycarbonyl optionally substituted with Substituent Group A, non-aromatic heterocyclylalkyloxycarbonyl optionally substituted with Substituent Group A, aromatic carbocyclylalkylsulfanyl optionally substituted with Substituent Group A, non-aromatic carbocyclylalkylsulfanyl optionally substituted with Substituent Group A, aromatic heterocyclylalkylsulfanyl optionally substituted with Substituent Group A, non-aromatic heterocyclylalkylsulfanyl optionally substituted with Substituent Group A, aromatic carbocyclylalkylsulfinyl optionally substituted with Substituent Group A, non-aromatic carbocyclylalkylsulfinyl optionally substituted with Substituent Group A, aromatic heterocyclylalkylsulfinyl optionally substituted with Substituent Group A, non-aromatic heterocyclylalkylsulfinyl optionally substituted with Substituent Group A, aromatic carbocyclylalkylsulfonyl optionally substituted with Substituent Group A, non-aromatic carbocyclylalkylsulfonyl optionally substituted with Substituent Group A, aromatic heterocyclylalkylsulfonyl optionally substituted with Substituent Group A, non-aromatic heterocyclylalkylsulfonyl optionally substituted with Substituent Group A, aromatic carbocyclylalkylamino optionally substituted with Substituent Group A, non-aromatic carbocyclylalkylamino optionally substituted with Substituent Group A, aromatic heterocyclylalkylamino optionally substituted with Substituent Group A, non-aromatic heterocyclylalkylamino optionally substituted with Substituent Group A, aromatic carbocyclylalkylcarbonylamino optionally substituted with Substituent Group A, non-aromatic carbocyclylalkylcarbonylamino optionally substituted with Substituent Group A, aromatic heterocyclylalkylcarbonylamino optionally substituted with Substituent Group A, non-aromatic heterocyclylalkylcarbonylamino optionally substituted with Substituent Group A, aromatic carbocyclylalkyloxycarbonylamino optionally substituted with Substituent Group A, non-aromatic carbocyclylalkyloxycarbonylamino optionally substituted with Substituent Group A, aromatic heterocyclylalkyloxycarbonylamino optionally substituted with Substituent Group A, non-aromatic heterocyclylalkyloxycarbonylamino optionally substituted with Substituent Group A, aromatic carbocyclylalkylsulfonylamino optionally substituted with Substituent Group A, non-aromatic carbocyclylalkylsulfonylamino optionally substituted with Substituent Group A, aromatic heterocyclylalkylsulfonylamino optionally substituted with Substituent Group A, non-aromatic heterocyclylalkylsulfonylamino optionally substituted with Substituent Group A, aromatic carbocyclyloxyalkylamino optionally substituted with Substituent Group A, non-aromatic carbocyclyloxyalkylamino optionally substituted with Substituent Group A, aromatic heterocyclyloxyalkylamino optionally substituted with Substituent Group A, and non-aromatic heterocyclyloxyalkylamino optionally substituted with Substituent Group A.

Embodiments and preferred embodiments of each substituent in the compound represented by formula (I) are shown below. The following compounds having possible combination of the embodiments of each substituent are preferable.

$R^1$ includes hydrogen, hydroxy, substituted or unsubstituted carbamoyl, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A preferred embodiment of $R^1$ is hydrogen or hydroxy.

A more preferred embodiment of $R^1$ is hydrogen.

Examples of the substituent in the case that $R^1$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

In a preferred embodiment, $R^{2a}$ and $R^{2b}$ are taken together with an adjacent carbon atom to form ring B.

As another embodiment of $R^{2a}$ and $R^{2b}$, the following embodiments are also preferable, $R^{2a}$ is a group represented by formula:

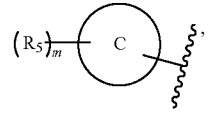

and $R^{2b}$ is hydrogen, cyano, substituted or unsubstituted carbamoyl, substituted or unsubstituted alkyl, substituted or unsubstituted alkenyl, substituted or unsubstituted alkynyl, or substituted or unsubstituted alkylsulfonyl.

A more preferred embodiment of $R^{2b}$ is hydrogen or substituted or unsubstituted alkyl.

A particularly preferred embodiment of $R^{2b}$ is substituted or unsubstituted alkyl, and alkyl and haloalkyl are particularly preferable.

Examples of the substituent in the case that $R^{2b}$ is substituted include halogen.

Ring B includes a substituted or unsubstituted non-aromatic carbocycle or a substituted or unsubstituted non-aromatic heterocycle.

A preferred embodiment of ring B is a group represented by formula:

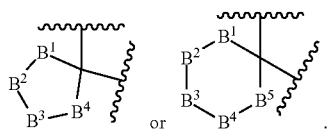

A more preferred embodiment of ring B is a group represented by formula:

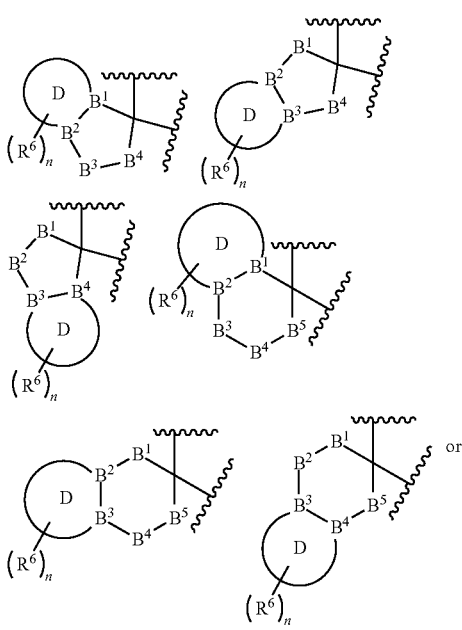

A particularly preferred embodiment of ring B is a group represented by formula:

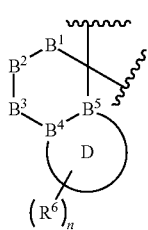

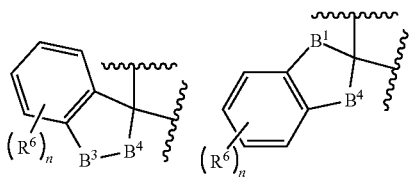

-continued

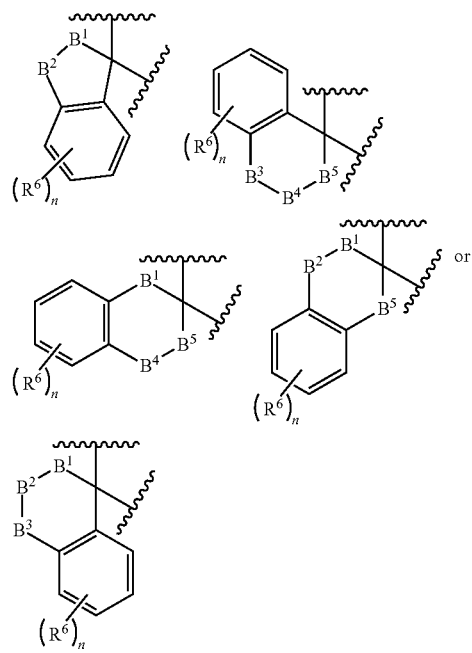

Another preferred embodiment of ring B is a group represented by formula:

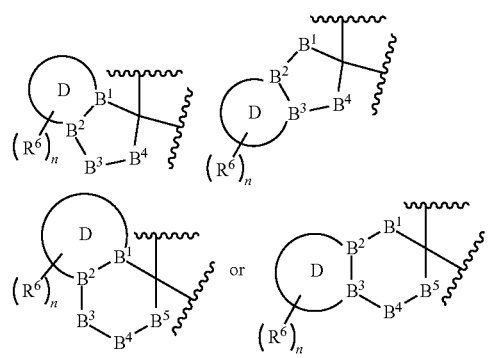

and further preferably includes a group represented by formula:

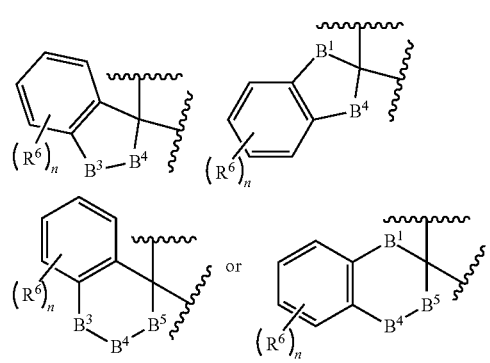

Another preferred embodiment of ring B is a group represented by formula:

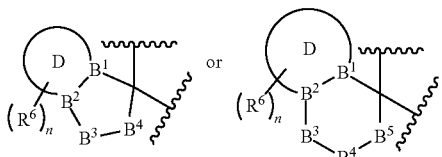

further preferably includes a group represented by formula:

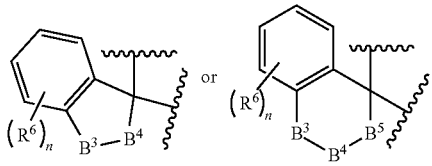

and particularly preferably includes a group represented by formula:

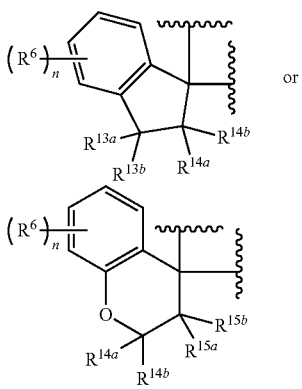

Another preferred embodiment of ring B is a group represented by formula:

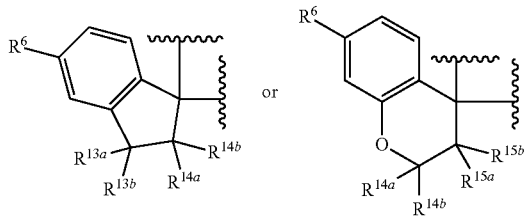

further preferably includes a group represented by formula:

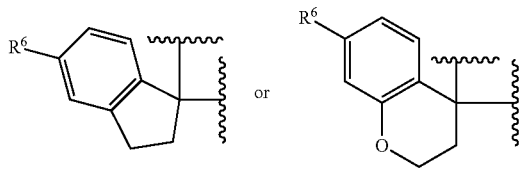

Another preferred embodiment of ring B is a group represented by formula:

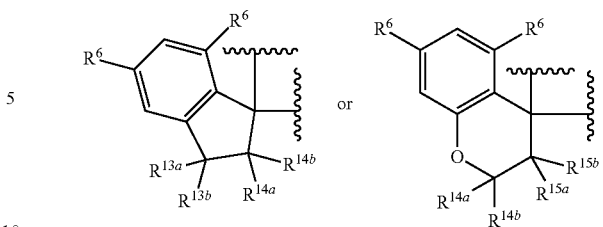

further preferably includes a group represented by formula:

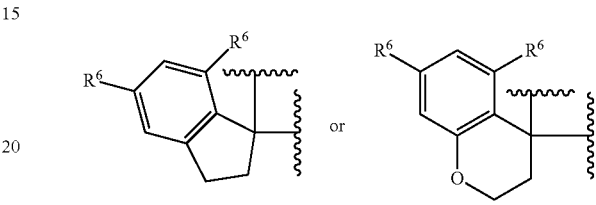

In yet another aspect of ring B is a group represented by formula:

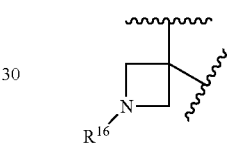

Ring D includes an aromatic carbocycle, a non-aromatic carbocycle, an aromatic heterocycle, or a non-aromatic heterocycle.

A preferred embodiment of ring D is an aromatic carbocycle.

$B^1$ includes $CR^{11a}R^{11b}$, $NR^{11c}$, O, or S.
A preferred embodiment of $B^1$ is $CR^{11a}R^{11b}$.
A more preferred embodiment of $B^1$ is C.
$B^2$ includes $CR^{12a}R^{12b}$, $NR^{12c}$, O, or S.
A preferred embodiment of $B^2$ is $CR^{12a}R^{12b}$.
A more preferred embodiment of $B^2$ is C.
$B^3$ includes $CR^{13a}R^{13b}$, $NR^{13c}$, O, or S.
A preferred embodiment of $B^3$ is $CR^{13a}R^{13b}$, or O.
Specific preferred embodiment of $B^3$ is, for example, $CH_2$, and O.
$B^4$ includes $CR^{14a}R^{14b}$, $NR^{14c}$, O, or S.
A preferred embodiment of $B^4$ is $CR^{14a}R^{14b}$.
A specific preferred embodiment of $B^4$ is $CH_2$, or $CF_2$.
$B^5$ includes $CR^{15a}R^{15b}$, $NR^{15c}$, O, or S.
A preferred embodiment of $B^5$ is $CR^{15a}R^{15b}$.
A specific preferred embodiment of $B^5$ is $CH_2$.
Provided, three or more same atoms in any one of N, O, and S in —$B^1$—$B^2$—$B^3$—$B^4$— or —$B^1$—$B^2$—$B^3$—$B^4$—$B^5$— are not continuously connected like —O—O—O—O—, —S—S—S—S—, or the like.

$R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)—($R^{S1}$)—$R^{S2}$ or a group represented by formula: —S(=N—$R^N$)$_2$—$R^{S1}$.

Here, the group represented by formula: -L-N=S(=O)(—$R^{S1}$)—$R^{S2}$, the group represented by formula: -L-S(=O)(=N—$R^N$)—$R^{S1}$, the group represented by formula: —N=S(=N—$R^N$)(—$R^{S1}$)—$R^{S2}$, and the group represented by formula: —S(=N—$R^N$)$_2$—$R^{S1}$ each have the following chemical structures:

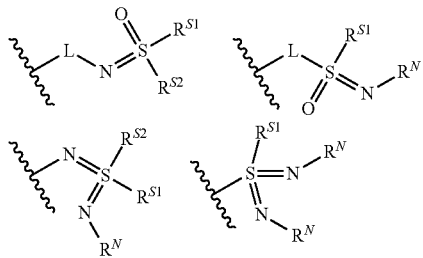

A preferred embodiment of $R^{11a}$, $R^{12a}$, $R^{13a}$, $R^{14a}$, and $R^{15a}$ is each independently hydrogen, halogen, or substituted or unsubstituted alkyl.

A more preferred embodiment of $R^{11a}$, $R^{12a}$, $R^{13a}$, $R^{14a}$, and $R^{15a}$ is each independently hydrogen or halogen.

The substituent in the case that $R^{11a}$, $R^{12a}$, $R^{13a}$, $R^{14a}$, and $R^{15a}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{11b}$, $R^{12b}$, $R^{13b}$, $R^{14b}$ and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$.

A preferred embodiment of $R^{11b}$, $R^{12b}$, $R^{13b}$, $R^{14b}$, and $R^{15b}$ is each independently hydrogen or halogen.

The substituent in the case that $R^{11b}$, $R^{12b}$, $R^{13b}$, $R^{14b}$, and $R^{15b}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{11c}$, $R^{12c}$, $R^{13c}$, $R^{14c}$, and $R^{15c}$ include each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A preferred embodiment of $R^{11c}$, $R^{12c}$, $R^{13c}$, $R^{14c}$, and $R^{15c}$ is each independently hydrogen, halogen, or substituted or unsubstituted alkyl.

A more preferred embodiment of $R^{11c}$, $R^{12c}$, $R^{13c}$, $R^{14c}$, and $R^{15c}$ is hydrogen.

The substituent in the case that $R^{11c}$, $R^{12c}$, $R^{13c}$, $R^{14c}$, and $R^{15c}$ are substituted is each independently halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{11a}$ and $R^{12a}$, $R^{12a}$ and $R^{13a}$, $R^{13a}$ and $R^{14a}$, and/or $R^{14a}$ and $R^{15a}$ may be taken together with adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and/or, $R^{11c}$ and $R^{12a}$, $R^{11c}$ and $R^{12c}$, $R^{12c}$ and $R^{11a}$, $R^{12c}$ and $R^{13a}$, $R^{12c}$ and $R^{13c}$, $R^{13c}$ and $R^{12a}$, $R^{13c}$ and $R^{14a}$, $R^{13c}$ and $R^{14c}$, $R^{14c}$ and $R^{13a}$, $R^{14c}$ and $R^{15a}$, $R^{14c}$ and $R^{15c}$, and/or, $R^{15c}$ and $R^{14a}$ may be taken together with adjacent atoms to form a substituted or unsubstituted aromatic heterocycle or a substituted or unsubstituted non-aromatic heterocycle, and/or, $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$ may be taken together to form a C2-C4 bridge optionally containing heteroatom(s), and/or, $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ may be taken together to form a bond.

n includes an integer of 1 to 4.

A preferred embodiment of n is an integer of 1 to 3.

A more preferred embodiment of n is 1 or 2.

$R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or, $R^{S1}$ and $R^{S2}$ bonding to the same sulfur atom may be taken together with the sulfur atom to form a substituted or unsubstituted non-aromatic heterocycle.

A preferred embodiment of $R^{S1}$ and $R^{S2}$ is each independently hydrogen or substituted or unsubstituted alkyl.

A more preferred embodiment of $R^{S1}$ and $R^{S2}$ is hydrogen.

Examples of the substituent in the case that $R^{S1}$ and $R^{S2}$ are substituted include each independently halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

$R^N$ includes each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl.

A preferred embodiment of $R^N$ is each independently hydrogen or substituted or unsubstituted alkyl.

A more preferred embodiment of $R^N$ is each independently substituted or unsubstituted alkyl.

Examples of the substituent in the case that $R^N$ is substituted each independently include halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

L includes each independently a single bond, alkylene, or C(=O).

A preferred embodiment of L is each independently a single bond or alkylene.

A more preferred embodiment of L is a single bond.

m includes an integer of 1 to 5.

A preferred embodiment of m is an integer of 1 to 3.

A more preferred embodiment of m is 1 or 2.

Ring C includes an aromatic carbocycle, an aromatic heterocycle, a non-aromatic carbocycle, or a non-aromatic heterocycle.

A preferred embodiment of ring C is an aromatic carbocycle or an aromatic heterocycle.

A more preferred embodiment of ring C is benzene, naphthalene, indane, pyridine, pyrimidine, pyrazole, piperidine, piperazine, benzodioxole, benzothiophene, or thiazole.

A more preferred embodiment of ring C is benzene or pyridine.

A particularly preferred embodiment of ring C is benzene.

$R^5$ includes each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$.

A preferred embodiment of $R^5$ is each independently halogen, cyano, substituted or unsubstituted carbamoyl, substituted or unsubstituted amino, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A more preferred embodiment of $R^5$ is each independently halogen, cyano, substituted or unsubstituted amino, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A still more preferred embodiment of $R^5$ is each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

A particularly preferred embodiment of $R^5$ is halogen, substituted or unsubstituted alkyl, substituted or unsubstituted alkyloxy, substituted or unsubstituted non-aromatic carbocyclyl, or substituted or unsubstituted non-aromatic heterocyclyl.

Examples of the substituent in the case that $R^5$ is substituted include halogen, alkyl, haloalkyl, cyanoalkyl, alkyloxyalkyl, haloalkylcarbonyl, non-aromatic carbocyclyl, non-aromatic heterocyclyl, non-aromatic carbocyclylalkyl, aromatic heterocyclylalkyl, or non-aromatic heterocyclylalkyl.

$R^{3a}$ includes hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, or unsubstituted non-aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl.

A preferred embodiment of $R^{3a}$ is hydrogen.

Examples of the substituent in the case that $R^{3a}$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{3b}$ includes hydrogen, halogen, hydroxy, cyano, substituted or unsubstituted alkyl, substituted or unsubstituted alkyloxy, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic heterocyclyl, substituted or unsubstituted aromatic carbocyclyl oxy, substituted or unsubstituted non-aromatic carbocyclyl oxy, substituted or unsubstituted aromatic heterocyclyl oxy, substituted or unsubstituted non-aromatic heterocyclyl oxy, substituted or unsubstituted aromatic carbocyclyl sulfonyl, substituted or unsubstituted non-aromatic carbocyclyl sulfonyl, substituted or unsubstituted aromatic heterocyclyl sulfonyl, or substituted or unsubstituted non-aromatic heterocyclyl sulfonyl.

A preferred embodiment of $R^{3b}$ is hydrogen.

Examples of the substituent in the case that $R^{3b}$ is substituted include halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{4a}$ includes a group represented by formula:

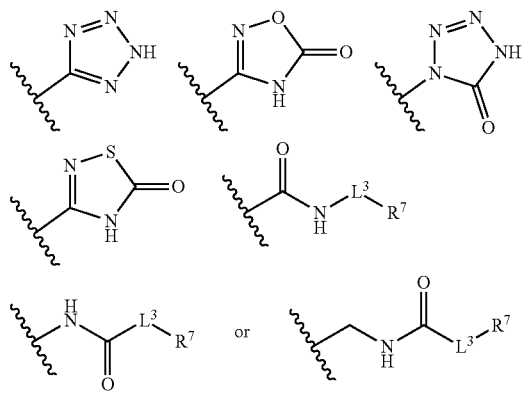

A more preferred embodiment of $R^{4a}$ is

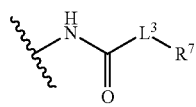

$R^{4b}$ includes halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—$R^{S1}$)—$R^{S2}$, a group represented by formula: -L-S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$-$R^{S1}$.

A preferred embodiment of $R^{4b}$ is substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

A more preferred embodiment of $R^{4b}$ is substituted or unsubstituted alkyl, substituted or unsubstituted aromatic carbocyclyl, or substituted or unsubstituted aromatic heterocyclyl.

Examples of the substituent in the case that $R^{4b}$ is substituted include halogen, hydroxy, cyano, alkyl, alkenyl, haloalkyl, hydroxyalkyl, alkyloxy, haloalkyloxy, alkylsulfonyl, dialkylamino, an aromatic carbocyclyl optionally substituted with Substituent Group B, a non-aromatic carbocyclyl optionally substituted with Substituent Group B, an aromatic heterocyclyl optionally substituted with Substituent Group B, and a non-aromatic heterocyclyl optionally substituted with Substituent Group B.

Preferred substituents in the case that $R^{4b}$ is substituted include halogen, cyano, alkyl, haloalkyl, hydroxyalkyl, alkyloxy, haloalkyloxy, alkylsulfoyl, an aromatic carbocyclyl optionally substituted with Substituent Group B, a non-aromatic carbocyclyl optionally substituted with Substituent Group B, an aromatic heterocyclyl optionally substituted with Substituent Group B, a non-aromatic heterocyclyl optionally substituted with Substituent Group B, aromatic carbocyclyloxy optionally substituted with Substituent Group B, non-aromatic carbocyclyloxy optionally substituted with Substituent Group B, aromatic heterocyclyloxy optionally substituted with Substituent Group B, and non-aromatic heterocyclyloxy optionally substituted with Substituent Group B.

L³ includes a single bond or substituted or unsubstituted alkylene.

A preferred embodiment of L³ is a single bond, unsubstituted alkylene, or alkylene substituted with halogen.

A specific preferred embodiment of L³ is a single bond, methylene, or a group represented by formula:

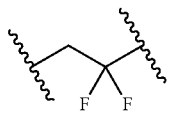 [SMILES: *CC(*)(F)F]

R⁷ includes hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —N=S(=O)(—R$^{S1}$)—R$^{S2}$, a group represented by formula: —S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$.

A preferred embodiment of R⁷ is halogen, substituted or unsubstituted sulfamoyl, substituted or unsubstituted alkyloxy, substituted or unsubstituted alkylsulfonyl, substituted or unsubstituted aromatic heterocyclyl, substituted or unsubstituted non-aromatic heterocyclyl, or a group represented by formula: —S(=O)(=N—R$^N$)—R$^{S1}$.

Examples of the substituent in the case that R⁷ is substituted include oxo, halogen, cyano, hydroxy, alkyl, haloalkyl, alkyloxy, haloalkyloxy, hydroxyalkyl, alkylcarbonyl, or alkylsulfonyl.

R⁶s include each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: -L-N=S(=O)(—R$^{S1}$)—R$^{S2}$, a group represented by formula: -L-S(=O)(=N—R$^N$)—R$^{S1}$, a group represented by formula: —N=S(=N—R$^N$)—(R$^{S1}$)—R$^{S2}$ or a group represented by formula: —S(=N—R$^N$)$_2$—R$^{S1}$.

A preferred embodiment of R$^6$ is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

A more preferred embodiment of R$^6$ is each independently halogen, or substituted or unsubstituted alkyloxy.

A more preferred embodiment of R$^6$ is each independently, halogen, or haloalkyloxy.

Examples of the substituent in the case that R$^6$ is substituted include halogen, alkyl, haloalkyl, cyanoalkyl, hydroxyalkyl, alkyloxy, haloalkyloxy, alkyloxyalkyl, haloalkylcarbonyl, alkyloxycarbonylalkyl, aromatic carbocyclyl optionally substituted with Substituent Group B, non-aromatic carbocyclyl optionally substituted with Substituent Group B, aromatic heterocyclyl optionally substituted with Substituent Group B, non-aromatic heterocyclyl optionally substituted with Substituent Group B, aromatic carbocyclyloxy optionally substituted with Substituent Group B, non-aromatic carbocyclyloxy optionally substituted with Substituent Group B, aromatic heterocyclyloxy optionally substituted with Substituent Group B, and non-aromatic heterocyclyloxy optionally substituted with Substituent Group B.

R$^{16}$ includes each independently hydrogen, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, or the like.

A preferred embodiment of R$^{16}$ is substituted or unsubstituted alkyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl.

A preferred embodiment of R$^{16}$ is substituted or unsubstituted alkyl, aromatic carbocyclyl optionally substituted with Substituent Group B, non-aromatic carbocyclyl optionally substituted with Substituent Group B, aromatic heterocyclyl optionally substituted with Substituent Group B, non-aromatic heterocyclyl optionally substituted with Substituent Group B, aromatic carbocyclylcarbonyl optionally substituted with Substituent Group B, non-aromatic carbocyclylcarbonyl optionally substituted with Substituent Group B, aromatic heterocyclylcarbonyl optionally substituted with Substituent Group B, or non-aromatic heterocyclylcarbonyl optionally substituted with Substituent Group B.

A particularly preferred embodiment of R$^{16}$ is aromatic carbocyclyl optionally substituted with Substituent Group B.

Examples of the substituent in the case that R$^{16}$ is substituted include halogen, alkyl, haloalkyl, aromatic carbocyclyl optionally substituted with Substituent Group B, non-aromatic carbocyclyl optionally substituted with Substituent Group B, aromatic heterocyclyl optionally substituted with Substituent Group B, and non-aromatic heterocyclyl optionally substituted with Substituent Group B.

A feature of the compound according to the present invention is that it has MGAT2 inhibitory activity by forming into a dihydropyrazolopyrazinone derivative represented by formula (I). Moreover, another feature is that the dihydropyrazolopyrazinone derivative represented by formula (I) has a structure in which a pyrazole ring is condensed with a dihydropyrazinone ring, and an enone structure can be avoided and toxicity can be suppressed. Further, a feature of the dihydropyrazolopyrazinone derivative represented by formula (I) is that it has high solubility and metabolic stability, and high stability in an acidic solution.

The compounds represented by formula (I) are not limited to specific isomers but includes all possible isomers (e.g., keto-enol isomers, imine-enamine isomers, diastereoisomers, enantiomers, rotamers or the like), racemates or mixtures thereof.

One or more hydrogen, carbon and/or other atoms in the compounds represented by formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by formula (I) also includes the compounds replaced with these isotopes. The compounds replaced with the isotopes are useful as medicines and include all of radiolabeled compounds of the compound represented by formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds represented by formula (I) can be prepared using well-known methods in the art. For example, a tritium-labeled compound represented by formula (I) can be prepared by introducing a tritium to a certain compound represented by formula (I), through a catalytic dehalogenation reaction using a tritium. This method includes reacting a suitably halogen-substituted precursor of the compound represented by the formula (I) with tritium gas in the presence of a suitable catalyst such as Pd/C, in the presence or absence of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by formula (I) include, for example, salts of the compounds represented by formula (I) with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by formula (I) of the present invention or pharmaceutically acceptable salts thereof may form a solvate (e.g., a hydrate), a cocrystal and/or a crystal polymorph. The present invention also encompasses such various solvates, cocrystals and crystal polymorphs. The "solvate" may be one wherein any number of solvent molecules (e.g., water molecules or the like) is coordinated with the compounds represented by formula (I). When the compounds represented by formula (I) or pharmaceutically acceptable salts thereof are allowed to stand in the atmosphere, the compounds may absorb water, resulting in attachment of adsorbed water or formation of hydrates. Recrystallization of the compounds represented by formula (I) or pharmaceutically acceptable salts thereof may produce a crystal polymorph. The "cocrystal" means that the compounds represented by formula (I) or salts thereof and a counter molecule are present in the same crystal lattice, and a cocrystal with any number of counter molecules may be formed.

The compounds represented by formula (I) of the present invention or pharmaceutically acceptable salt thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by formula (I) through enzymatic oxidation, reduction, hydrolysis or the like under physiological conditions and in vivo, compounds that are converted to the compounds represented by formula (I) through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by formula (I) or pharmaceutically acceptable salt thereof has hydroxy group (s), prodrugs include acyloxy derivatives and sulfonyloxy derivatives that are prepared by, for example, reacting compounds having hydroxy group(s) with suitable acyl halide, suitable acid anhydride, suitable sulfonyl chloride, suitable sulfonyl anhydride and mixed anhydride, or with a condensing agent. Examples include $CH_3COO-$, $C_2H_5COO-$, tert-BuCOO—. $C_{15}H_{31}COO-$, PhCOO—, (m-NaOOCPh)COO—, NaOOCCH$_2$CH$_2$COO—, CH$_3$CH (NH$_2$)COO—, CH$_2$N(CH$_3$)$_2$COO—, CH$_3$SO$_3$—, CH$_3$CH$_2$SO$_3$—, CF$_3$SO$_3$—, CH$_2$FSO$_3$—, CF$_3$CH$_2$SO$_3$—, p-CH$_3$O—PhSO$_3$—, PhSO$_3$— and p-CH$_3$PhSO$_3$—.

(Production Method for Compound of the Present Invention)

For example, the compound represented by formula (I) according to the present invention can be prepared by the general procedure described below. In extraction, purification, and other operations, any process commonly performed therefor in organic chemistry experiments can be employed.

The compound of the present invention can be synthesized in accordance with a method known in the art.

(General Procedure)

The compound represented by formula (I) according to the present invention (a17 below) can be produced, for example, through the following production method.

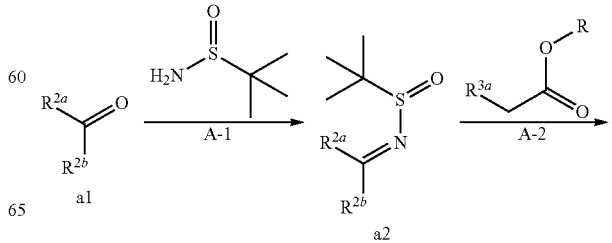

-continued

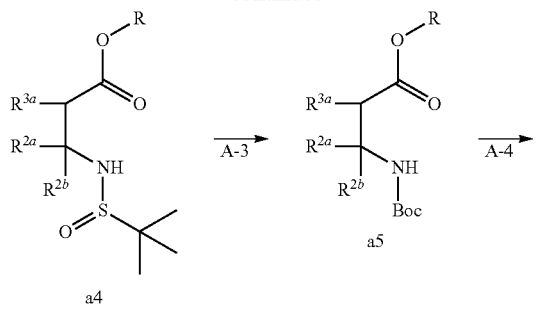

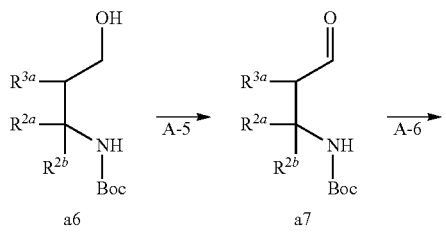

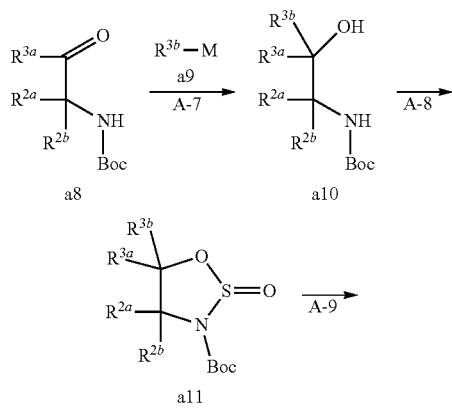

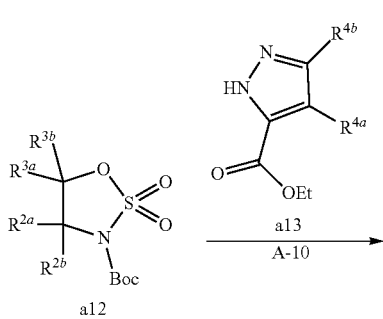

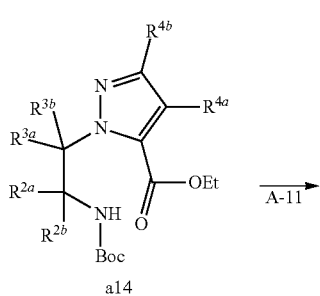

-continued

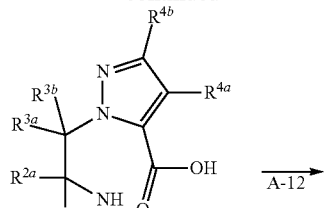

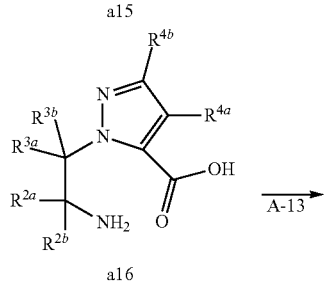

wherein each symbol is as described in above.

Step A-1

Compound a2 can be obtained by reacting Compound a1 with tert-butylsulfinamide with tetraisopropoxytitanium, tetraethoxyethane, or the like.

The reaction temperature is 20° C. to 120° C., and preferably 70° C. to 100° C.

The reaction time is 1 hour to 12 hours, and preferably 3 hours to 6 hours.

As the reaction solvent, tetrahydrofuran, 2-methyltetrahydrofuran, and toluene are exemplified.

Step A-2

After reacting a base such as lithium diisopropylamide or lithium hexamethyldisilazide with a3, as necessary, titanium chloride triisopropoxide or the like is added thereto and reacted with Compound a2 to obtain Compound a4.

As R in Compound a3, methyl, ethyl, and tert-butyl are exemplified.

The reaction temperature is −78° C. to −20° C. for a reaction between the base such as lithium diisopropylamide or lithium hexamethyldisilazide with ester a3, and a subsequent reaction with Compound a2.

The reaction time between the base and ester a3 is 30 minutes to 2 hours, and a subsequent reaction with Compound a2 is 1 to 5 hours.

As the reaction solvent, tetrahydrofuran and diethyl ether are exemplified.

Step A-3

Compound a5 can be obtained by reacting Compound a4 with an acid or Lewis acid and then reacting with Boc₂O in the presence of a base.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3$ ($Et_2O$) are exemplified. 1 to 10 molar equivalents of the acid or Lewis acid with respect to Compound a4 can be used.

As the base, sodium hydroxide, sodium carbonate, sodium bicarbonate, potassium carbonate, calcium carbonate, cesium carbonate, pyridine, and triethylamine are exemplified, and 3 to 15 molar equivalents with respect to Compound a4 can be used.

The reaction temperature is 0° C. to 60° C., and preferably 0° C. to 20° C.

The reaction time is 0.5 hour to 24 hours, and preferably 6 hours to 18 hours.

As the reaction solvent, methanol, ethanol, water, acetone, acetonitrile, and DMF are exemplified, and these reaction solvents can be used alone or in combination.

Step A-4

Compound a5 can be obtained by reacting Compound a6 with a reducing agent.

As the reducing agent, lithium borohydride and lithium aluminum hydride are exemplified. 1 to 10 molar equivalents of the reducing agent with respect to Compound a5 can be used.

The reaction temperature is 0° C. to the reflux temperature, preferably 20° C. to the reflux temperature.

The reaction time is 0.2 hour to 48 hours, and preferably 1 hour to 24 hours.

As the reaction solvent, methanol, ethanol, propanol, isopropanol, butanol, tetrahydrofuran, diethyl ether, dichloromethane, and water are exemplified, and these reaction solvents can be used alone or in combination.

Step A-5

Compound a7 can be obtained by reacting Compound a6 with an oxidizing agent such as 2-iodoxybenzoic acid or dess-martin periodinane.

The reaction temperature is −10° C. to 50° C., and preferably 0° C. to 30° C.

The reaction time is 1 hour to 24 hours, and preferably 5 hours to 20 hours.

As the reaction solvent, dimethyl sulfoxide or the like can be used.

Step A-6

Compound a8 can be obtained by reacting Compound a7 with osmium tetroxide, 4-methylmorpholine, 4-methylmorpholine N-oxide, sodium periodate, and the like.

The reaction temperature is −10° C. to 50° C., and preferably 0° C. to 30° C.

The reaction time is 1 hour to 24 hours, and preferably 5 hours to 20 hours.

As the reaction solvent, a mixed solvent of acetone and water or the like can be used.

Step A-7

Compound a10 can be obtained by reacting Compound a8 with nucleophile a9.

Examples of the nucleophile a9 include lithium reagent such as methyllithium, ethyllithium, etc., Grignard reagent such as methylmagnesium bromide, methylmagnesium chloride, methylmagnesium iodide, ethylmagnesium bromide, ethylmagnesium chloride, ethylmagnesium iodide, etc., and its mixed reagent of metallic salt thereof, and 1 to 5 molar equivalents with respect to Compound a8 can be used.

The reaction temperature is −78° C. to the reflux temperature of the solvent, preferably −45° C. to 0° C.

The reaction time is 0.5 to 24 hours, preferably 1 hour to 6 hours.

As the reaction solvent, tetrahydrofuran, hexane, diethylether, methyl tert-butyl ether, toluene, dichloromethane, and methanol are exemplified, and these reaction solvents can be used alone or in combination.

The nucleophile a9 can be prepared by lithiation of a halide with an alkyl lithium such as n-butyllithium.

The reaction solvent is not particularly limited as long as it is not a solvent such as tetrahydrofuran and dioxane not reacting with alkyllithium. The lithiation temperature is preferably about −78° C. to 0° C.

A compound in which $R^{3b}$ is hydrogen can be obtained by allowing a reducing agent, such as sodium borohydride, lithium borohydride, or lithium aluminum hydride, to act instead of the nucleophile a9.

Step A-8

Compound a11 can be obtained by reacting Compound a10 with thionyl chloride and a base.

As the base, pyridine, triethylamine and diisopropylethylamine are exemplified, and 1 to 5 molar equivalents with respect to Compound a10 can be used.

The reaction temperature is −10° C. to 50° C., and preferably 0° C. to 30° C.

The reaction time is 1 hour to 24 hours, and preferably 5 hours to 10 hours.

As the reaction solvent, acetonitrile, dioxane, tetrahydrofuran, DMF or the like can be used.

Step A-9

Compound a12 can be obtained by reacting Compound a11 with ruthenium chloride hydrate, sodium periodate and the like.

The reaction temperature is −10° C. to 50° C., and preferably 0° C. to 30° C.

The reaction time is 1 hour to 24 hours, and preferably 5 hours to 20 hours.

As the reaction solvent, a mixed solvent of ethyl acetate and water or the like can be used.

Step A-10

Compound a14 can be obtained by reacting Compound a12, Compound a13, and a base.

As the base, sodium hydroxide, sodium carbonate, sodium bicarbonate, potassium carbonate, calcium carbonate, cesium carbonate, pyridine, and triethylamine are exemplified, and 1 to 5 molar equivalents of the base with respect to Compound a13 can be used.

The reaction temperature is 0° C. to 150° C., and preferably 50° C. to 100° C.

The reaction time is 0.5 hour to 24 hours, and preferably 1 hour to 5 hours.

As the reaction solvent, methanol, ethanol, acetonitrile, and DMF are exemplified, and these reaction solvents can be used alone or in combination.

Step A-11

Compound a15 can be obtained by reacting Compound a14 with a base.

As the base, sodium hydroxide, potassium hydroxide, and sodium hydride are exemplified, and 1 to 5 molar equivalents with respect to Compound a14 can be used.

The reaction temperature is 0° C. to 100° C., and preferably 0° C. to 30° C.

The reaction time is 0.5 hour to 24 hours, and preferably 1 hour to 5 hours.

As the reaction solvent, methanol, ethanol, acetonitrile, water, and DMF are exemplified, and these reaction solvents can be used alone or in combination.

Step A-12

Compound a16 can be obtained by reacting Compound a15 with an acid or Lewis acid.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3$ ($Et_2O$) are exemplified. 1 to 50 molar equivalents of the acid or Lewis acid with respect to Compound a15 can be used.

The reaction temperature is 0° C. to 60° C., and preferably 0° C. to 20° C.

The reaction time is 0.5 hour to 24 hours, and preferably 6 hours to 18 hours.

As the reaction solvent, ethyl acetate, methanol, ethanol, water, acetone, acetonitrile, and DMF are exemplified, and these reaction solvents can be used alone or in combination.

Step A-13

Compound a17 can be obtained by reacting Compound a16 with a condensing agent and a base.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a16 can be used.

As the base, triethylamine and diisopropylethylamine are exemplified, and 1 to 5 molar equivalents with respect to Compound a16 can be used.

The reaction temperature is −20° C. to 60° C., and preferably 0° C. to 30° C.

The reaction time is 0.1 hour to 24 hours, and preferably 1 hour to 5 hours.

As the reaction solvent, DMF, DMA, NMP, tetrahydrofuran, dioxane, dichloromethane, and acetonitrile are exemplified, and these reaction solvents can be used alone or in combination.

The compounds of the present invention have MGAT2 inhibitory activity, and are useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

The compounds of the present invention have not only MGAT2 inhibitory activity but also usefulness as a medicine, and have any or all of the following superior features:
a) having high metabolic stability,
b) exhibiting high solubility,
c) having less risk of phototoxicity,
d) having less risk of hepatotoxicity,
e) having less risk of kidney toxicity,
f) having less risk of cardiovascular toxicity,
g) having less risk of gastrointestinal disorders,
h) having less risk of drug interaction,
i) having high oral absorbability,
j) having small clearance,
k) having high distribution to a targeted tissue,
l) having intense enzymatic activity,
m) causing less induction of drug-metabolizing enzyme,
n) having intense efficacy,
o) having high selectivity of MGAT2 inhibitory activity, and
p) having high chemical stability.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, and inner ear or vaginal administration.

In the case of oral administration, any forms, which are usually used, such as oral solid formulations (e.g., tablets, powders, granules, capsules, pills, or films), and oral liquid formulations (e.g., suspension, emulsion, elixir, syrup, lemonade, spirit, aromatic water, extract, decoction, or tincture) may prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, and external preparations (e.g., ophthalmic drops, nasal drops, ear drops, aerosols, inhalations, lotion, infusion, liniment, mouthwash, enema, ointment, plaster, jelly, cream, patch, cataplasm, external powder, or suppository) can be preferably administered. Injections can be emulsions whose type is O/W, W/G, O/W/O, W/G/W or the like.

The pharmaceutical composition may be manufactured by mixing an effective amount of the compound of the present invention with various pharmaceutical additives suitable for formulation, such as excipients, binders, disintegrants, lubricants, and diluents. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of the pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

The dose for co-administered drugs may be appropriately selected in reference to the clinical dose. The compounding ratio of the compounds of the present invention and co-administered drugs may be appropriately selected depending on the subject to be treated, administration route, disease to be treated, symptoms, combination of the drugs and the like. For administration in humans, for example, 1 part by weight of the compounds of the present invention may be used in combination with 0.01 to 100 parts by weight of co-administered drugs.

The pharmaceutical composition of the present invention is also effective for obesity (however, only when there are both type 2 diabetes and dyslipidemia and BMI is 25 kg/m$^2$ or greater even if diet therapy/exercise therapy is performed).

The pharmaceutical composition of the present invention is also effective for severe obesity for which the effect of diet therapy and exercise therapy applied in advance is insufficient.

The pharmaceutical composition of the present invention can be used in combination with other anti-obesity agent(s) (the pharmaceutical composition comprising compounds having anti-obesity effect, or the medicinal agent for obesity or for the weight management for obesity). For example, a combination treatment with a pharmaceutical composition comprising a compound having an anti-obesity effect and the compound of the present invention can be used for the prevention and/or treatment of obesity or the weight management for obesity. A combination treatment with the pharmaceutical composition comprising the compound of the present invention and a pharmaceutical composition(s) comprising a compound having an anti-obesity effect can be used for the prevention and/or treatment of obesity or the weight management for obesity. Furthermore, a method of treatment by administering the pharmaceutical composition of the invention can be used in combination of the diet therapy, drug therapy, exercise and the like.

In this description, meanings of each abbreviation are as follows:

Boc: tert-butoxycarbonyl
DMA: Dimethylacetamide
DMF: N,N-dimethylformamide
DMSO: Dimethylsulfoxide
EDC: 1-ethyl-3-(3-dimethylaminopropyl)-carbodiimide
Et: Ethyl
HATU: 0-(7-Azabenzotriazol-1-yl)-1,1,3,3-tetramethyluronium hexafluorophosphate
NMP: N-methylpyrrolidone The present invention will be described in more detail with reference to, but not limited to, the following Examples and Test Examples.

NMR spectrum data of the compound of the present invention and its intermediate was shown. NMR analysis obtained in each example was conducted at 400 MHz, and the measurement was performed using deuterated chloroform (CDCl$_3$) or dimethyl sulfoxide (d6-DMSO).

Example 1

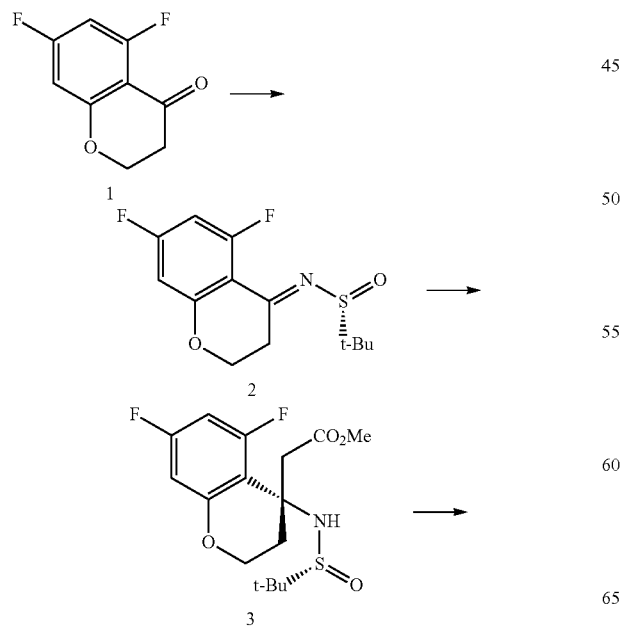

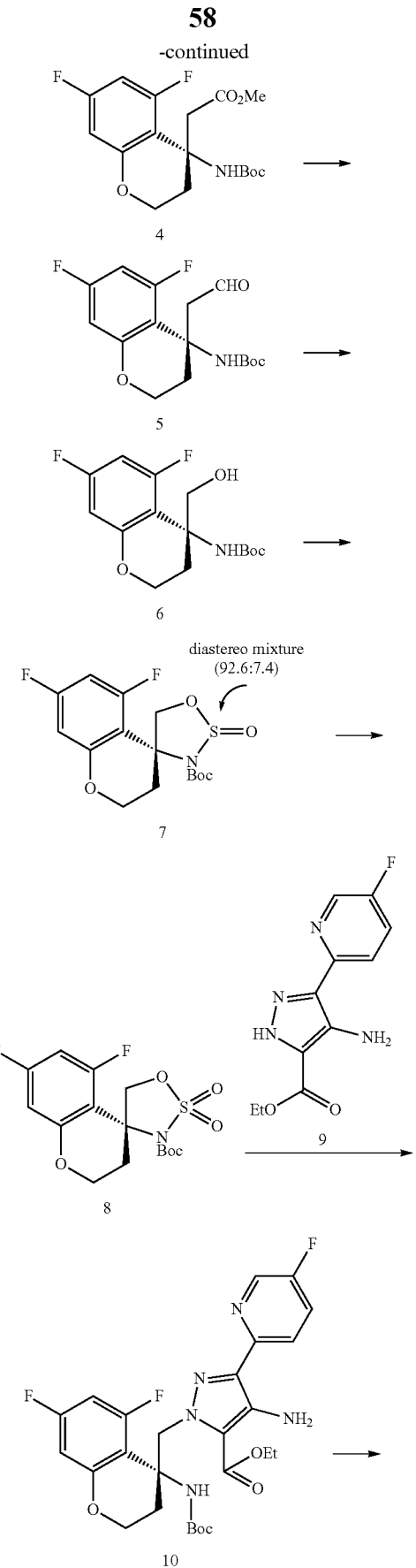

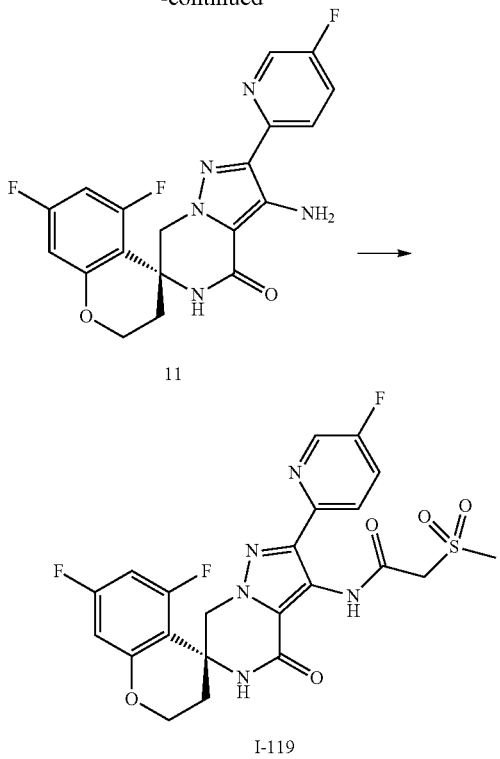

Step 1 Synthesis of Compound 2

(R)-2-Methylpropane-2-sulfinamide (631 mg, 5.21 mmol) was dissolved in toluene (2.5 mL), and tetraethoxytitanium (0.654 mL, 3.12 mmol) was added. Thereafter, known compound 1 (384 mg, 2.08 mmol) was dissolved in toluene (2.5 mL), and added. The mixture was stirred at 100° C. for 3 hours. Then, an aqueous citric acid solution and ethyl acetate were added thereto at room temperature, and insoluble matter was filtered, followed by extraction with ethyl acetate. The organic layer was washed with saturated sodium chloride solution, and then dried over anhydrous magnesium sulfate. The solvent was evaporated under reduced pressure, and the obtained residue was purified by silica gel column chromatography (hexane-ethyl acetate) to give Compound 2 (428 mg, yield 72%).

$^1$H-NMR (CDCl$_3$) δ: 1.32 (s, 9H), 3.31-3.38 (m, 1H), 3.45-3.52 (m, 1H), 4.27-4.33 (m, 1H), 4.36-4.41 (m, 1H), 6.43-6.49 (m, 2H).

Step 2 Synthesis of Compound 3

To a lithium hexamethyldisilazide 1 M tetrahydrofuran solution (2.23 mL, 2.23 mmol), tetrahydrofuran (1 mL) and methyl acetate (0.178 mL, 2.23 mmol) were added at −78° C. and stirred for 1 hour. Thereafter, a titanium chloride triisopropoxide 1 M hexane solution (2.98 mL, 2.98 mmol) was added dropwise at −78° C., and the mixture was stirred for 30 minutes. Then, Compound 2 (428 mg, 1.49 mmol) was dissolved in tetrahydrofuran (1 mL) and added dropwise at −78° C., and the mixture was stirred for 4 hours. Thereafter, a 10% aqueous citric acid solution and Rochelle salt were added, and the mixture was warmed to room temperature and stirred for 12 hours. Then, the mixture was extracted with ethyl acetate, the organic layer was washed with saturated sodium bicarbonate water and saturated sodium chloride solution, and then dried over anhydrous magnesium sulfate. The solvent was evaporated under reduced pressure, and the obtained residue was purified by silica gel column chromatography (hexane-ethyl acetate) to give Compound 3 (305 mg, yield 57%).

$^1$H-NMR (CDCl$_3$) δ: 1.22 (s, 9H), 2.19-2.27 (m, 1H), 2.45-2.49 (m, 1H), 2.74 (d, J=15.9 Hz, 1H), 3.40 (d, J=15.9 Hz, 1H), 3.70 (s, 3H), 4.19-4.24 (m, 1H), 4.51-4.57 (m, 1H), 5.02 (s, 1H), 6.36-6.47 (m, 2H).

Step 3 Synthesis of Compound 4

Compound 3 (2.31 g, 6.40 mmol) was dissolved in methanol (18.5 mL), a 4 mol/L dioxane hydrochloride solution (3.20 mL, 12.8 mmol) was added, and the mixture was stirred at room temperature for 1 hour and 15 minutes. The mixture was diluted with water (9.3 mL), sodium hydrogen carbonate (1.61 g, 19.2 mmol) and di-tert-butyl dicarbonate (2.79 g, 12.8 mmol) were added, and the mixture was further stirred at room temperature for 18 hours. The reaction solution was concentrated under reduced pressure and azeotropically dehydrated with ethyl acetate, then diluted with ethyl acetate, and insoluble matter was filtered. The solvent was evaporated under reduced pressure, and the obtained residue was purified by silica gel column chromatography (hexane-ethyl acetate, silica gel) to give Compound 4 (1.85 g, purity 96.1%, yield 78%).

$^1$H-NMR (CDCl$_3$) δ: 6.42-6.33 (2H, m), 5.50 (1H, s), 4.27-4.13 (2H, m), 3.64 (3H, s), 3.37-3.30 (1H, m), 3.04 (1H, d, J=14.6 Hz), 2.91-2.82 (1H, m), 2.27-2.18 (1H, m), 1.38 (9H, br s).

Step 4 Synthesis of Compound 5

Compound 4 (1.85 g, 4.97 mmol) was dissolved in tetrahydrofuran (9.3 mL), a 1 mol/L tetrahydrofuran solution (2.50 ml, 2.50 mmol) of lithium borohydride was added at −78° C., and the mixture was stirred at room temperature for 18.5 hours. The reaction solution was added with ice, added with a 2 mol/L aqueous solution of hydrochloric acid to adjust the pH to 4, and extracted with ethyl acetate. The solvent was evaporated under reduced pressure, the obtained residue was dissolved in dimethyl sulfoxide (9.1 mL), 2-iodoxybenzoic acid (2.09 g, 7.46 mmol) was added, and the mixture was stirred at room temperature for 19.5 hours. Thereafter, 2-iodoxybenzoic acid (0.418 g, 1.41 mmol) was further added, and the mixture was stirred for 4 hours. Ethyl acetate and water were added to the reaction solution, precipitated solid was filtered off, the organic layer was washed with water, and the solvent was evaporated under reduced pressure. The obtained residue was purified by silica gel column chromatography (hexane-ethyl acetate, silica gel) to give Compound 5 (1.70 g, purity 94.4%, yield 99%).

$^1$H-NMR (CDCl$_3$) δ: 9.65 (1H, q, J=1.7 Hz), 6.45-6.36 (2H, m), 5.03 (1H, s), 4.23 (1H, tt, J=11.3, 4.0 Hz), 4.18 (1H, td, J=11.3, 2.3 Hz), 3.59-3.51 (1H, m), 3.34 (1H, dt, J=17.1, 1.7 Hz), 2.96-2.88 (1H, m), 2.19 (1H, ddd, J=14.2, 10.9, 4.1 Hz), 1.42 (9H, s).

Step 5 Synthesis of Compound 6

Compound 5 (1.70 g, 4.89 mmol) was dissolved in acetone (30 mL) and water (3 mL), 5% microencapsulated osmium tetroxide (0.889 g, 0.245 mmol), 4-methylmorpholine (1.24 g, 12.2 mmol), 4-methylmorpholine N-oxide (1.15 g, 9.79 mmol) and sodium periodate (6.07 g, 24.5 mmol)

were added, and the mixture was stirred at room temperature for 15 hours. The reaction solution was concentrated under reduced pressure and diluted with ethyl acetate and water, then sodium thiosulfate pentahydrate (6.07 g, 24.5 mmol) was added, insoluble matter was filtered off, the organic layer was washed with water, and the solvent was evaporated under reduced pressure. The obtained residue was dissolved in methanol (12 mL), sodium borohydride (93.0 mg, 2.45 mmol) was added, and the mixture was stirred at room temperature for 20 minutes. The reaction solution was concentrated under reduced pressure, diluted with water, added with a 2 mol/L aqueous solution of hydrochloric acid to adjust the pH to 4, and extracted with ethyl acetate. The organic layer was washed with water, and then the solvent was evaporated under reduced pressure. The obtained residue was purified by silica gel column chromatography (hexane-ethyl acetate, silica gel) to give Compound 6 (1.06 g, yield 68%).

$^1$H-NMR (CDCl$_3$) δ: 6.43-6.37 (2H, m), 5.17 (1H, s), 4.49-4.44 (1H, m), 4.28-4.14 (3H, m), 3.70 (1H, dd, J=11.4, 10.1 Hz), 2.51-2.36 (2H, m), 1.42 (9H, s).

Step 6 Synthesis of Compound 7

A solution of Compound 6 (1.05 g, 3.32 mmol) in acetonitrile (12 mL) was added dropwise to a solution of thionyl chloride (1.22 g, 10.3 mmol) in acetonitrile (10 mL) at −50° C. The mixture was stirred at the same temperature for 1 hour and then added with pyridine (1.05 g, 23.3 mmol), and the mixture was stirred at room temperature for 3 hours. The mixture was diluted with water, and then extracted with ethyl acetate, and washed with water. Thereafter, the solvent was evaporated under reduced pressure, and the obtained residue was purified by silica gel column chromatography (hexane-ethyl acetate, silica gel) to give Compound 7 (1.09 g, purity 91.2%, yield 83%) as a mixture of diastereomer ratio of 92.6:7.4. Both diastereomers were used in next step without separation.

Step 7 Synthesis of Compound 8

Compound 7 (1.08 g, 2.73 mmol) was dissolved in ethyl acetate (10 mL) and water (10 mL), and ruthenium chloride hydrate (3.0 mg, 0.01 mmol) and sodium periodate (642 mg, 3.00 mmol) were added at 0° C. The mixture was stirred at room temperature for 2 hours. At room temperature, water (10 mL) was added, ruthenium chloride hydrate (2.1 mg, 0.01 mmol) and sodium periodate (117 mg, 0.546 mmol) were added, and the mixture was further stirred at room temperature for 3 hours. The mixture was extracted with ethyl acetate and washed with water, then filtered through a column packed with dry silica gel. The filtrate was concentrated under reduced pressure and then powdered with hexane-ethyl acetate to give Compound 8 (873 mg, yield 85%).

$^1$H-NMR (DMSO-D$_6$) δ: 6.93 (1H, ddd, J=11.4, 9.2, 2.7 Hz), 6.72 (1H, dt, J=10.1, 2.0 Hz), 5.09 (1H, d, J=10.2 Hz), 4.63 (1H, dd, J=10.2, 1.0 Hz), 4.42 (1H, ddd, J=12.2, 4.0, 2.6 Hz), 4.22 (1H, td, J=12.4, 2.0 Hz), 2.47-2.32 (2H, m), 1.22 (9H, s).

Step 8 Synthesis of Compound 10

Compound 9 (110 mg, 0.439 mmol) was dissolved in DMF (4 mL), potassium carbonate (60.6 mg, 0.439 mmol) was added thereto, and the mixture was heated to 100° C. Compound 8 (151 mg, 0.399 mmol) was added thereto, and the mixture was stirred at 100° C. for 40 minutes. The mixture was diluted with water, then extracted with ethyl acetate, and washed with water. Thereafter, the solvent was evaporated under reduced pressure, and the obtained residue was purified by silica gel column chromatography (hexane-ethyl acetate, silica gel) to give Compound 10 (151 mg, purity 96.3%, yield 67%).

$^1$H-NMR (CDCl$_3$) δ: 8.42 (1H, d, J=2.8 Hz), 8.01-7.95 (1H, m), 7.46 (1H, td, J=8.5, 2.8 Hz), 6.84 (1H, s), 6.44-6.32 (2H, m), 5.87 (2H, s), 5.15-4.86 (2H, m), 4.44-4.19 (4H, m), 2.68-2.91 (1H, m), 1.90-1.81 (1H, m), 1.42 (3H, t, J=7.2 Hz), 1.32 (9H, br s).

Step 9 Synthesis of Compound 11

Compound 10 (150 mg, 0.439 mmol) was dissolved in DMF (4 mL), 60% sodium hydride (42.3 mg, 1.06 mmol) was added, and the mixture was stirred at room temperature for 1 hour, and diluted with ice. Then, the mixture was added with a 1 mol/L aqueous solution of hydrochloric acid to adjust the pH to 4, and extracted with ethyl acetate. After washing with water, the solvent was concentrated under reduced pressure, 4 mol/L dioxane hydrochloride (4 mL, 16.0 mmol) was added to the obtained residue, and the mixture was stirred at room temperature for 1 hour. The solvent was concentrated under reduced pressure and diluted with DMF (6 mL), 0-(7-azabenzotriazol-1-yl)-N,N,N',N'-tetramethyluronium hexafluorophosphate (151 mg, 0.398 mmol) and triethylamine (0.257 mL, 1.86 mmol) were added, and the mixture was stirred at room temperature for 30 minutes. The mixture was added with water, extracted with ethyl acetate, and washed with water. Thereafter, the solvent was evaporated under reduced pressure, and the obtained residue was purified by silica gel column chromatography (hexane-ethyl acetate, silica gel) to give Compound 11 (59.5 mg, purity 97.4%, yield 55%).

$^1$H-NMR (CDCl$_3$) δ: 8.43 (1H, d, J=2.9 Hz), 7.96 (1H, dd, J=8.9, 4.5 Hz), 7.45 (1H, td, J=8.6, 2.9 Hz), 6.54-6.49 (2H, m), 5.75 (1H, s), 5.68 (2H, s), 4.77 (1H, d, J=13.1 Hz), 4.29-4.19 (3H, m), 2.37-2.21 (2H, m).

Step 10 Synthesis of Compound (I-119)

Compound 11 (30.8 mg, 0.075 mmol) and 2-(methylsulfonyl) acetic acid (20.6 mg, 0.149 mmol) were dissolved in tetrahydrofuran (4 mL), 0-(7-azabenzotriazol-1-yl)-N,N,N',N'-tetramethyluronium hexafluorophosphate (56.8 mg, 0.149 mmol) and triethylamine (0.041 mL, 0.299 mmol) were added, and the mixture was stirred at room temperature for 2 hours. The mixture was added with water, extracted with ethyl acetate, and washed with water. Thereafter, the solvent was evaporated under reduced pressure, and the obtained residue was purified by silica gel column chromatography (chloroform-methanol, amino silica gel) to give Compound I-119 (35.4 mg, purity 97.0%, yield 88%).

$^1$H-NMR (DMSO-D$_6$) δ: 10.07 (1H, s), 8.97 (1H, s), 8.56 (1H, d, J=2.8 Hz), 7.89 (1H, dd, J=8.8, 4.6 Hz), 7.77 (1H, td, J=8.8, 2.8 Hz), 6.91 (1H, ddd, J=11.0, 9.2, 2.2 Hz), 6.74-6.70 (1H, m), 4.76 (1H, d, J=13.6 Hz), 4.71 (1H, d, J=13.6 Hz), 4.39-4.19 (3H, m), 3.17 (3H, s), 2.25-2.19 (1H, m), 2.10-2.02 (1H, m).

Example 2

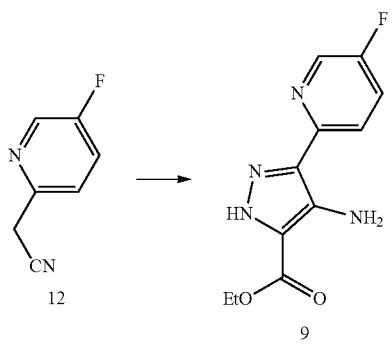 [SMILES: N#CCc1ccc(F)cn1 ; CCOC(=O)c1[nH]nc(-c2ccc(F)cn2)c1N]

Step 1 Synthesis of Compound 9

60% Sodium hydride (314 mg, 7.86 mmol) was added to ethanol (20 mL) at 0° C., and after stirring the mixture for 10 minutes, known Compound 12 (1.00 g, 7.15 mmol) and 88.3% ethyl diazoacetate (1.02 g, 7.86 mmol) were added dropwise, and the mixture was stirred at room temperature for 5 hours. The reaction solution was added with a 2 mol/L aqueous solution of hydrochloric acid at 0° C. to adjust the pH to 8.6, and extracted with ethyl acetate. After washing with water, most of the solvent was evaporated under reduced pressure, and the residue was powdered with hexane-ethyl acetate to give Compound 9 (1.49 g, yield 84%).

$^1$H-NMR (CDCl$_3$) δ: 8.42 (1H, d, J=3.0 Hz), 8.02 (1H, dd, J=8.8, 4.5 Hz), 7.46 (1H, td, J=8.5, 3.0 Hz), 5.66 (2H, br s), 4.42 (2H, q, J=7.2 Hz), 1.43 (3H, t, J=7.2 Hz).

The following compounds were synthesized in the same manner. The physical data of the compounds are shown below.

In the tables, "RT" indicates retention time (minutes) in LC/MS (liquid chromatography/mass spectrometry), "MS" indicates mass (M+H) in LC/MS, and "LCMS Method" indicates any of the following measurement conditions for LC/MS.

[Measurement Condition A]
Column: ACQUITY UPLC (registered trademark) BEH C18 (1.7 μm i.d.2.1×50 mm) (Waters)
Flow rate: 0.55 mL/min
UV detection wavelength: 254 nm
Mobile phase: [A] is 0.1% formic acid in aqueous solution, and [B] is 0.1% formic acid in acetonitrile solution.
Gradient: linear gradient of 5% to 100% solvent [B] for 3 minutes was performed, and then 100% solvent [B] was maintained for 0.5 minute.

[Measurement Condition B]
Column: ACQUITY UPLC (registered trademark) BEH C18 (1.7 μm i.d.2.1×50 mm) (Waters)
Flow rate: 0.8 mL/min
UV detection wavelength: 254 nm
Mobile phase: [A] is 0.1% formic acid in aqueous solution, and [B] is 0.1% formic acid in acetonitrile solution.
Linear gradient of 5% to 100% solvent [B] for 3.5 minutes was performed, and 100% solvent [B] was maintained for 0.5 minute.

[Measurement Condition C]
Column: ACQUITY UPLC (registered trademark) BEH C18 (1.7 μm i.d.2.1×50 mm) (Waters)
Flow rate: 0.8 mL/min
UV detection wavelength: 254 nm
Mobile phase: [A] is 0.1% formic acid in aqueous solution, and [B] is 0.1% formic acid in acetonitrile solution.
Linear gradient of 5% to 100% solvent [B] for 3.5 minutes was performed, and 100% solvent [B] was maintained for 0.5 minute.

[Measurement Condition D]
Column: Shim-pack XR-ODS (2.2 μm, i.d.50×3.0 mm) (Shimadzu)
Flow rate: 1.6 mL/min
UV detection wavelength: 254 nm;
Mobile phase: [A] is 0.1% formic acid in aqueous solution, and [B] is 0.1% formic acid in acetonitrile solution.
Gradient: linear gradient of 10% to 100% solvent [B] for 3 minutes was performed, and 100% solvent [B] was maintained for 0.5 minute.

TABLE 1

| No. | Structure | LCMS method | RT | MS |
|---|---|---|---|---|
| I-1 | 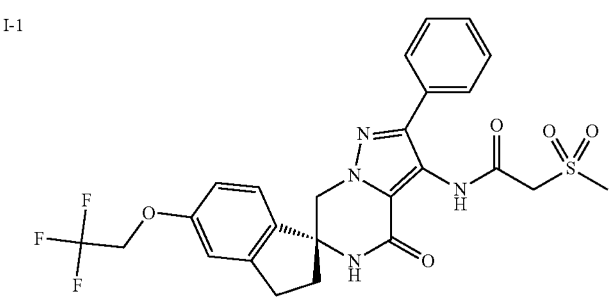 | A | 1.93 | 549.1 |

TABLE 1-continued

| No. | Structure | LCMS method | RT | MS |
|---|---|---|---|---|
| I-2 | 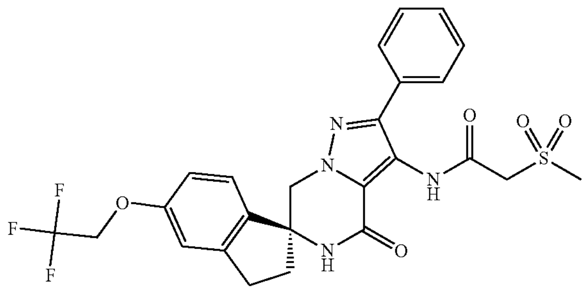 [SMILES: CS(=O)(=O)CC(=O)Nc1c(-c2ccccc2)nn2c1C(=O)N[C@]1(CCc3cc(OCC(F)(F)F)ccc31)C2] | A | 1.93 | 549.1 |
| I-3 | 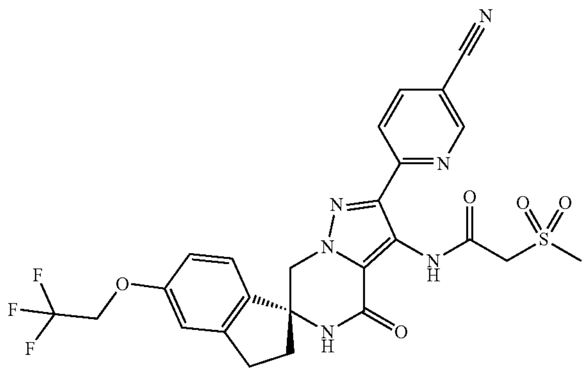 [SMILES: CS(=O)(=O)CC(=O)Nc1c(-c2ccc(C#N)cn2)nn2c1C(=O)N[C@@]1(CCc3cc(OCC(F)(F)F)ccc31)C2] | A | 1.83 | 575.1 |
| I-4 | 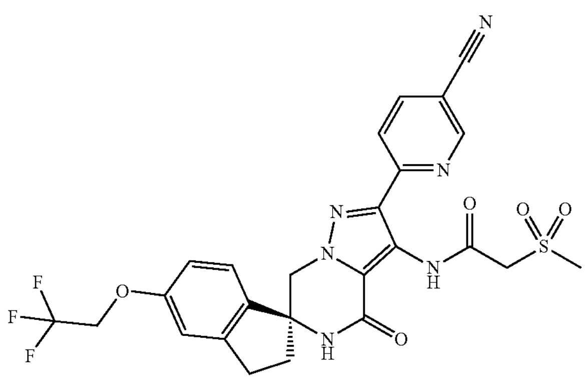 [SMILES: CS(=O)(=O)CC(=O)Nc1c(-c2ccc(C#N)cn2)nn2c1C(=O)N[C@]1(CCc3cc(OCC(F)(F)F)ccc31)C2] | A | 1.83 | 575.1 |
| I-5 | 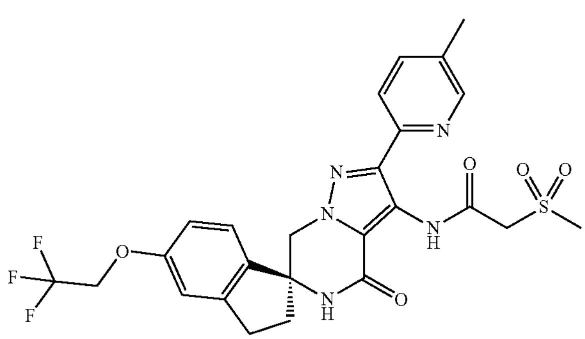 [SMILES: Cc1ccc(-c2nn3c(c2NC(=O)CS(C)(=O)=O)C(=O)N[C@]2(CCc4cc(OCC(F)(F)F)ccc42)C3)nc1] | A | 1.73 | 564.1 |

TABLE 1-continued

| No. | Structure | LCMS method | RT | MS |
|---|---|---|---|---|
| I-6 | 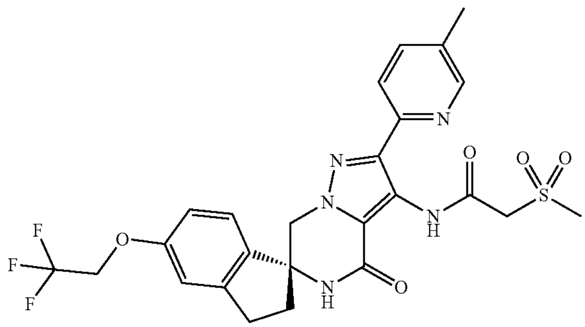 [SMILES: Cc1ccc(-c2nn3c(c2NC(=O)CS(C)(=O)=O)C(=O)N[C@@]2(CCc4cc(OCC(F)(F)F)ccc42)C3)nc1] | A | 1.73 | 564.1 |
| I-7 | 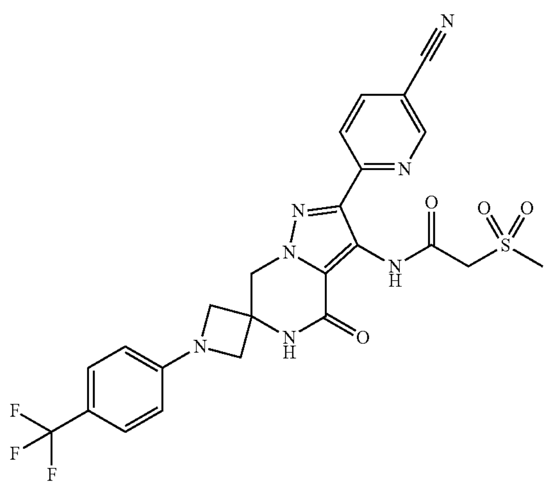 [SMILES: CS(=O)(=O)CC(=O)Nc1c(-c2ccc(C#N)cn2)nn2c1C(=O)NC1(CN(c3ccc(C(F)(F)F)cc3)C1)C2] | A | 1.88 | 560.1 |

TABLE 2

| I-8 | | B | 2.113 | 550.0 |

TABLE 2-continued
| | | | | |
|---|---|---|---|---|
| I-9 | 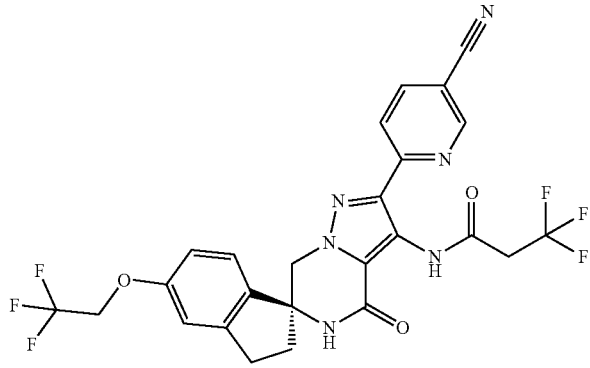 [SMILES: N#Cc1ccc(-c2nn3c(c2NC(=O)CC(F)(F)F)C(=O)N[C@]2(CCc4cc(OCC(F)(F)F)ccc42)C3)nc1] | B | 2.158 | 565.1 |
| I-10 | 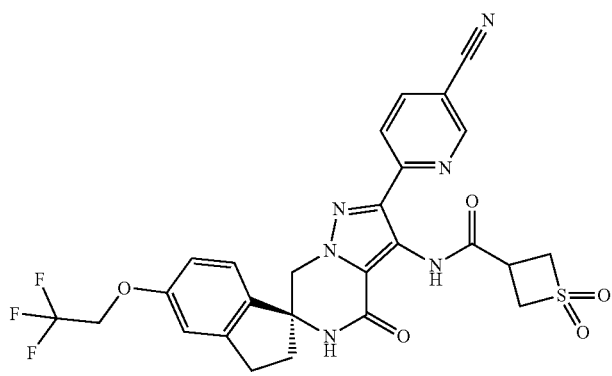 [SMILES: N#Cc1ccc(-c2nn3c(c2NC(=O)C2CS(=O)(=O)C2)C(=O)N[C@]2(CCc4cc(OCC(F)(F)F)ccc42)C3)nc1] | B | 1.999 | 587.0 |
| I-11 | 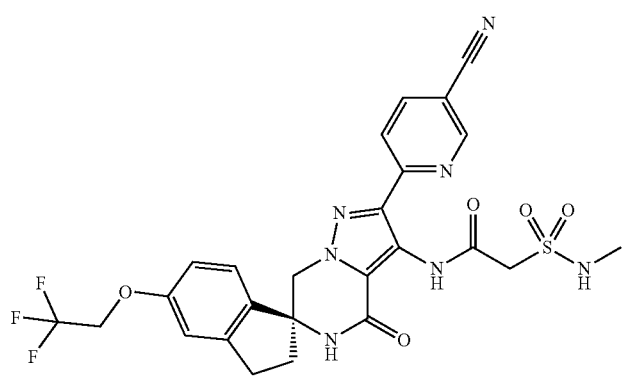 [SMILES: CNS(=O)(=O)CC(=O)Nc1c(-c2ccc(C#N)cn2)nn2c1C(=O)N[C@]1(CCc3cc(OCC(F)(F)F)ccc31)C2] | B | 1.991 | 590.1 |
| I-12 | 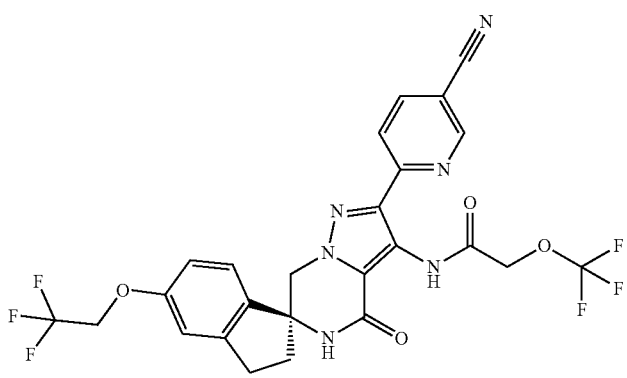 [SMILES: N#Cc1ccc(-c2nn3c(c2NC(=O)COC(F)(F)F)C(=O)N[C@]2(CCc4cc(OCC(F)(F)F)ccc42)C3)nc1] | B | 2.261 | 581.1 |

TABLE 2-continued
| I-13 | 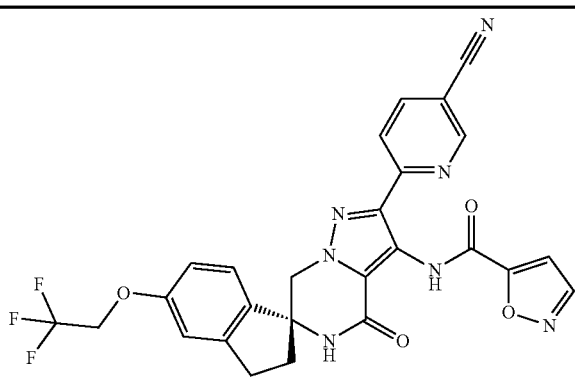 | B | 2.116 | 550.0 |
| I-14 | 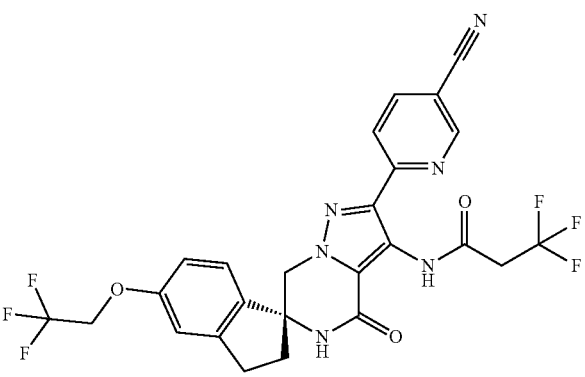 [SMILES: N#Cc1ccc(-c2nn3c(c2NC(=O)CC(F)(F)F)C(=O)N[C@@]2(CCc4cc(OCC(F)(F)F)ccc42)C3)nc1] | B | 2.164 | 565.1 |
TABLE 3
| I-15 | 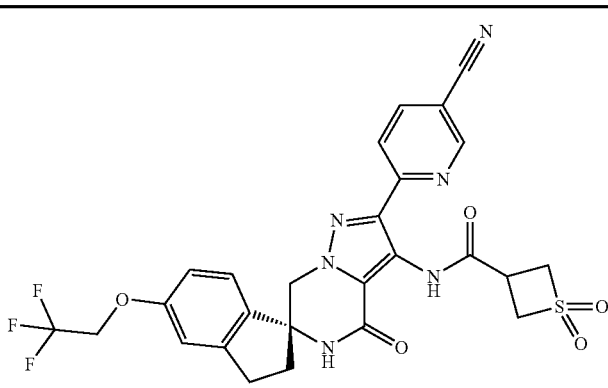 | B | 2 | 587.0 |
| I-16 | 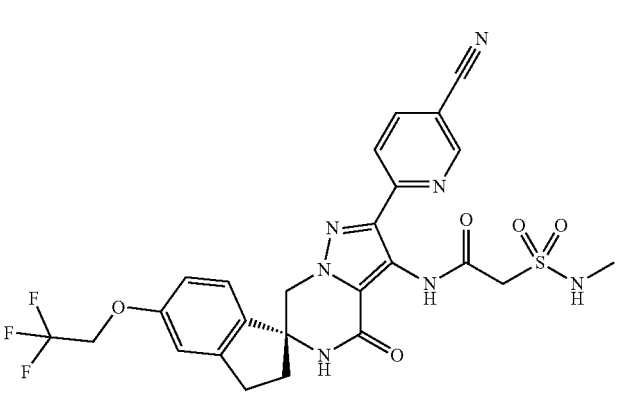 [SMILES: CNS(=O)(=O)CC(=O)Nc1c(-c2ccc(C#N)cn2)nn2c1C(=O)N[C@@]1(CCc3cc(OCC(F)(F)F)ccc31)C2] | B | 1.994 | 590.0 |

TABLE 3-continued
| | | | | |
|---|---|---|---|---|
| I-17 | 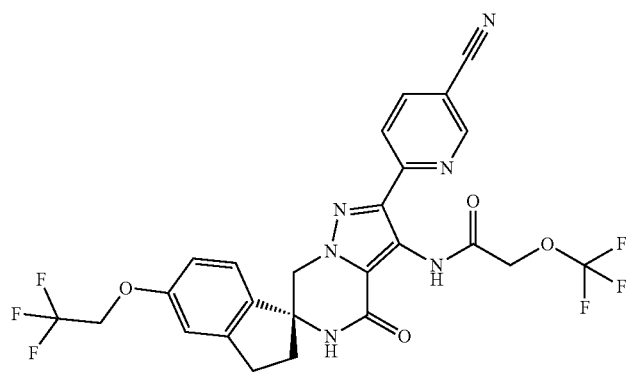 [SMILES: N#Cc1ccc(-c2nn3c(c2NC(=O)COC(F)(F)F)C(=O)N[C@@]2(CCc4cc(OCC(F)(F)F)ccc42)C3)nc1] | B | 2.262 | 581.1 |
| I-18 | 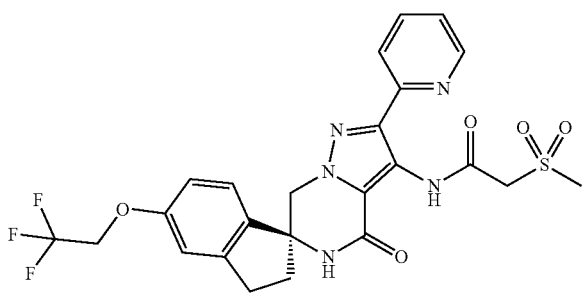 [SMILES: CS(=O)(=O)CC(=O)Nc1c(-c2ccccn2)nn2c1C(=O)N[C@]1(CCc3cc(OCC(F)(F)F)ccc31)C2] | A | 1.69 | 550.1 |
| I-19 | 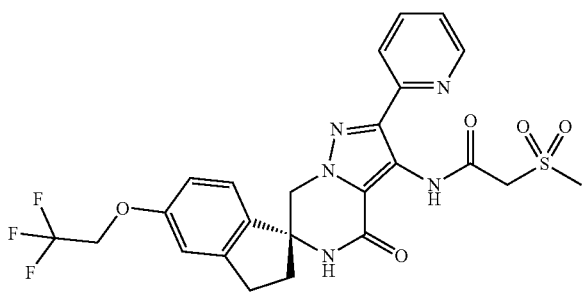 [SMILES: CS(=O)(=O)CC(=O)Nc1c(-c2ccccn2)nn2c1C(=O)N[C@@]1(CCc3cc(OCC(F)(F)F)ccc31)C2] | A | 1.69 | 550.1 |
| I-20 | 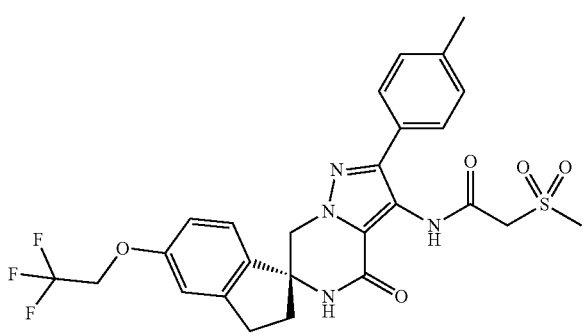 [SMILES: Cc1ccc(-c2nn3c(c2NC(=O)CS(C)(=O)=O)C(=O)N[C@@]2(CCc4cc(OCC(F)(F)F)ccc42)C3)cc1] | B | 2.233 | 563.1 |
| I-21 | 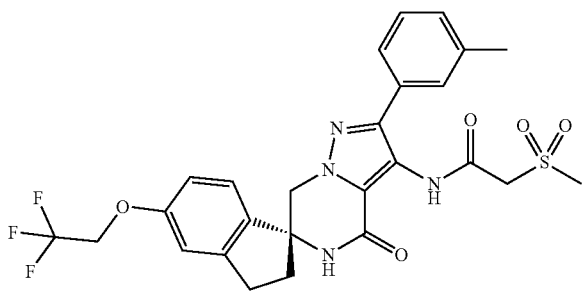 [SMILES: Cc1cccc(-c2nn3c(c2NC(=O)CS(C)(=O)=O)C(=O)N[C@@]2(CCc4cc(OCC(F)(F)F)ccc42)C3)c1] | B | 2.237 | 563.1 |

TABLE 4
| I-22 | 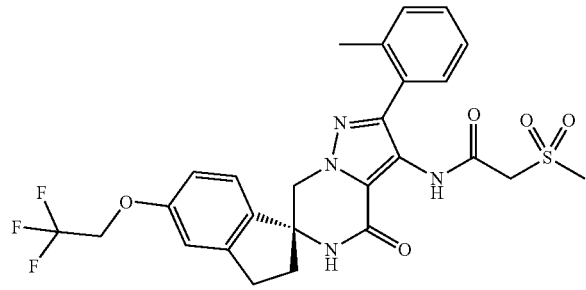 [SMILES: Cc1ccccc1-c1nn2c(c1NC(=O)CS(C)(=O)=O)C(=O)N[C@@]1(CCc3cc(OCC(F)(F)F)ccc31)C2] | B | 2.15 | 563.1 |
| I-23 | 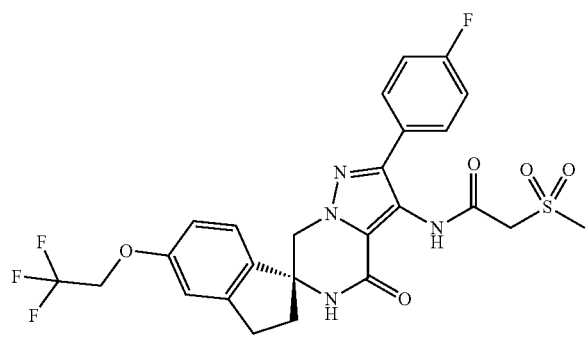 [SMILES: CS(=O)(=O)CC(=O)Nc1c(-c2ccc(F)cc2)nn2c1C(=O)N[C@@]1(CCc3cc(OCC(F)(F)F)ccc31)C2] | B | 2.18 | 567.1 |
| I-24 | 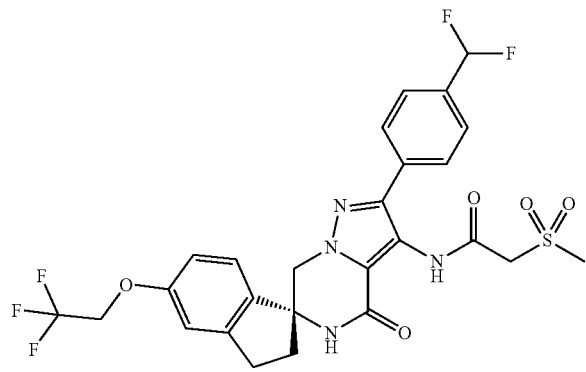 [SMILES: CS(=O)(=O)CC(=O)Nc1c(-c2ccc(C(F)F)cc2)nn2c1C(=O)N[C@@]1(CCc3cc(OCC(F)(F)F)ccc31)C2] | B | 2.241 | 599.1 |
| I-25 | 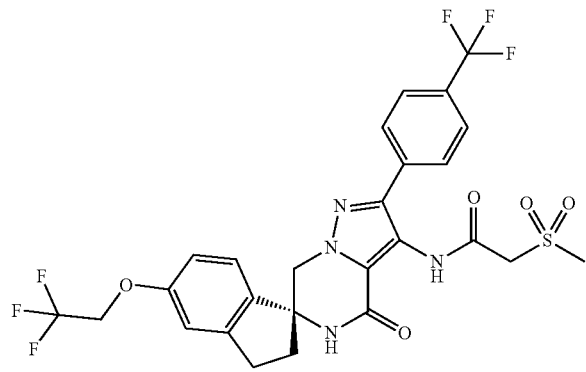 [SMILES: CS(=O)(=O)CC(=O)Nc1c(-c2ccc(C(F)(F)F)cc2)nn2c1C(=O)N[C@@]1(CCc3cc(OCC(F)(F)F)ccc31)C2] | B | 2.417 | 617.1 |

TABLE 4-continued
| I-26 | 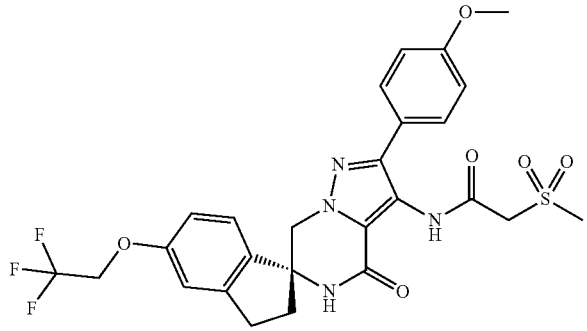 | B | 2.113 | 579.1 |
| I-27 | 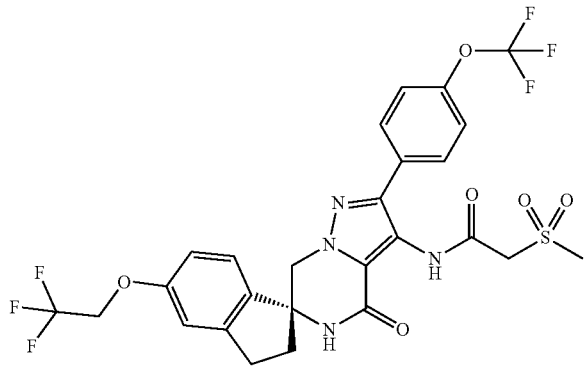 [SMILES: CS(=O)(=O)CC(=O)Nc1c(-c2ccc(OC(F)(F)F)cc2)nn2c1C(=O)N[C@@]1(CCc3cc(OCC(F)(F)F)ccc31)C2] | B | 2.447 | 633.1 |
| I-28 | 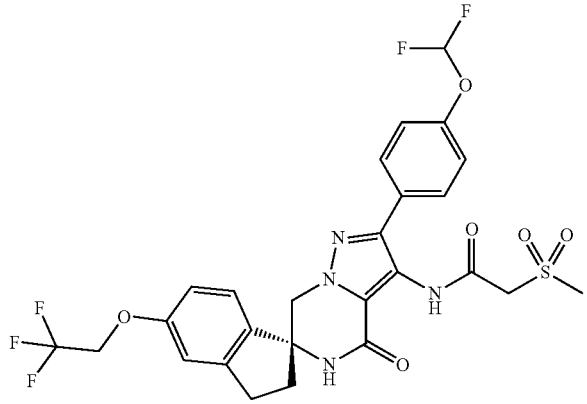 [SMILES: CS(=O)(=O)CC(=O)Nc1c(-c2ccc(OC(F)F)cc2)nn2c1C(=O)N[C@@]1(CCc3cc(OCC(F)(F)F)ccc31)C2] | B | 2.262 | 615.1 |
TABLE 5
| I-29 | 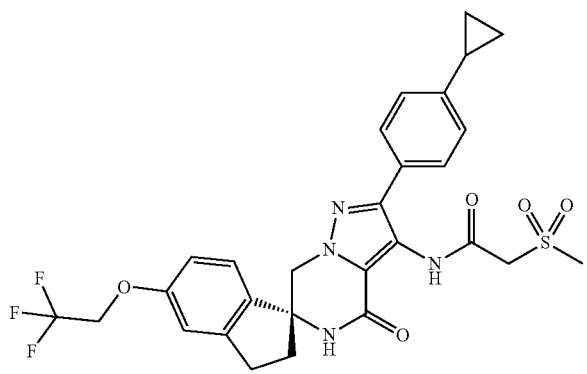 [SMILES: CS(=O)(=O)CC(=O)Nc1c(-c2ccc(C3CC3)cc2)nn2c1C(=O)N[C@@]1(CCc3cc(OCC(F)(F)F)ccc31)C2] | B | 2.356 | 589.1 |

TABLE 5-continued
| | | | | |
|---|---|---|---|---|
| I-30 | 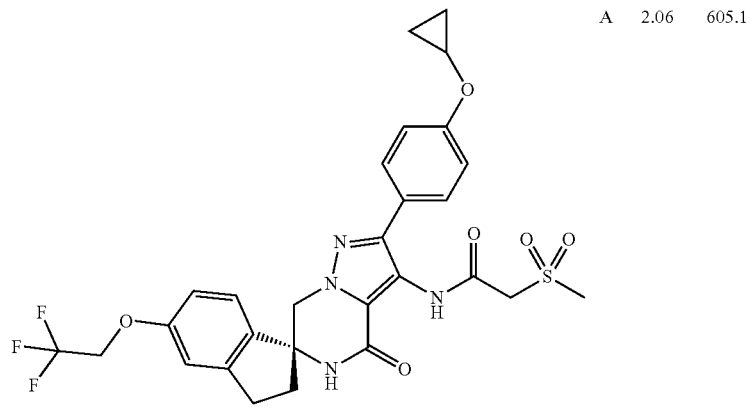 | A | 2.06 | 605.1 |
| I-31 | 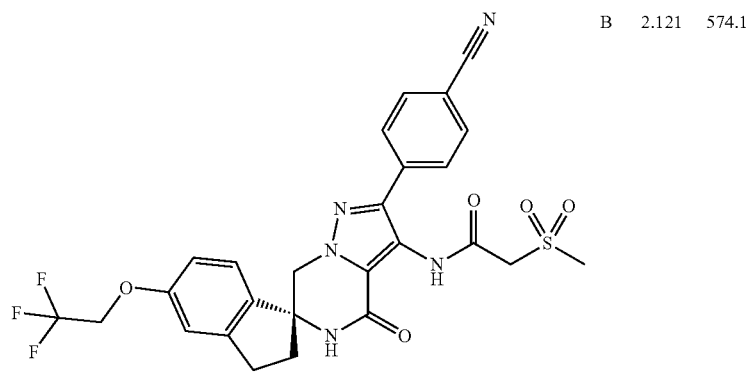 | B | 2.121 | 574.1 |
| I-32 | 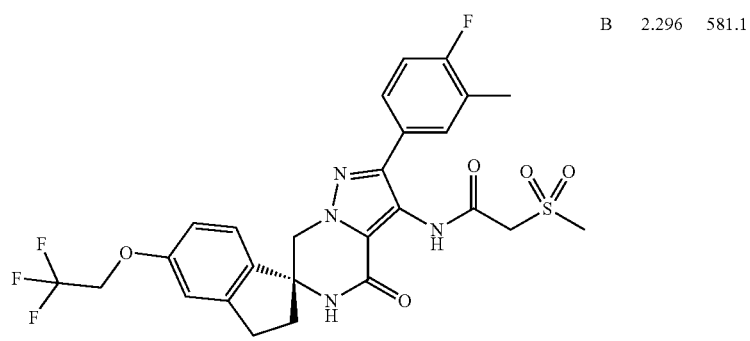 | B | 2.296 | 581.1 |
| I-33 | 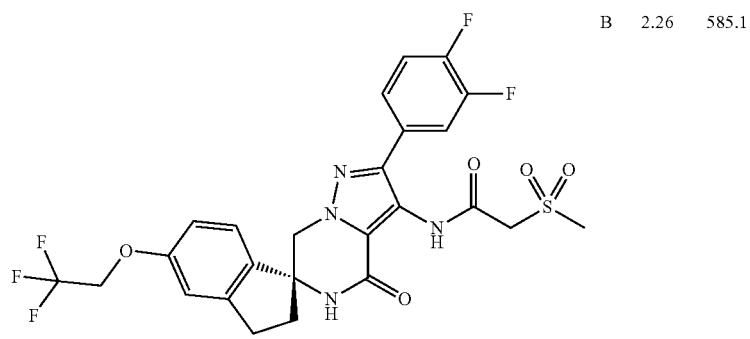 | B | 2.26 | 585.1 |

TABLE 5-continued

| ID | Structure | | | |
|---|---|---|---|---|
| I-34 | (structure) | B | 2.302 | 581.1 |
| I-35 | (structure) | B | 2.212 | 581.1 |

TABLE 6

| ID | Structure | | | |
|---|---|---|---|---|
| I-36 | (structure) | B | 2.365 | 603.1 |
| I-37 | (structure) | B | 1.948 | 607.2 |

TABLE 6-continued
| | | | | |
|---|---|---|---|---|
| I-38 | 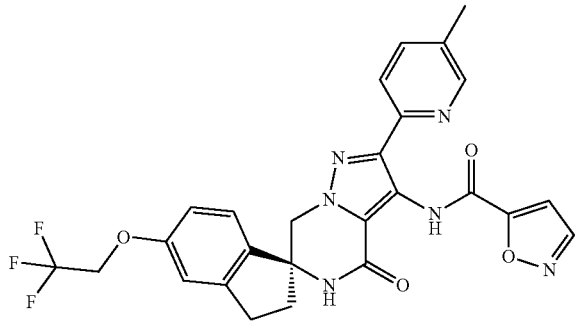 [SMILES: Cc1ccc(-c2nn3c(c2NC(=O)c2ccno2)C(=O)N[C@]2(CCc4cc(OCC(F)(F)F)ccc42)C3)nc1] | B | 2.12 | 539.2 |
| I-39 | 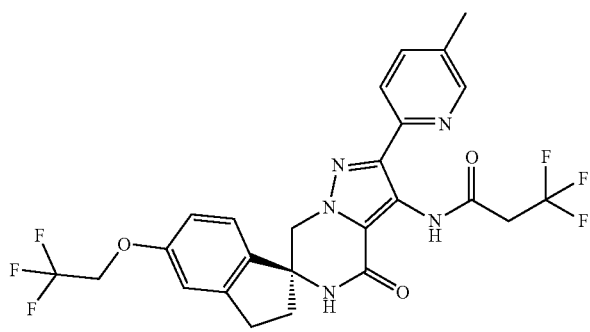 [SMILES: Cc1ccc(-c2nn3c(c2NC(=O)CC(F)(F)F)C(=O)N[C@]2(CCc4cc(OCC(F)(F)F)ccc42)C3)nc1] | B | 2.053 | 554.1 |
| I-40 | 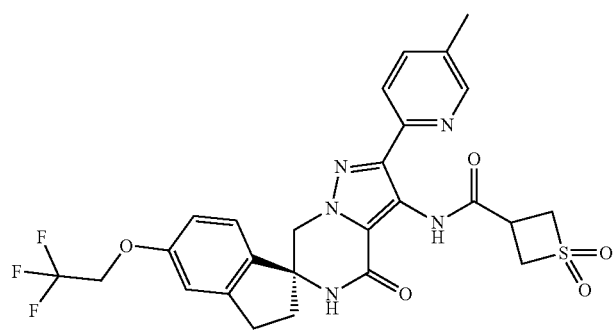 [SMILES: Cc1ccc(-c2nn3c(c2NC(=O)C2CS(=O)(=O)C2)C(=O)N[C@]2(CCc4cc(OCC(F)(F)F)ccc42)C3)nc1] | B | 1.88 | 576.1 |
| I-41 | 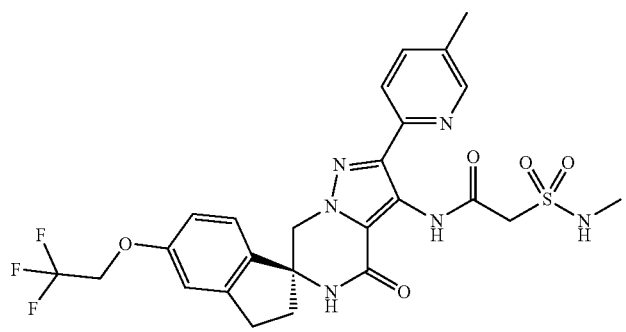 [SMILES: CNS(=O)(=O)CC(=O)Nc1c(-c2ccc(C)cn2)nn2c1C(=O)N[C@]1(CCc3cc(OCC(F)(F)F)ccc31)C2] | B | 1.826 | 579.1 |

TABLE 6-continued
| I-42 | 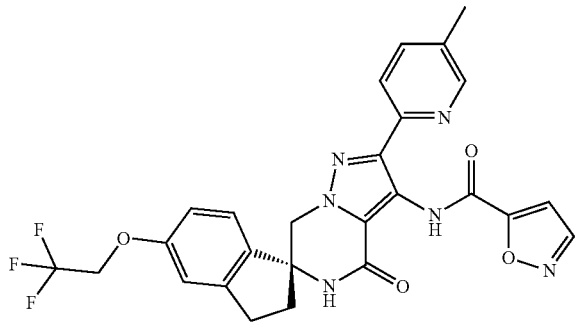 [SMILES: Cc1ccc(-c2nn3c(c2NC(=O)c2ccno2)C(=O)N[C@@]2(CCc4cc(OCC(F)(F)F)ccc42)C3)nc1] | B | 2.12 | 539.1 |
TABLE 7
| I-43 | 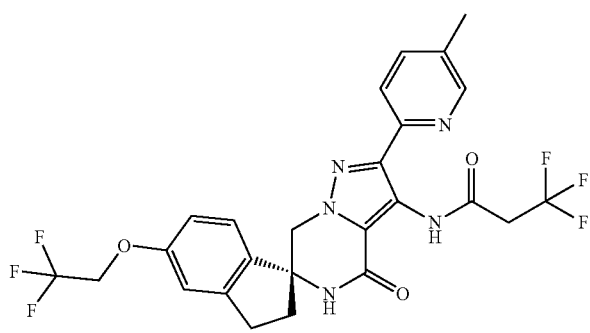 [SMILES: Cc1ccc(-c2nn3c(c2NC(=O)CC(F)(F)F)C(=O)N[C@@]2(CCc4cc(OCC(F)(F)F)ccc42)C3)nc1] | B | 2.055 | 554.1 |
| I-44 | 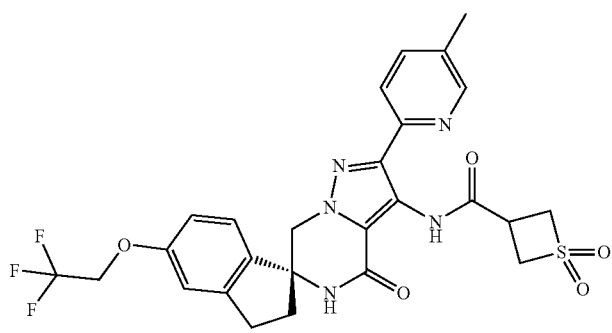 [SMILES: Cc1ccc(-c2nn3c(c2NC(=O)C2CS(=O)(=O)C2)C(=O)N[C@@]2(CCc4cc(OCC(F)(F)F)ccc42)C3)nc1] | B | 1.879 | 576.1 |
| I-45 | 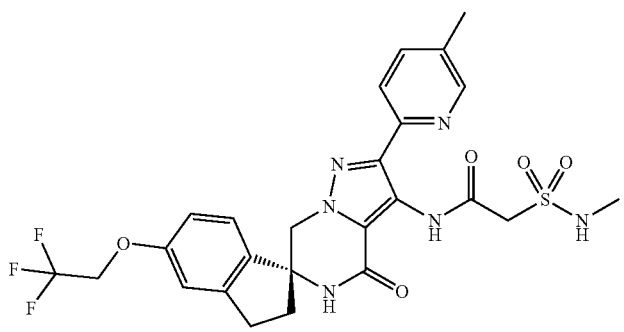 [SMILES: CNS(=O)(=O)CC(=O)Nc1c(-c2ccc(C)cn2)nn2c1C(=O)N[C@@]1(CCc3cc(OCC(F)(F)F)ccc31)C2] | B | 1.832 | 579.1 |

TABLE 7-continued
| I-46 | 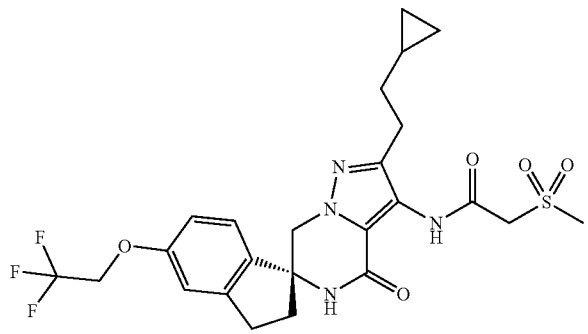 [SMILES: CS(=O)(=O)CC(=O)Nc1c(CCC2CC2)nn2c1C(=O)N[C@@]1(CCc3cc(OCC(F)(F)F)ccc31)C2] | B | 2.075 | 541.1 |
| I-47 | 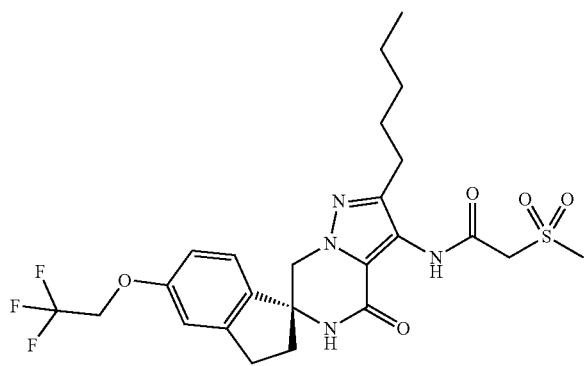 [SMILES: CCCCCc1nn2c(c1NC(=O)CS(C)(=O)=O)C(=O)N[C@@]1(CCc3cc(OCC(F)(F)F)ccc31)C2] | B | 2.208 | 543.1 |
| I-48 | 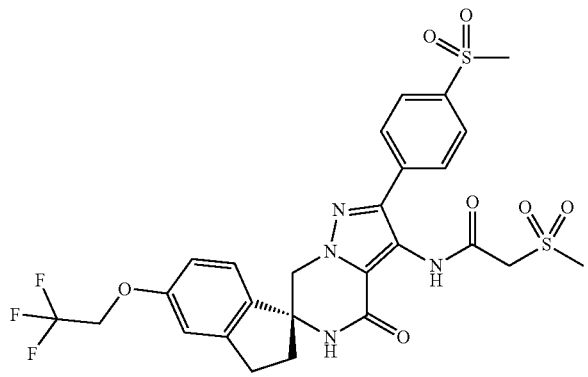 [SMILES: CS(=O)(=O)CC(=O)Nc1c(-c2ccc(S(C)(=O)=O)cc2)nn2c1C(=O)N[C@@]1(CCc3cc(OCC(F)(F)F)ccc31)C2] | B | 1.94 | 627.1 |
| I-49 | 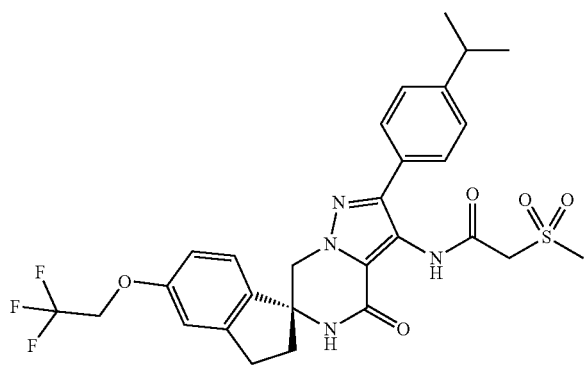 [SMILES: CC(C)c1ccc(-c2nn3c(c2NC(=O)CS(C)(=O)=O)C(=O)N[C@@]2(CCc4cc(OCC(F)(F)F)ccc42)C3)cc1] | B | 2.474 | 591.1 |

TABLE 8

| | | | | | |
|---|---|---|---|---|---|
| I-50 | | (structure) | B | 2.281 | 585.1 |
| I-51 | | (structure) | B | 2.216 | 592.1 |
| I-52 | | (structure) | B | 2.159 | 597.1 |
| I-53 | | (structure) | B | 2.399 | 599.1 |

TABLE 8-continued
| I-54 | 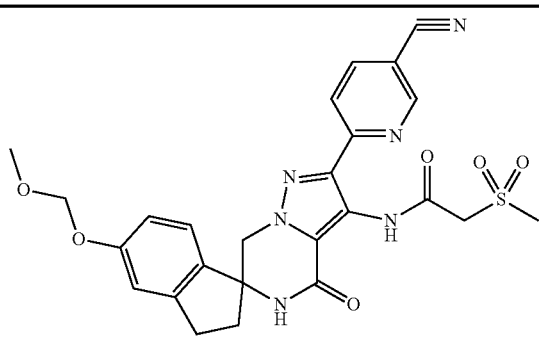 | B | 1.69 | 537.1 |
| I-55 | 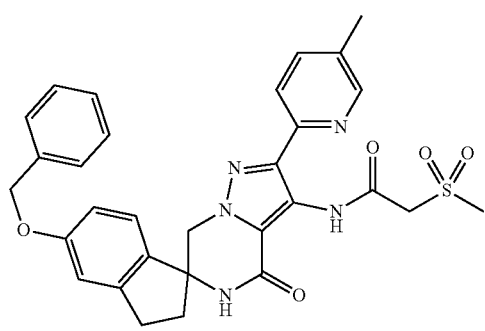 [SMILES: Cc1ccc(-c2nn3c(c2NC(=O)CS(C)(=O)=O)C(=O)NC2(CCc4cc(OCc5ccccc5)ccc42)C3)nc1] | B | 1.93 | 572.1 |
| I-56 | 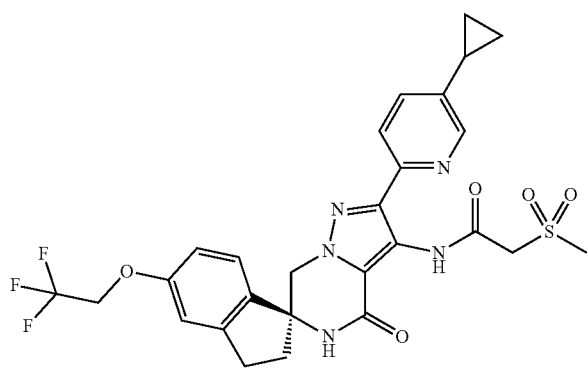 [SMILES: CS(=O)(=O)CC(=O)Nc1c(-c2ccc(C3CC3)cn2)nn2c1C(=O)N[C@]1(CCc3cc(OCC(F)(F)F)ccc31)C2] | A | 1.88 | 590.1 |
TABLE 9
| I-57 | 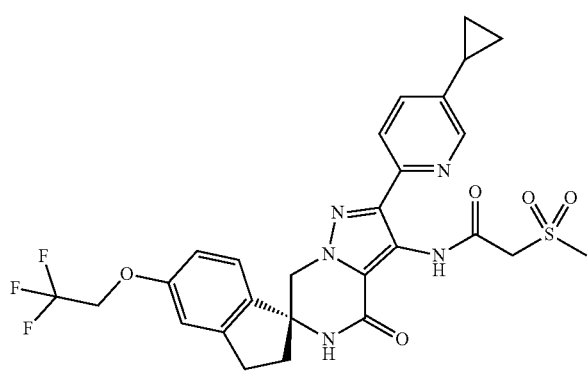 [SMILES: CS(=O)(=O)CC(=O)Nc1c(-c2ccc(C3CC3)cn2)nn2c1C(=O)N[C@@]1(CCc3cc(OCC(F)(F)F)ccc31)C2] | A | 1.88 | 590.1 |

TABLE 9-continued
| | | | | |
|---|---|---|---|---|
| I-58 | 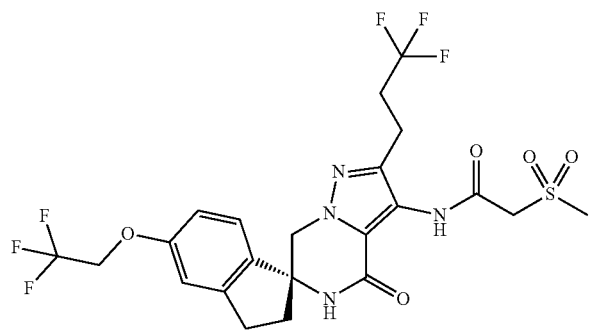 [SMILES: CS(=O)(=O)CC(=O)Nc1c(CCC(F)(F)F)nn2c1C(=O)N[C@@]1(CCc3cc(OCC(F)(F)F)ccc31)C2] | A | 1.94 | 569.1 |
| I-59 | 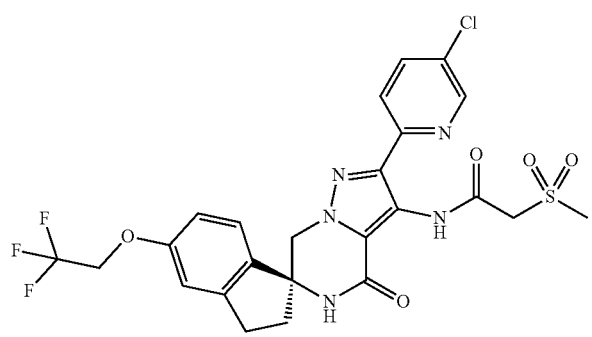 [SMILES: CS(=O)(=O)CC(=O)Nc1c(-c2ccc(Cl)cn2)nn2c1C(=O)N[C@]1(CCc3cc(OCC(F)(F)F)ccc31)C2] | A | 1.97 | 584.1 |
| I-60 | 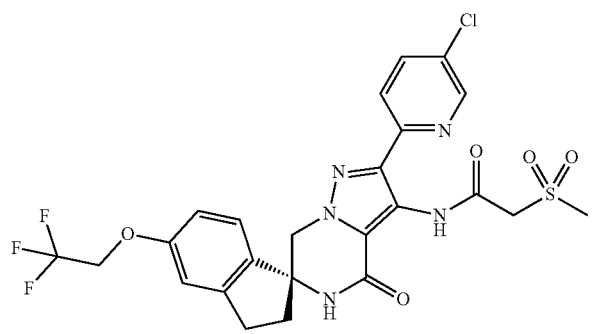 [SMILES: CS(=O)(=O)CC(=O)Nc1c(-c2ccc(Cl)cn2)nn2c1C(=O)N[C@@]1(CCc3cc(OCC(F)(F)F)ccc31)C2] | A | 1.97 | 584.1 |
| I-61 | 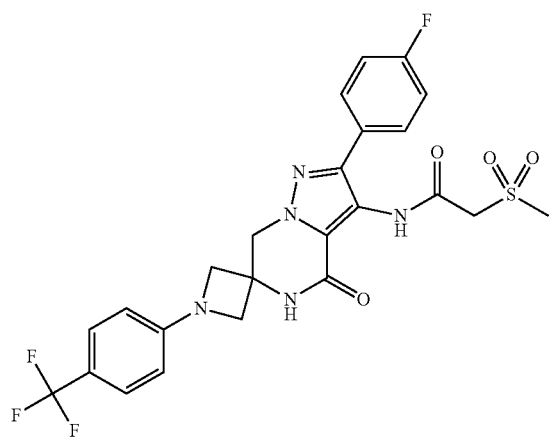 [SMILES: CS(=O)(=O)CC(=O)Nc1c(-c2ccc(F)cc2)nn2c1C(=O)NC1(CN(c3ccc(C(F)(F)F)cc3)C1)C2] | A | 2.02 | 552.1 |

TABLE 9-continued
| I-62 | 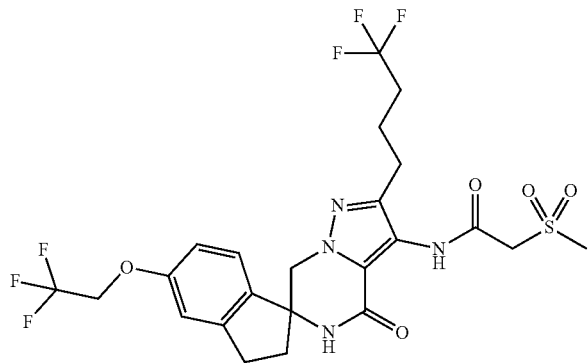 [SMILES: CS(=O)(=O)CC(=O)Nc1c(CCCC(F)(F)F)nn2c1C(=O)NC1(CCc3cc(OCC(F)(F)F)ccc31)C2] | A | 1.98 | 583.1 |
| I-63 | 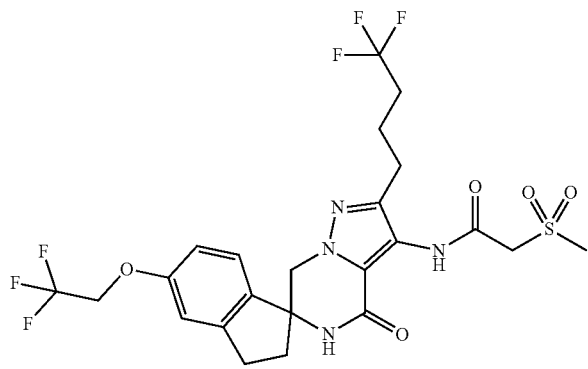 [SMILES: CS(=O)(=O)CC(=O)Nc1c(CCCC(F)(F)F)nn2c1C(=O)NC1(CCc3cc(OCC(F)(F)F)ccc31)C2] | A | 1.97 | 538.1 |
TABLE 10
| I-64 | 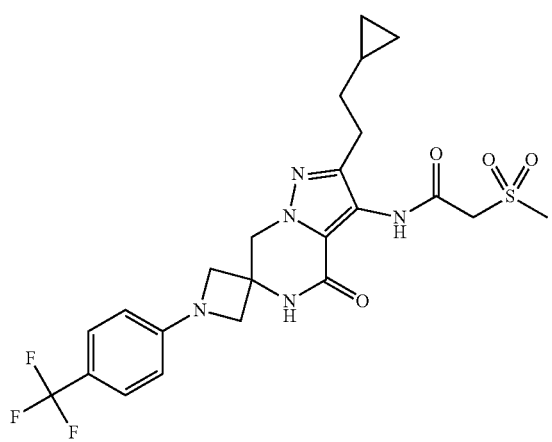 [SMILES: CS(=O)(=O)CC(=O)Nc1c(CCC2CC2)nn2c1C(=O)NC1(CN(c3ccc(C(F)(F)F)cc3)C1)C2] | A | 2.01 | 526.1 |

TABLE 10-continued
| I-65 | 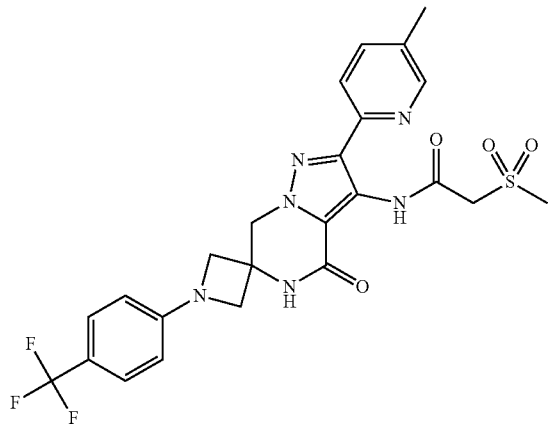 [SMILES: Cc1ccc(-c2nn3c(c2NC(=O)CS(C)(=O)=O)C(=O)NC2(CN(c4ccc(C(F)(F)F)cc4)C2)C3)nc1] | A | 1.78 | 549.1 |
| I-66 | 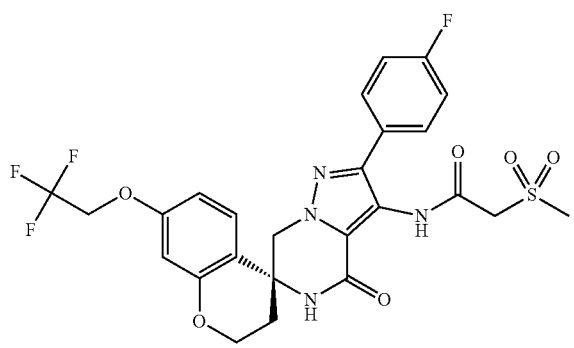 [SMILES: CS(=O)(=O)CC(=O)Nc1c(-c2ccc(F)cc2)nn2c1C(=O)N[C@@]1(CCOc3cc(OCC(F)(F)F)ccc31)C2] | C | 2.05 | 583.2 |
| I-67 | 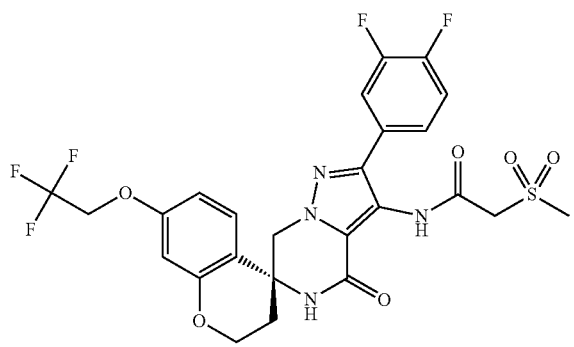 [SMILES: CS(=O)(=O)CC(=O)Nc1c(-c2ccc(F)c(F)c2)nn2c1C(=O)N[C@@]1(CCOc3cc(OCC(F)(F)F)ccc31)C2] | C | 2.17 | 601.2 |
| I-68 | 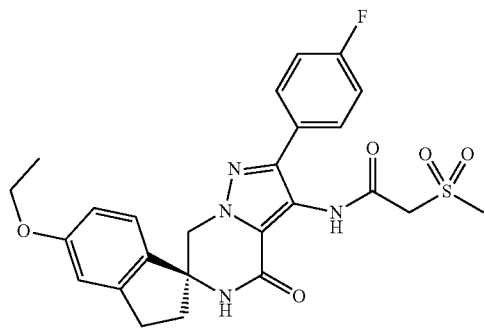 [SMILES: CCOc1ccc2c(c1)CC[C@@]21Cn2nc(-c3ccc(F)cc3)c(NC(=O)CS(C)(=O)=O)c2C(=O)N1] | C | 1.95 | 513.3 |

TABLE 10-continued
| I-69 | 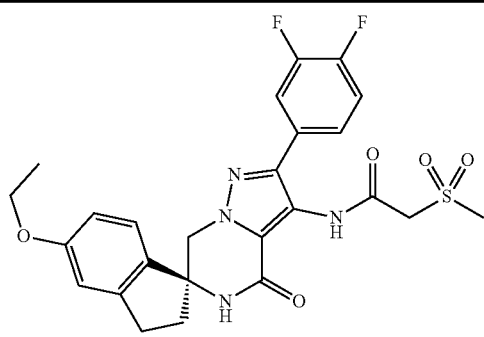 | C | 2.05 | 531.3 |
| I-70 | 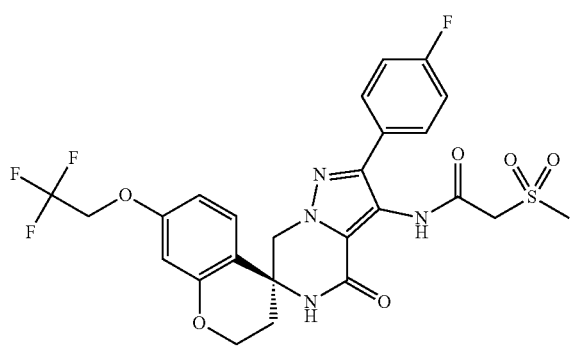 [SMILES: CS(=O)(=O)CC(=O)Nc1c(-c2ccc(F)cc2)nn2c1C(=O)N[C@]1(CCOc3cc(OCC(F)(F)F)ccc31)C2] | C | 2.05 | 583.1 |
TABLE 11
| I-71 | 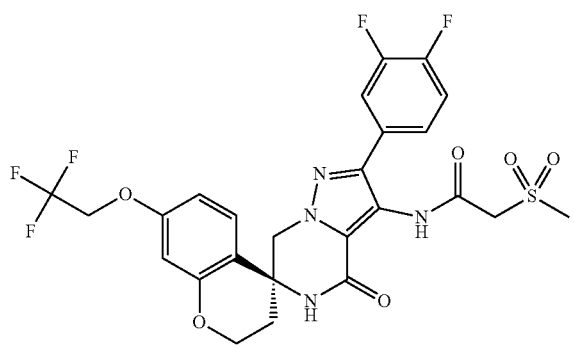 [SMILES: CS(=O)(=O)CC(=O)Nc1c(-c2ccc(F)c(F)c2)nn2c1C(=O)N[C@]1(CCOc3cc(OCC(F)(F)F)ccc31)C2] | C | 2.13 | 601.1 |
| I-72 | 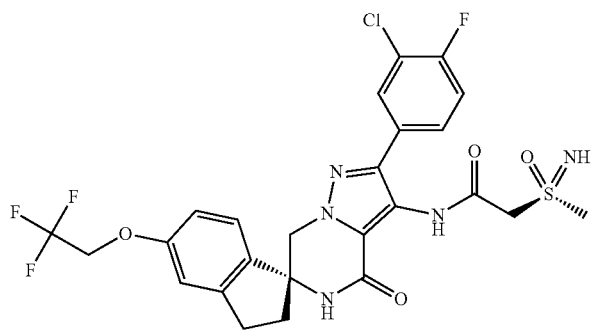 [SMILES: C[S@@](=N)(=O)CC(=O)Nc1c(-c2ccc(F)c(Cl)c2)nn2c1C(=O)N[C@@]1(CCc3cc(OCC(F)(F)F)ccc31)C2] | C | 2.13 | 600.2 |

TABLE 11-continued
| I-73 | 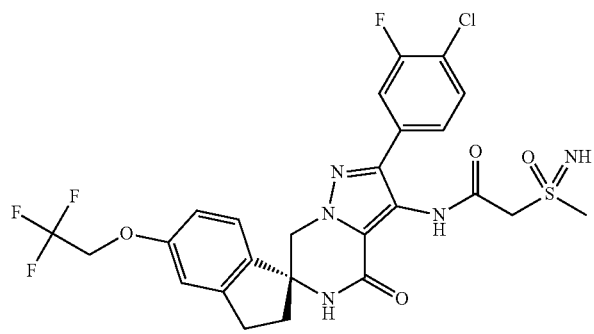 [SMILES: CS(=N)(=O)CC(=O)Nc1c(-c2ccc(Cl)c(F)c2)nn2c1C(=O)N[C@@]1(CCc3cc(OCC(F)(F)F)ccc31)C2] | C | 2.14 | 600.3 |
| I-74 | 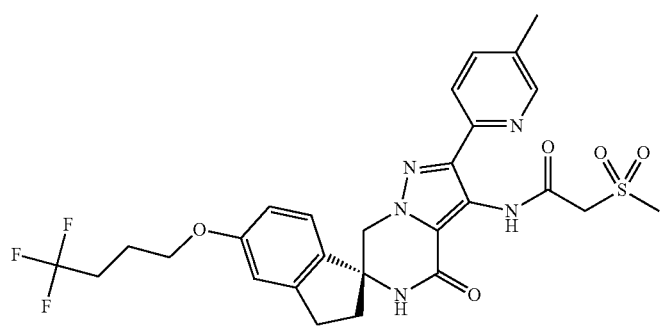 [SMILES: Cc1ccc(-c2nn3c(c2NC(=O)CS(C)(=O)=O)C(=O)N[C@@]2(CCc4cc(OCCCC(F)(F)F)ccc42)C3)nc1] | D | 1.9 | 592.0 |
| I-75 | 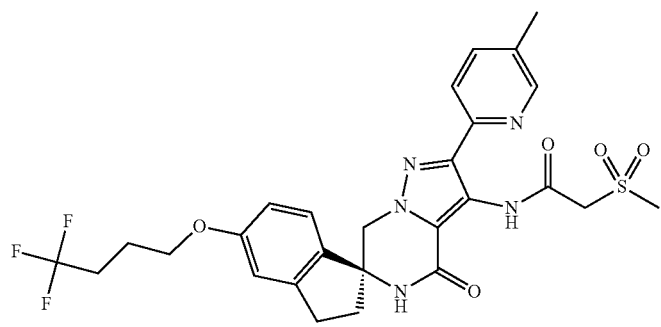 [SMILES: Cc1ccc(-c2nn3c(c2NC(=O)CS(C)(=O)=O)C(=O)N[C@]2(CCc4cc(OCCCC(F)(F)F)ccc42)C3)nc1] | D | 1.9 | 592.0 |
| I-76 | 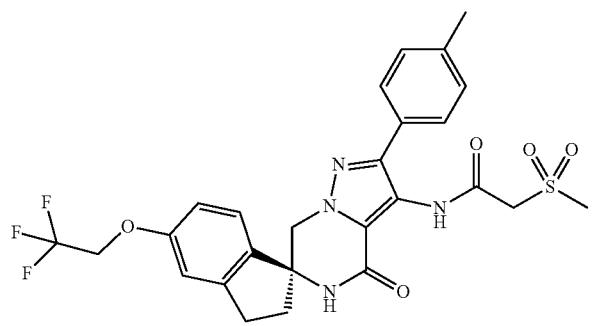 [SMILES: Cc1ccc(-c2nn3c(c2NC(=O)CS(C)(=O)=O)C(=O)N[C@]2(CCc4cc(OCC(F)(F)F)ccc42)C3)cc1] | B | 2.234 | 563.1 |
| I-77 | 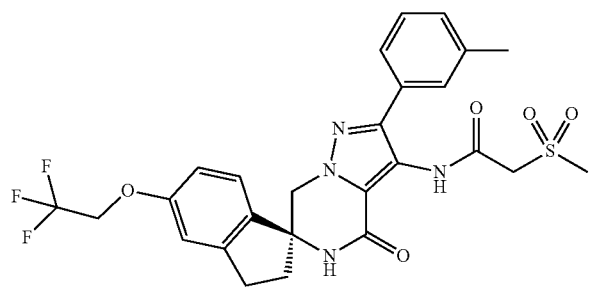 [SMILES: Cc1cccc(-c2nn3c(c2NC(=O)CS(C)(=O)=O)C(=O)N[C@]2(CCc4cc(OCC(F)(F)F)ccc42)C3)c1] | B | 2.237 | 563.1 |

TABLE 12
| | | | | |
|---|---|---|---|---|
| I-78 | 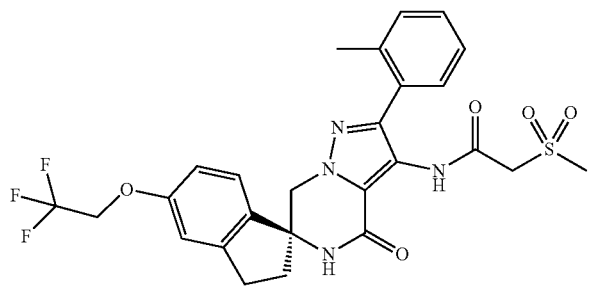 [SMILES: Cc1ccccc1-c1nn2c(c1NC(=O)CS(C)(=O)=O)C(=O)N[C@]1(CCc3cc(OCC(F)(F)F)ccc31)C2] | B | 2.149 | 563.1 |
| I-79 | 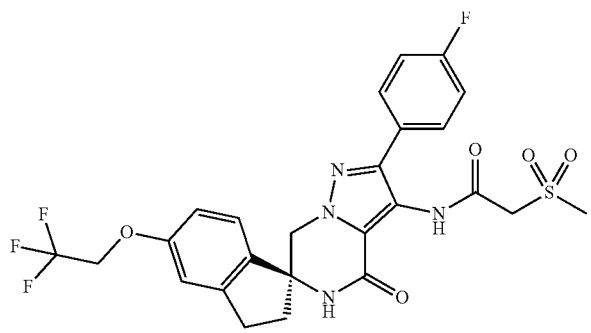 [SMILES: CS(=O)(=O)CC(=O)Nc1c(-c2ccc(F)cc2)nn2c1C(=O)N[C@]1(CCc3cc(OCC(F)(F)F)ccc31)C2] | B | 2.18 | 567.1 |
| I-80 | 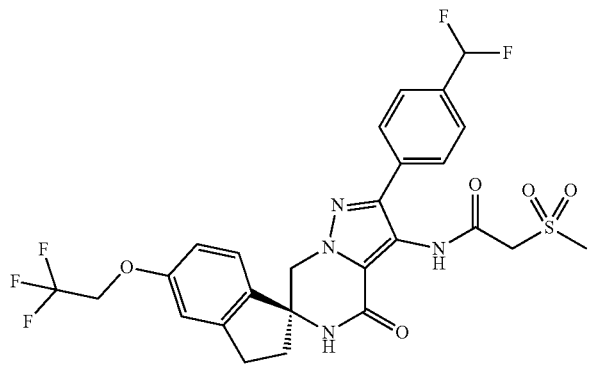 [SMILES: CS(=O)(=O)CC(=O)Nc1c(-c2ccc(C(F)F)cc2)nn2c1C(=O)N[C@]1(CCc3cc(OCC(F)(F)F)ccc31)C2] | B | 2.24 | 599.1 |
| I-81 | 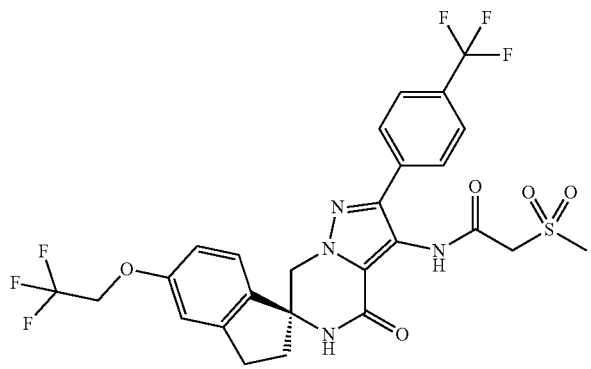 [SMILES: CS(=O)(=O)CC(=O)Nc1c(-c2ccc(C(F)(F)F)cc2)nn2c1C(=O)N[C@]1(CCc3cc(OCC(F)(F)F)ccc31)C2] | B | 2.417 | 617.1 |

TABLE 12-continued
| I-82 | 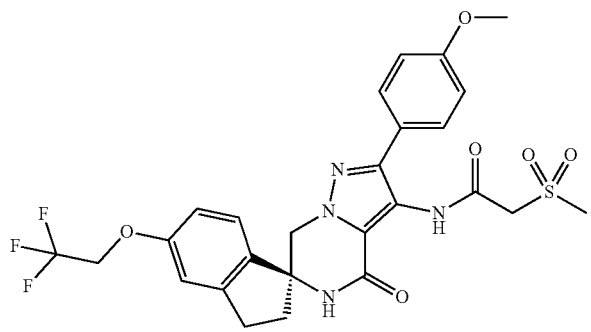 [SMILES: COc1ccc(-c2nn3c(c2NC(=O)CS(C)(=O)=O)C(=O)N[C@]2(CCc4cc(OCC(F)(F)F)ccc42)C3)cc1] | B | 2.112 | 579.1 |
| I-83 | 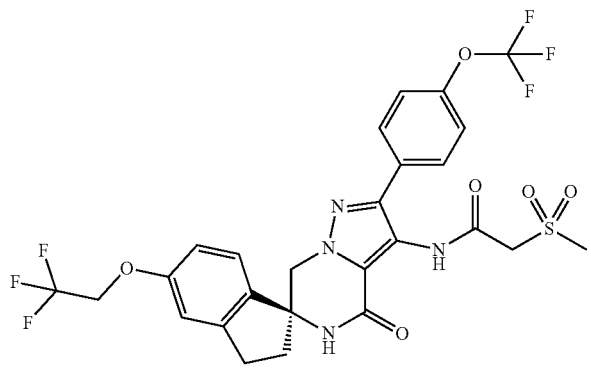 [SMILES: CS(=O)(=O)CC(=O)Nc1c(-c2ccc(OC(F)(F)F)cc2)nn2c1C(=O)N[C@]1(CCc3cc(OCC(F)(F)F)ccc31)C2] | B | 2.448 | 633.1 |
| I-84 | 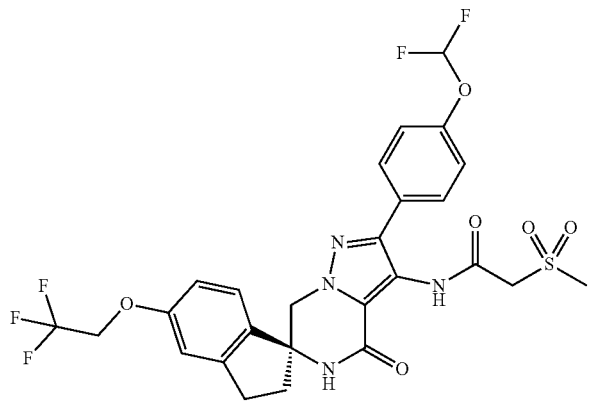 [SMILES: CS(=O)(=O)CC(=O)Nc1c(-c2ccc(OC(F)F)cc2)nn2c1C(=O)N[C@]1(CCc3cc(OCC(F)(F)F)ccc31)C2] | B | 2.26 | 615.1 |
TABLE 13
| I-85 | 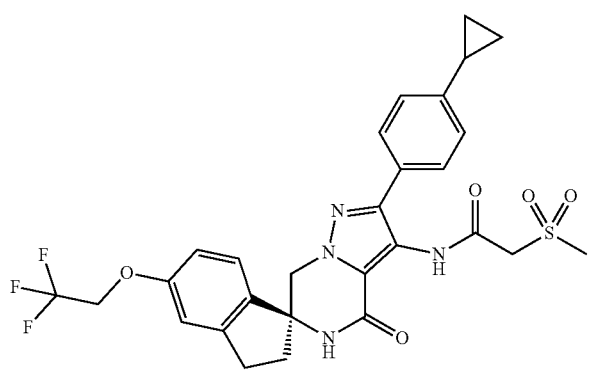 | B | 2.353 | 589.1 |

TABLE 13-continued
| | | | | |
|---|---|---|---|---|
| I-86 | 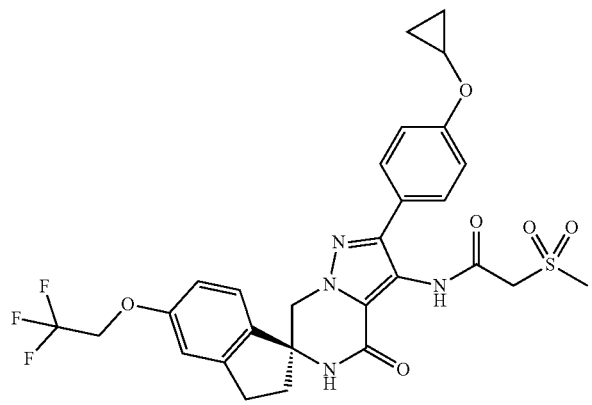 [SMILES: CS(=O)(=O)CC(=O)Nc1c(-c2ccc(OC3CC3)cc2)nn2c1C(=O)N[C@]1(CCc3cc(OCC(F)(F)F)ccc31)C2] | B | 2.294 | 605.2 |
| I-87 | 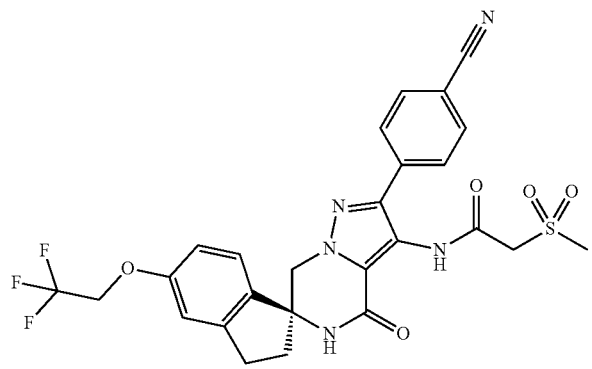 [SMILES: CS(=O)(=O)CC(=O)Nc1c(-c2ccc(C#N)cc2)nn2c1C(=O)N[C@]1(CCc3cc(OCC(F)(F)F)ccc31)C2] | B | 2.119 | 574.1 |
| I-88 | 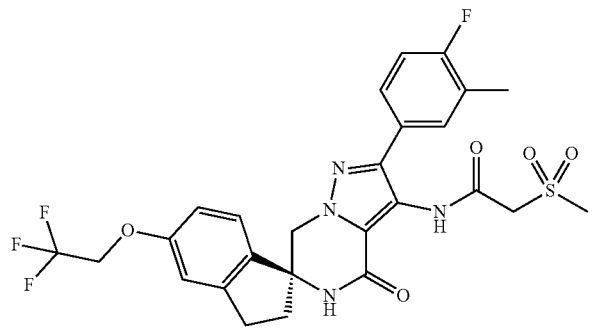 [SMILES: Cc1cc(-c2nn3c(c2NC(=O)CS(C)(=O)=O)C(=O)N[C@]2(CCc4cc(OCC(F)(F)F)ccc42)C3)ccc1F] | B | 2.295 | 581.1 |
| I-89 | 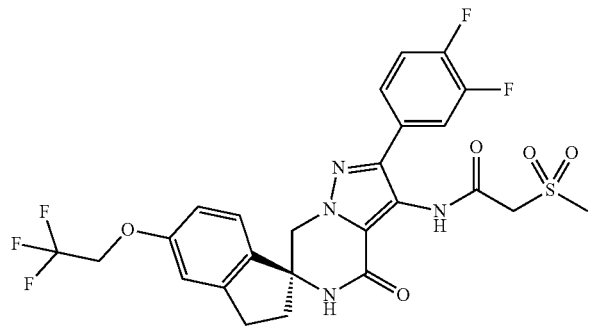 [SMILES: CS(=O)(=O)CC(=O)Nc1c(-c2ccc(F)c(F)c2)nn2c1C(=O)N[C@]1(CCc3cc(OCC(F)(F)F)ccc31)C2] | B | 2.259 | 585.1 |

TABLE 13-continued
| | | | | |
|---|---|---|---|---|
| I-90 | 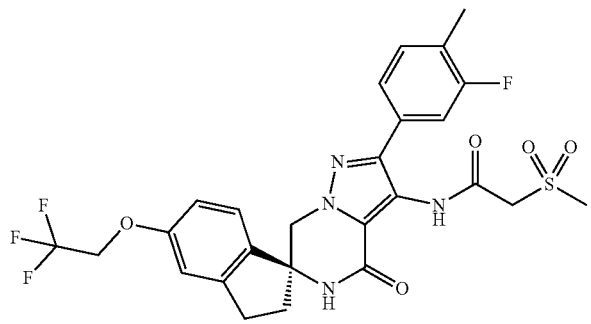 [SMILES: Cc1ccc(-c2nn3c(c2NC(=O)CS(C)(=O)=O)C(=O)N[C@]2(CCc4cc(OCC(F)(F)F)ccc42)C3)cc1F] | B | 2.304 | 581.1 |
| I-91 | 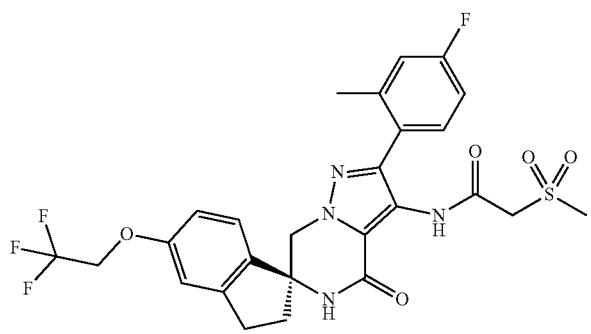 [SMILES: Cc1cc(F)ccc1-c1nn2c(c1NC(=O)CS(C)(=O)=O)C(=O)N[C@]1(CCc3cc(OCC(F)(F)F)ccc31)C2] | B | 2.211 | 581.1 |
TABLE 14
| | | | | |
|---|---|---|---|---|
| I-92 | 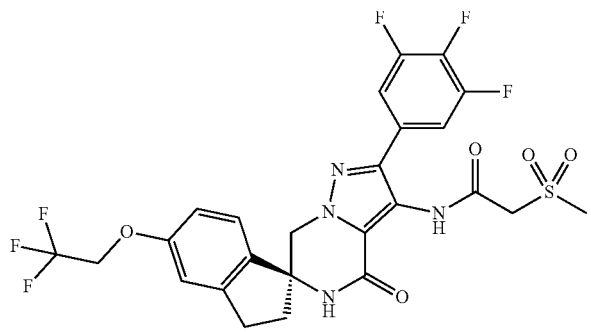 [SMILES: CS(=O)(=O)CC(=O)Nc1c(-c2cc(F)c(F)c(F)c2)nn2c1C(=O)N[C@]1(CCc3cc(OCC(F)(F)F)ccc31)C2] | B | 2.365 | 603.0 |
| I-93 | 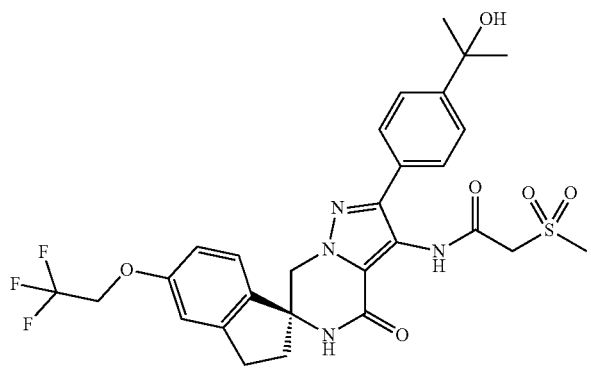 [SMILES: CC(C)(O)c1ccc(-c2nn3c(c2NC(=O)CS(C)(=O)=O)C(=O)N[C@]2(CCc4cc(OCC(F)(F)F)ccc42)C3)cc1] | B | 1.948 | 607.2 |

TABLE 14-continued
| I-94 | 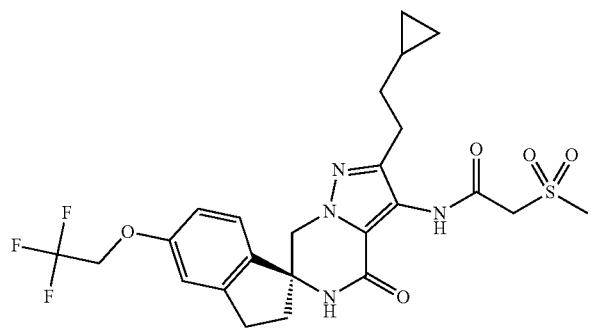 [SMILES: CS(=O)(=O)CC(=O)Nc1c(CCC2CC2)nn2c1C(=O)N[C@]1(CCc3cc(OCC(F)(F)F)ccc31)C2] | B | 2.076 | 541.1 |
| I-95 | 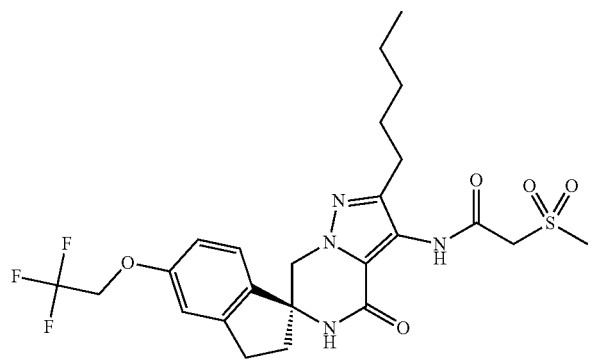 [SMILES: CCCCCc1nn2c(c1NC(=O)CS(C)(=O)=O)C(=O)N[C@]1(CCc3cc(OCC(F)(F)F)ccc31)C2] | B | 2.208 | 543.1 |
| I-96 | 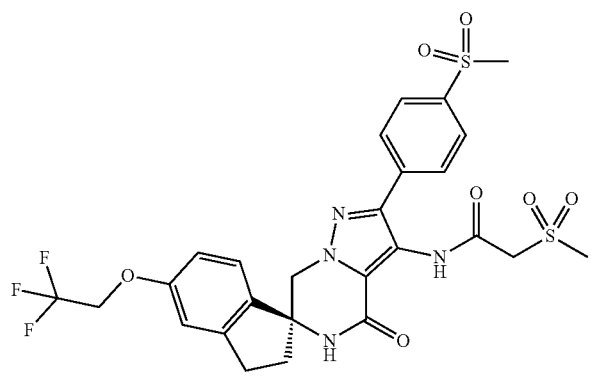 [SMILES: CS(=O)(=O)CC(=O)Nc1c(-c2ccc(S(C)(=O)=O)cc2)nn2c1C(=O)N[C@]1(CCc3cc(OCC(F)(F)F)ccc31)C2] | B | 1.94 | 627.1 |
| I-97 | 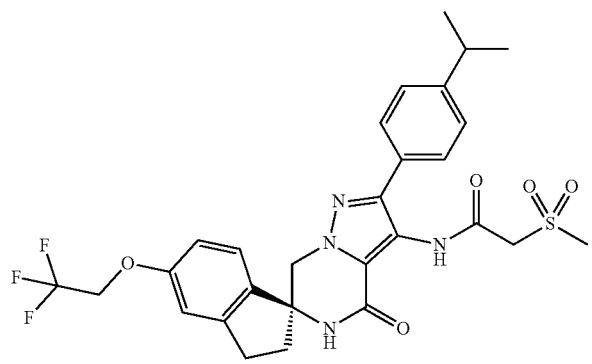 [SMILES: CC(C)c1ccc(-c2nn3c(c2NC(=O)CS(C)(=O)=O)C(=O)N[C@]2(CCc4cc(OCC(F)(F)F)ccc42)C3)cc1] | B | 2.473 | 591.1 |

TABLE 14-continued
| I-98 | 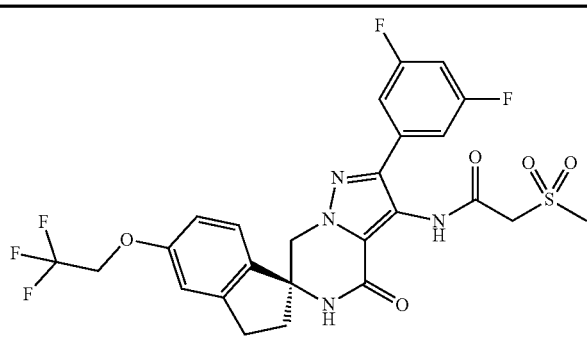 | B | 2.279 | 585.1 |
TABLE 15
| I-99 | 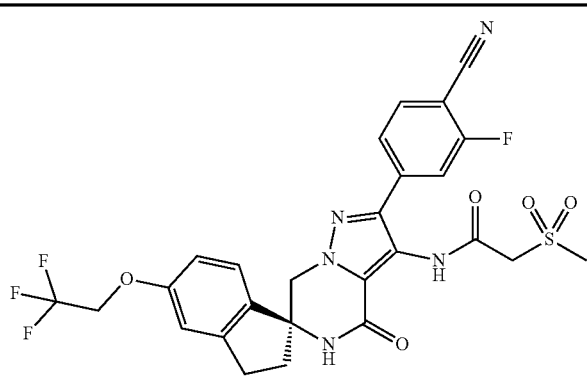 | B | 2.215 | 592.1 |
| I-100 | 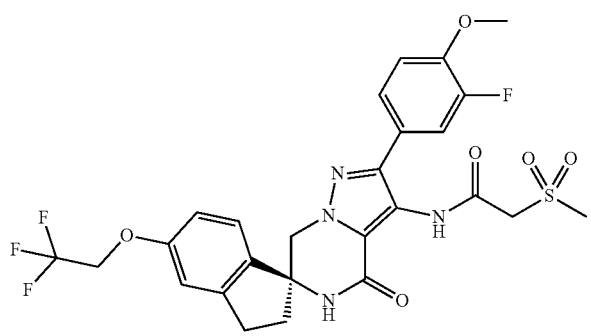 [SMILES: COc1ccc(-c2nn3c(c2NC(=O)CS(C)(=O)=O)C(=O)N[C@]2(CCc4cc(OCC(F)(F)F)ccc42)C3)cc1F] | B | 2.156 | 597.1 |
| I-101 | 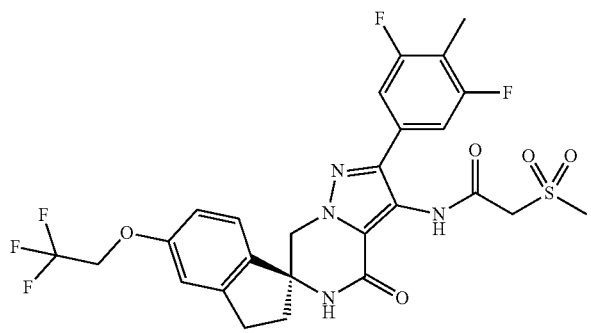 [SMILES: Cc1c(F)cc(-c2nn3c(c2NC(=O)CS(C)(=O)=O)C(=O)N[C@]2(CCc4cc(OCC(F)(F)F)ccc42)C3)cc1F] | B | 2.396 | 599.1 |

TABLE 15-continued
I-102 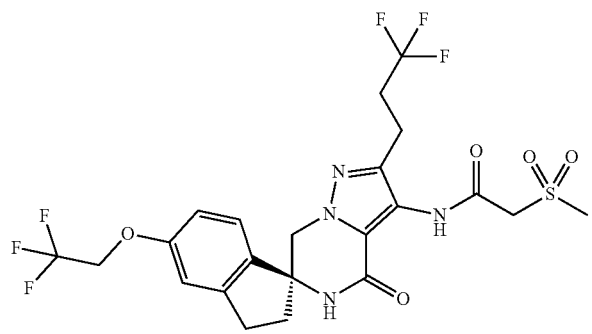 [SMILES: CS(=O)(=O)CC(=O)Nc1c(CCC(F)(F)F)nn2c1C(=O)N[C@]1(CCc3cc(OCC(F)(F)F)ccc31)C2] A 1.94 569.1
I-103 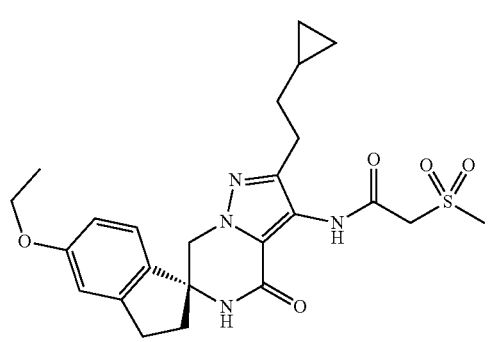 [SMILES: CCOc1ccc2c(c1)CC[C@]21Cn2nc(CCC3CC3)c(NC(=O)CS(C)(=O)=O)c2C(=O)N1] C 1.89 487.3
I-104 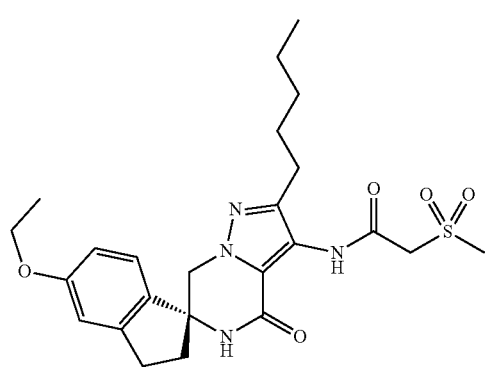 [SMILES: CCCCCc1nn2c(c1NC(=O)CS(C)(=O)=O)C(=O)N[C@@]1(CCc3cc(OCC)ccc31)C2] C 2.04 489.4
I-105 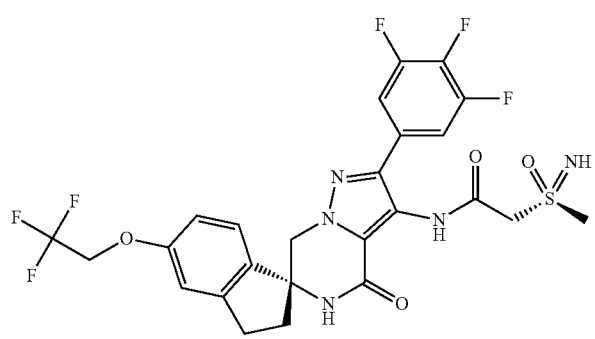 [SMILES: C[S@](=N)(=O)CC(=O)Nc1c(-c2cc(F)c(F)c(F)c2)nn2c1C(=O)N[C@@]1(CCc3cc(OCC(F)(F)F)ccc31)C2] C 2.12 602.3

TABLE 16

| | | | | |
|---|---|---|---|---|
| I-106 | (structure) | C | 2.12 | 602.3 |
| I-107 | (structure) | C | 2.13 | 600.2 |
| I-108 | (structure) | D | 1.9 | 584.2 |
| I-109 | (structure) | C | 2 | 557.3 |

TABLE 16-continued
| | | | | |
|---|---|---|---|---|
| I-110 | 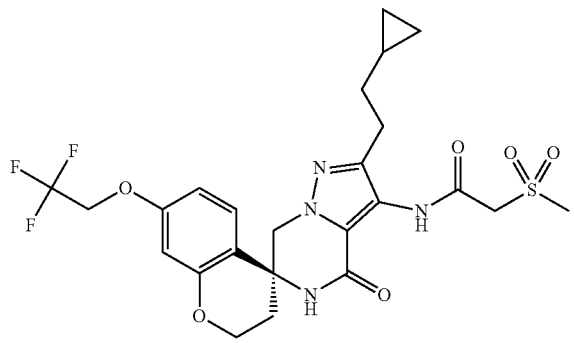 [SMILES: CS(=O)(=O)CC(=O)Nc1c(CCC2CC2)nn2c1C(=O)N[C@]1(CCOc3cc(OCC(F)(F)F)ccc31)C2] | C | 2.01 | 557.2 |
| I-111 | 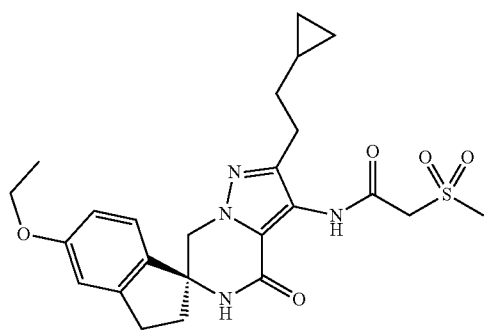 [SMILES: CCOc1ccc2c(c1)CC[C@@]21Cn2nc(CCC3CC3)c(NC(=O)CS(C)(=O)=O)c2C(=O)N1] | C | 1.89 | 487.3 |
| I-112 | 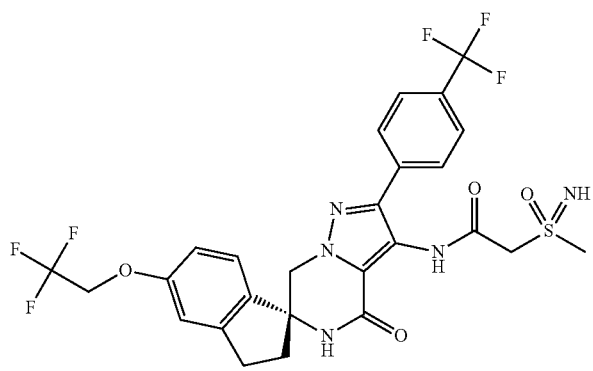 [SMILES: CS(=N)(=O)CC(=O)Nc1c(-c2ccc(C(F)(F)F)cc2)nn2c1C(=O)N[C@@]1(CCc3cc(OCC(F)(F)F)ccc31)C2] | C | 2.16 | 616.2 |
TABLE 17
| | | | | |
|---|---|---|---|---|
| I-113 | 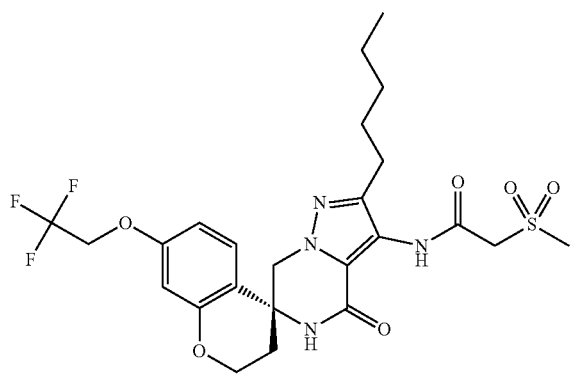 [SMILES: CCCCCc1nn2c(c1NC(=O)CS(C)(=O)=O)C(=O)N[C@@]1(CCOc3cc(OCC(F)(F)F)ccc31)C2] | C | 2.14 | 559.3 |

TABLE 17-continued
| I-114 | 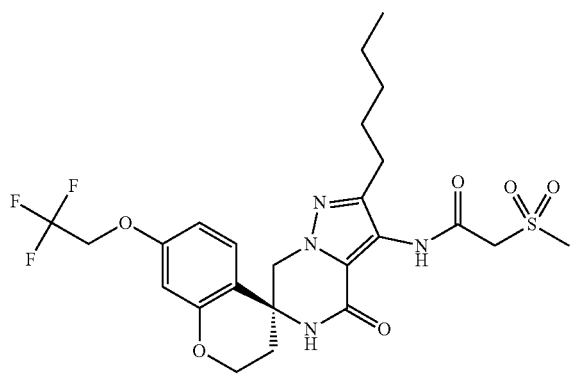 [SMILES: CCCCCc1nn2c(c1NC(=O)CS(C)(=O)=O)C(=O)N[C@]1(CCOc3cc(OCC(F)(F)F)ccc31)C2] | C | 2.14 | 559.3 |
| I-115 | 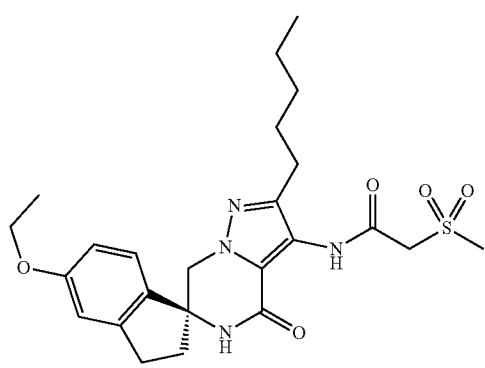 [SMILES: CCCCCc1nn2c(c1NC(=O)CS(C)(=O)=O)C(=O)N[C@]1(CCc3cc(OCC)ccc31)C2] | C | 2.04 | 489.3 |
| I-116 | 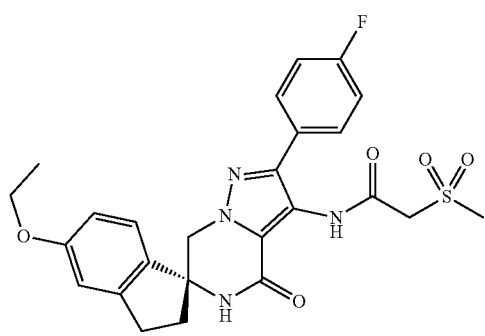 [SMILES: CCOc1ccc2c(c1)CC[C@]21Cn2nc(-c3ccc(F)cc3)c(NC(=O)CS(C)(=O)=O)c2C(=O)N1] | C | 1.95 | 513.2 |
| I-117 | 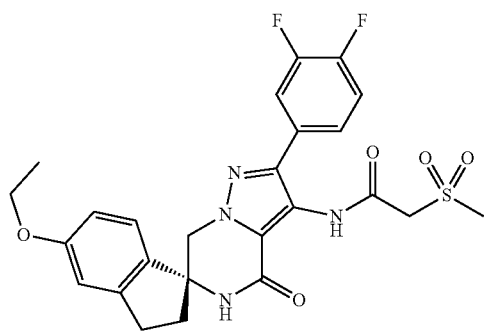 [SMILES: CCOc1ccc2c(c1)CC[C@]21Cn2nc(-c3ccc(F)c(F)c3)c(NC(=O)CS(C)(=O)=O)c2C(=O)N1] | C | 2.05 | 531.2 |

TABLE 17-continued
| I-118 | 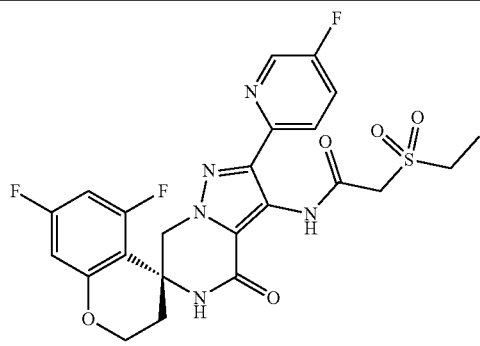 | A | 1.69 | 536.0 |
| I-119 | 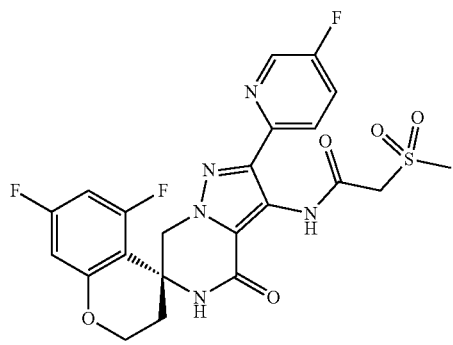 [SMILES: CS(=O)(=O)CC(=O)Nc1c(-c2ccc(F)cn2)nn2c1C(=O)N[C@@]1(CCOc3cc(F)cc(F)c31)C2] | A | 1.62 | 522.0 |
TABLE 18
| I-120 | 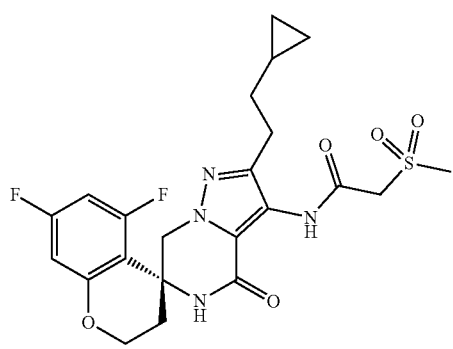 [SMILES: CS(=O)(=O)CC(=O)Nc1c(CCC2CC2)nn2c1C(=O)N[C@@]1(CCOc3cc(F)cc(F)c31)C2] | A | 1.76 | 495.1 |
| I-121 | 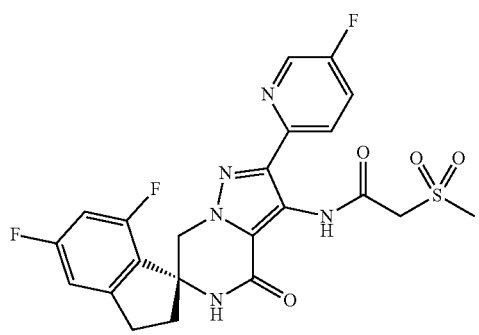 [SMILES: CS(=O)(=O)CC(=O)Nc1c(-c2ccc(F)cn2)nn2c1C(=O)N[C@@]1(CCc3cc(F)cc(F)c31)C2] | C | 1.6 | 506.3 |

TABLE 18-continued
| | | | | |
|---|---|---|---|---|
| I-122 | 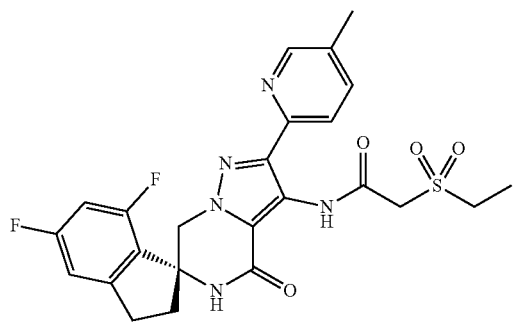 [SMILES: CCS(=O)(=O)CC(=O)Nc1c(-c2ccc(C)cn2)nn2c1C(=O)N[C@@]1(CCc3cc(F)cc(F)c31)C2] | C | 1.47 | 516.3 |
| I-123 | 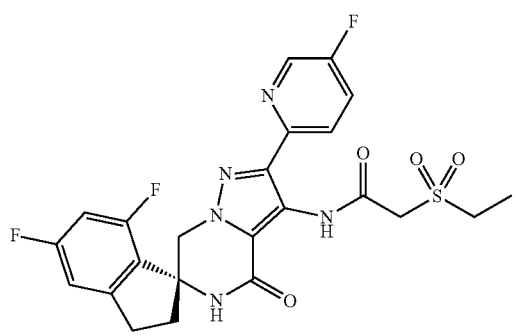 [SMILES: CCS(=O)(=O)CC(=O)Nc1c(-c2ccc(F)cn2)nn2c1C(=O)N[C@@]1(CCc3cc(F)cc(F)c31)C2] | C | 1.68 | 520.3 |
| I-124 | 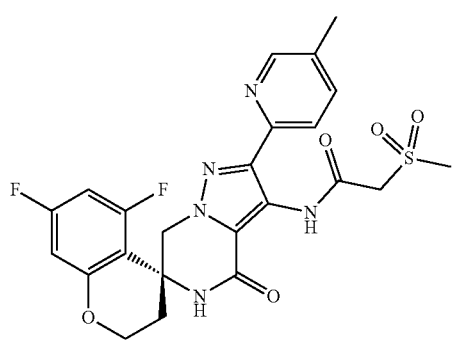 [SMILES: Cc1ccc(-c2nn3c(c2NC(=O)CS(C)(=O)=O)C(=O)N[C@@]2(CCOc4cc(F)cc(F)c42)C3)nc1] | A | 1.46 | 518.0 |
| I-125 | 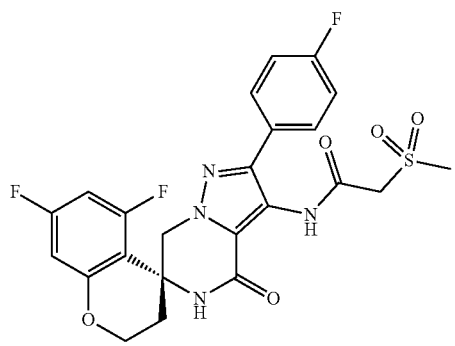 [SMILES: CS(=O)(=O)CC(=O)Nc1c(-c2ccc(F)cc2)nn2c1C(=O)N[C@@]1(CCOc3cc(F)cc(F)c31)C2] | A | 1.77 | 521.0 |

TABLE 18-continued
| I-126 | 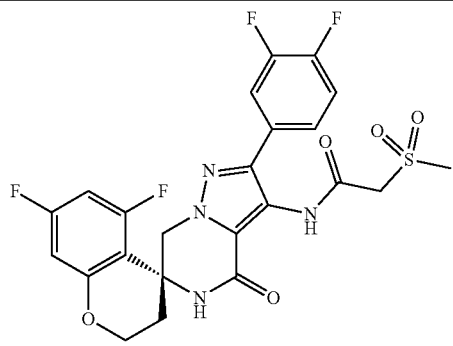 | A | 1.86 | 539.0 |
TABLE 19
| I-127 | 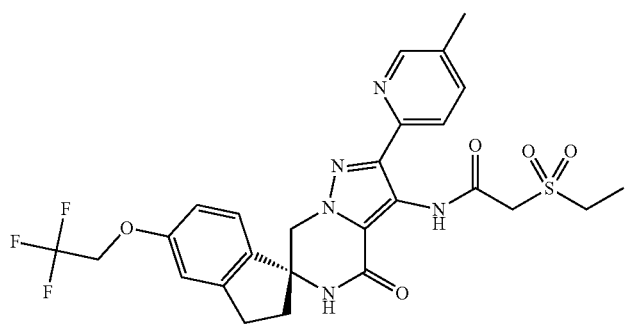 [SMILES: CCS(=O)(=O)CC(=O)Nc1c(-c2ccc(C)cn2)nn2c1C(=O)N[C@@]1(CCc3cc(OCC(F)(F)F)ccc31)C2] | D | 1.68 | 578.1 |
| I-128 | 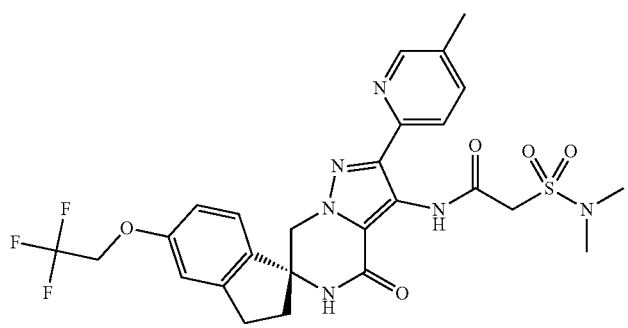 [SMILES: Cc1ccc(-c2nn3c(c2NC(=O)CS(=O)(=O)N(C)C)C(=O)N[C@@]2(CCc4cc(OCC(F)(F)F)ccc42)C3)nc1] | D | 1.7 | 593.2 |
| I-129 | 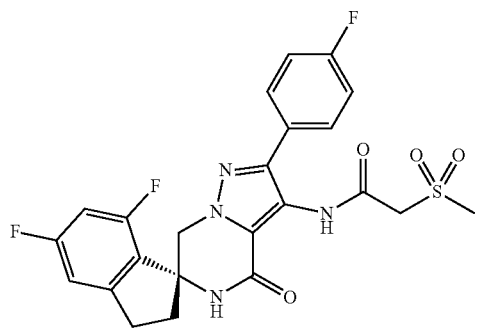 [SMILES: CS(=O)(=O)CC(=O)Nc1c(-c2ccc(F)cc2)nn2c1C(=O)N[C@@]1(CCc3cc(F)cc(F)c31)C2] | C | 1.81 | 505.3 |

TABLE 19-continued
| | | | | |
|---|---|---|---|---|
| I-130 | 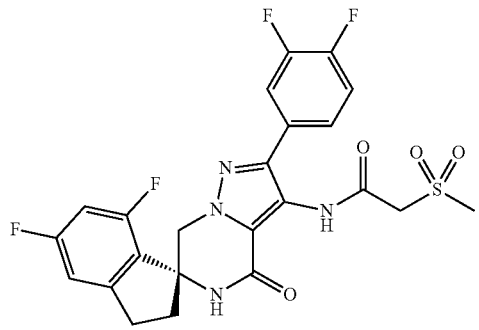 [SMILES: CS(=O)(=O)CC(=O)Nc1c(-c2ccc(F)c(F)c2)nn2c1C(=O)N[C@@]1(CCc3cc(F)cc(F)c31)C2] | C | 1.91 | 523.3 |
| I-131 | 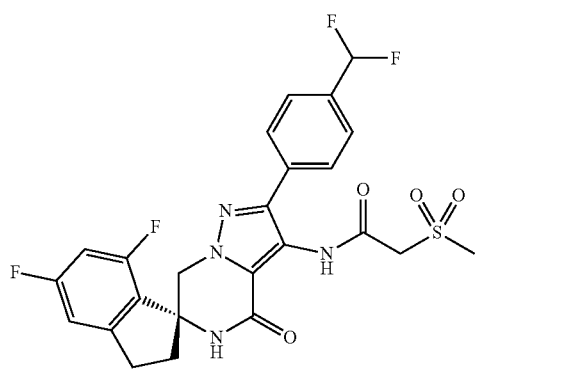 [SMILES: CS(=O)(=O)CC(=O)Nc1c(-c2ccc(C(F)F)cc2)nn2c1C(=O)N[C@@]1(CCc3cc(F)cc(F)c31)C2] | C | 1.89 | 537.3 |
| I-132 | 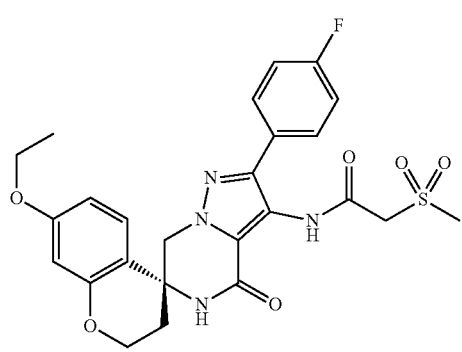 [SMILES: CCOc1ccc2c(c1)OCC[C@]21Cn2nc(-c3ccc(F)cc3)c(NC(=O)CS(C)(=O)=O)c2C(=O)N1] | C | 1.91 | 529.3 |
| I-133 | 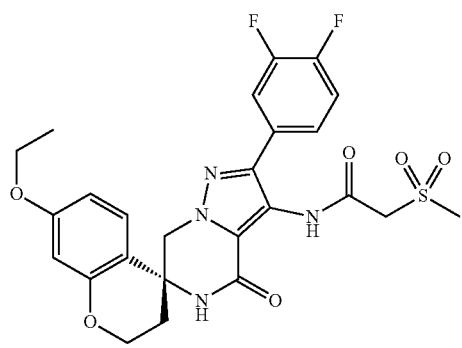 [SMILES: CCOc1ccc2c(c1)OCC[C@]21Cn2nc(-c3ccc(F)c(F)c3)c(NC(=O)CS(C)(=O)=O)c2C(=O)N1] | C | 2 | 547.3 |

TABLE 20
I-134 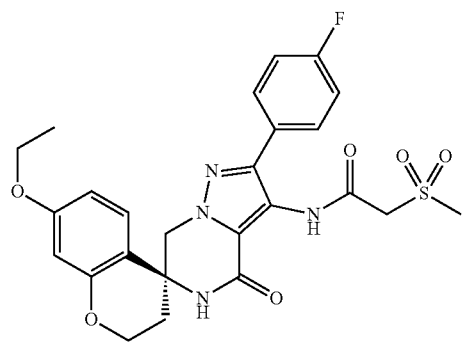 [SMILES: CCOc1ccc2c(c1)OCC[C@@]21Cn2nc(-c3ccc(F)cc3)c(NC(=O)CS(C)(=O)=O)c2C(=O)N1] C 1.9 529.3
I-135 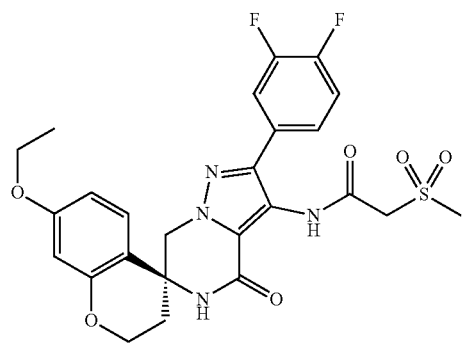 [SMILES: CCOc1ccc2c(c1)OCC[C@@]21Cn2nc(-c3ccc(F)c(F)c3)c(NC(=O)CS(C)(=O)=O)c2C(=O)N1] C 2 547.3
I-136 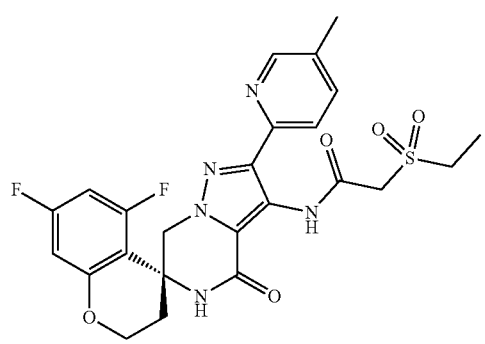 [SMILES: CCS(=O)(=O)CC(=O)Nc1c(-c2ccc(C)cn2)nn2c1C(=O)N[C@@]1(CCOc3cc(F)cc(F)c31)C2] A 1.53 532.1
I-137 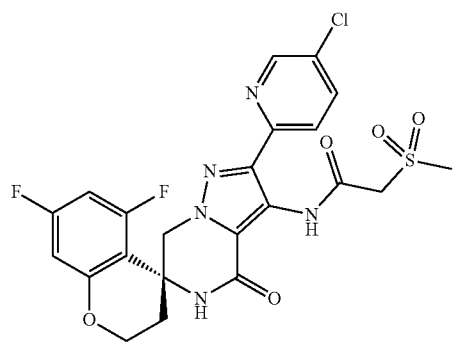 [SMILES: CS(=O)(=O)CC(=O)Nc1c(-c2ccc(Cl)cn2)nn2c1C(=O)N[C@@]1(CCOc3cc(F)cc(F)c31)C2] A 1.76 538.0

TABLE 20-continued
| I-138 | 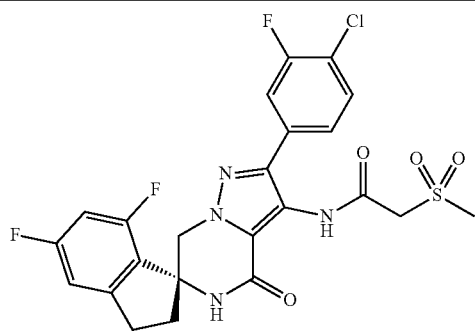 | C | 2.05 | 539.3 |
| I-139 | 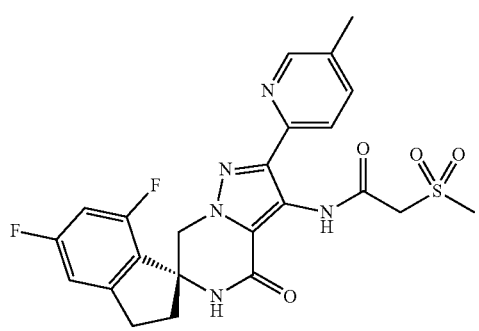 [SMILES: Cc1ccc(-c2nn3c(c2NC(=O)CS(C)(=O)=O)C(=O)N[C@@]2(CCc4cc(F)cc(F)c42)C3)nc1] | C | 1.36 | 502.3 |
| I-140 | 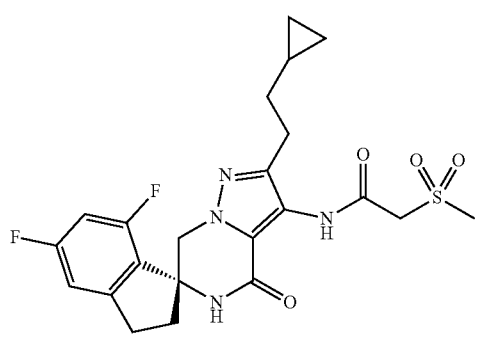 [SMILES: CS(=O)(=O)CC(=O)Nc1c(CCC2CC2)nn2c1C(=O)N[C@@]1(CCc3cc(F)cc(F)c31)C2] | C | 1.76 | 479.3 |
TABLE 21
| I-141 | 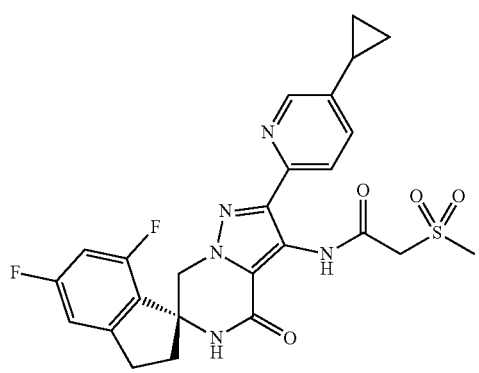 [SMILES: CS(=O)(=O)CC(=O)Nc1c(-c2ccc(C3CC3)cn2)nn2c1C(=O)N[C@@]1(CCc3cc(F)cc(F)c31)C2] | C | 1.62 | 528.3 |

TABLE 21-continued
| | | | | |
|---|---|---|---|---|
| I-142 | 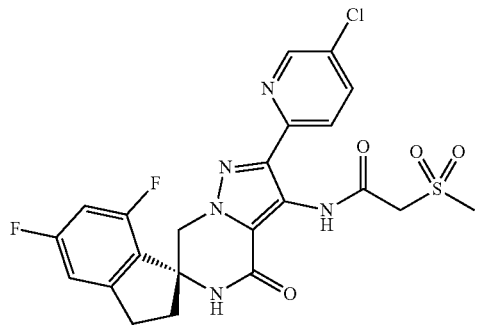 | C | 1.79 | 522.3 |
| I-143 | 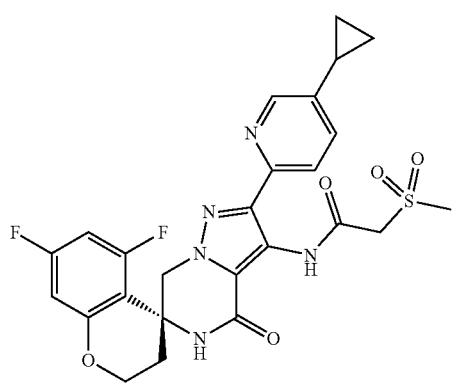 [SMILES: CS(=O)(=O)CC(=O)Nc1c(-c2ccc(C3CC3)cn2)nn2c1C(=O)N[C@@]1(CCOc3cc(F)cc(F)c31)C2] | A | 1.66 | 544.1 |
| I-144 | 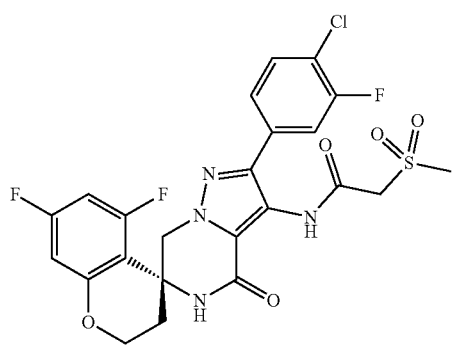 [SMILES: CS(=O)(=O)CC(=O)Nc1c(-c2ccc(Cl)c(F)c2)nn2c1C(=O)N[C@@]1(CCOc3cc(F)cc(F)c31)C2] | A | 1.96 | 555.0 |
| I-145 | 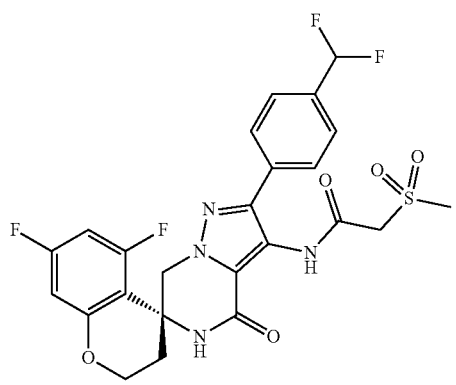 [SMILES: CS(=O)(=O)CC(=O)Nc1c(-c2ccc(C(F)F)cc2)nn2c1C(=O)N[C@@]1(CCOc3cc(F)cc(F)c31)C2] | A | 1.83 | 553.0 |

TABLE 21-continued
| I-146 | 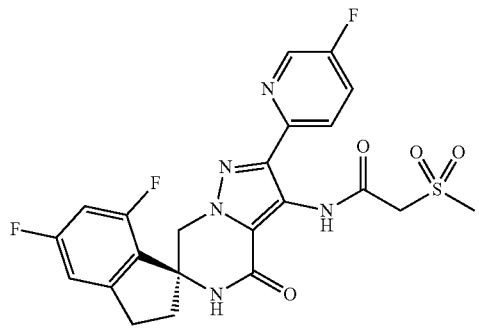 | C | 1.60 | 506.2 |
| I-147 | 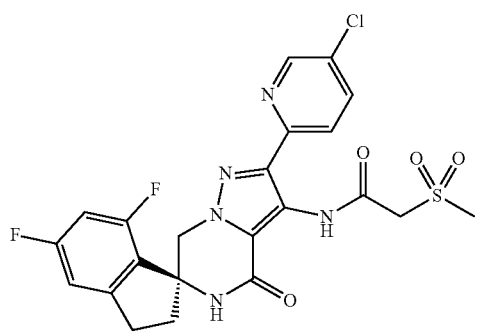 [SMILES: CS(=O)(=O)CC(=O)Nc1c(-c2ccc(F)cn2)nn2c1C(=O)N[C@]1(CCc3cc(F)cc(F)c31)C2] | C | 1.78 | 522.2 |
TABLE 22
| I-148 | 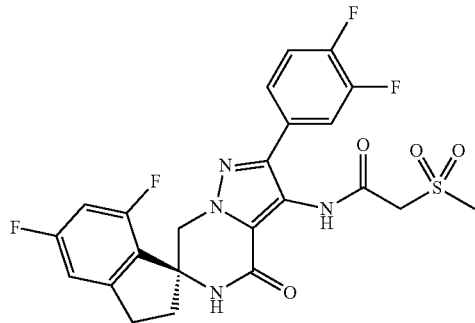 [SMILES: CS(=O)(=O)CC(=O)Nc1c(-c2ccc(F)c(F)c2)nn2c1C(=O)N[C@]1(CCc3cc(F)cc(F)c31)C2] | C | 1.90 | 523.2 |
| I-149 | 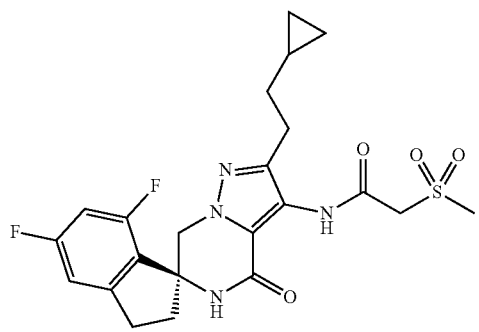 [SMILES: CS(=O)(=O)CC(=O)Nc1c(CCC2CC2)nn2c1C(=O)N[C@]1(CCc3cc(F)cc(F)c31)C2] | C | 1.76 | 479.3 |

TABLE 22-continued

| No. | Structure | | | |
|---|---|---|---|---|
| I-150 | (5-fluoropyridin-2-yl pyrazolo structure with difluoro-chromane spiro and methylsulfonyl-acetamide) | C | 1.61 | 522.1 |
| I-151 | (5-chloropyridin-2-yl analog) | C | 1.78 | 538.1 |
| I-152 | (3,4-difluorophenyl analog) | C | 1.91 | 539.1 |
| I-153 | (5-(difluoromethyl)pyridin-2-yl analog) | A | 1.73 | 554.0 |

In I-54 and I-55, an asymmetric carbon in a mother nucleus is a mixture R/S=1/1.

In I-62 and I-63, stereochemistry of a mother nucleus is single, but absolute configuration is not determined.

In I-72, I-105, I-106 and I-107, stereochemistry of sulfoximine is single, but absolute configuration is not determined.

In I-73, I-108 and I-112, stereochemistry of sulfoximine is a mixture of R/S=1/1.

TABLE 23

| No. | NMR |
|---|---|
| I-6 | 1H-NMR (CDCl3) δ: 2.26-2.34 (m, 1H), 2.38 (s, 3H), 2.53-2.59 (m, 1H), 2.94-3.09 (m, 2H), 3.23 (s, 3H), 4.12 (s, 2H), 4.32-4.40 (m, 4H), 6.05 (s, 1H), 6.85-6.89 (m, 2H), 7.26-7.29 (m, 1H), 7.57 (br-d, 1H, J = 8.2 Hz), 7.84 (d, 1H, J = 8.0 Hz), 8.47 (br-s, 1H), 10.15 (s, 1H). |

TABLE 23-continued

| No. | NMR |
|---|---|
| I-14 | 1H-NMR (CDCl3) δ: 2.28-2.36 (m, 1H), 2.52-2.57 (m, 1H), 2.95-3.11 (m, 2H), 3.34 (q, 2H, J = 10.5 Hz), 4.33-4.42 (m, 4H), 6.14 (s, 1H), 6.86-6.90 (m, 2H), 7.28 (d, 1H, J = 8.4 Hz), 8.00-8.06 (m, 2H), 8.85 (s, 1H), 9.30 (s, 1H). |
| I-46 | 1H-NMR (CDCl3) δ: 0.03-0.06 (m, 2H), 0.39-0.43 (m, 2H), 0.69-0.76 (m, 1H), 1.52-1.57 (m, 2H), 2.16-2.24 (m, 1H), 2.50-2.55 (m, 1H), 2.79-2.82 (m, 2H), 2.91-3.07 (m, 2H), 3.22 (s, 3H), 4.12-4.22 (m, 4H), 4.35 (q, 2H, J = 8.0 Hz), 6.25 (s, 1H), 6.84-6.87 (m, 2H), 7.17 (d, 1H, J = 8.4 Hz), 8.72 (s, 1H). |
| I-126 | 1H-NMR (DMSO-D6) δ: 2.01-2.07 (m, 1H), 2.18-2.23 (m, 1H), 3.14 (s, 3H), 4.19-4.38 (m, 4H), 4.72 (dd, 2H, J = 22.1, 13.6 Hz), 6.71 (d, 1H, J = 10.0 Hz), 6.87-6.93 (m, 1H), 7.44 (dd, 1H, J = 19.1, 8.7 Hz), 7.63-7.66 (m, 1H), 7.73-7.78 (m, 1H), 8.96 (s, 1H), 10.14 (s, 1H). |
| I-133 | 1H-NMR (CDCl3) δ: 1.40 (t, 3H, J = 7.0 Hz), 2.21-2.30 (m, 2H), 3.10 (s, 3H), 3.99 (q, 2H, J = 7.0 Hz), 4.09 (d, 1H, J = 14.1 Hz), 4.20-4.29 (m, 3H), 4.50 (dd, 2H, J = 22.5, 13.6 Hz), 6.41 (d, 1H, J = 2.4 Hz), 6.44 (s, 1H), 6.57 (dd, 1H, J = 8.7, 2.3 Hz), 7.19 (q, 1H, J = 8.9 Hz), 7.29 (d, 1H, J = 8.8 Hz), 7.47 (d, 1H, J = 8.5 Hz), 7.56 (t, 1H, J = 9.4 Hz), 8.99 (s, 1H). |
| I-137 | 1H-NMR (DMSO-D6) δ: 2.04-2.09 (m, 1H), 2.20-2.25 (d, 1H, J = 18.4 Hz), 3.19 (s, 3H), 4.21-4.39 (m, 4H), 4.74 (dd, 2H, J = 17.6, 13.8 Hz), 6.72 (d, 1H, J = 9.9 Hz), 6.88-6.93 (m, 1H), 7.85 (d, 1H, J = 8.5 Hz), 7.96 (dd, 1H, J = 8.6, 2.2 Hz), 8.60 (d, 1H, J = 2.0 Hz), 8.98 (s, 1H), 10.09 (s, 1H). |
| I-141 | 1H-NMR (CDCl3) δ: 0.78 (d, 2H, J = 4.8 Hz), 1.08 (d, 2H, J = 7.4 Hz), 1.94 (t, 1H, J = 4.5 Hz), 2.37-2.44 (m, 1H), 2.54-2.61 (m, 1H), 2.97-3.04 (m, 1H), 3.10-3.17 (m, 1H), 3.23 (s, 3H), 4.12 (s, 2H), 4.34 (d, 1H, J = 12.8 Hz), 4.76 (d, 1H, J = 12.8 Hz), 6.13 (s, 1H), 6.75 (t, 1H, J = 9.0 Hz), 6.86 (d, 1H, J = 7.3 Hz), 7.38 (d, 1H, J = 7.5 Hz), 7.83 (d, 1H, J = 8.2 Hz), 8.44 (s, 1H). |
| I-142 | 1H-NMR (CDCl3) δ: 2.37-2.44 (m, 1H), 2.54-2.61 (m, 1H), 2.97-3.05 (m, 1H), 3.12-3.18 (m, 1H), 3.22 (s, 3H), 4.12 (s, 2H), 4.35 (d, 1H, J = 12.9 Hz), 4.77 (d, 1H, J = 12.8 Hz), 6.17 (s, 1H), 6.75 (t, 1H, J = 9.0 Hz), 6.86 (d, 1H, J = 7.5 Hz), 7.75 (d, 1H, J = 8.4 Hz), 7.91 (d, 1H, J = 8.4 Hz), 8.60 (s, 1H), 9.77 (s, 1H). |
| I-147 | 1H-NMR (CDCl3) δ: 2.37-2.44 (m, 1H), 2.54-2.60 (m, 1H), 2.97-3.05 (m, 1H), 3.11-3.18 (m, 1H), 3.22 (s, 3H), 4.12 (s, 2H), 4.35 (d, 1H, J = 12.9 Hz), 4.77 (d, 1H, J = 12.9 Hz), 6.17 (s, 1H), 6.75 (t, 1H, J = 9.5 Hz), 6.86 (d, 1H, J = 7.3 Hz), 7.74 (dd, 1H, J = 8.5, 2.5 Hz), 7.91 (d, 1H, J = 8.5 Hz), 8.60 (d, 1H, J = 2.0 Hz), 9.77 (s, 1H). |
| I-151 | 1H-NMR (CDCl3) δ: 2.28-2.38 (m, 2H), 3.20 (s, 3H), 4.11 (s, 2H), 4.23 (t, 2H, J = 5.2 Hz), 4.39 (d, 1H, J = 13.3 Hz), 4.97 (d, 1H, J = 13.2 Hz), 6.17 (s, 1H), 6.52-6.57 (m, 2H), 7.75 (dd, 1H, J = 8.5, 2.3 Hz), 7.92 (d, 1H, J = 8.4 Hz), 8.60 (d, 1H, J = 1.9 Hz). |

Biological Test Examples for the compounds of the present invention are described below.

The compound represented by formula (I) according to the present invention may have MGAT2 inhibitory activity and may inhibit MGAT2.

Specifically, in an evaluation method described below, IC50 is preferably 100 nM or less, more preferably 50 nM or less, and even more preferably 10 nM or less.

Preparation Example 1: Preparation of Recombinant Human MGAT2

A full-length human MGAT2 gene to which a Flag-tag had been added at the N-terminal was inserted into pFastBac (from Invitrogen). A recombinant baculovirus was produced in accordance with the protocol for a Bac-to-Bac baculovirus expression system (produced by Invitrogen), and Sf-9 cells were infected therewith. The cells were collected and sonicated, and then the membrane fraction was collected through centrifugation. Western blotting analysis with an anti-Flag antibody was performed for the membrane fraction to confirm expression, and the membrane fraction was used as a recombinant human MGAT2 enzyme solution.

Test Example 1: Measurement of Human MGAT2 Inhibitory Activity

Solutions of the compounds of the present invention in DMSO were each aliquoted into 0.2-µL portions in a 384-well polystyrene microplate produced by Corning Incorporated, and 5 µL of an enzyme solution prepared with an assay buffer (100 mmol/L phosphate buffer (pH 7.4) containing 2 mmol/L DTT) and 5 µL of a substrate solution (100 mmol/L phosphate buffer (pH 7.4), 30 µmol/L 2-Oleoylglycerol, 10 µmol/L Oleoyl-CoA) were added thereto, and the resultant was stirred and centrifuged, and incubated in a moist chamber at room temperature for 1 hour. After enzymatic reaction, 50 µL of a quenching solution (containing 0.2 µmol/L Diolein-d5, 0.4% formic acid, and 50% isopropanol) containing Internal Standard (IS) was added to terminate the reaction, and the resultant was sealed in a plate produced by Shimadzu GLC Ltd., and then stirred and centrifuged, and measurement was performed by using an electrospray ionization method with a RapidFire360 and Agilent 6550 Q-TOF mass spectrometer. Diolein as a reaction product (P) of 2-Oleoylglycerol as the substrate and an ammonium adduct ion of the IS were detected, and the peak intensity ratio, P/IS, was calculated from the peak heights to evaluate the inhibitory activity. Inhibitory activities with/without addition of enzyme were defined as Control (+)/Control (−), respectively, and the respective % inhibitions were defined as 0% inhibition and 100% inhibition. The inhibitory activity was calculated from formula below with TIBCO Spotfire (produced by TIBCO Software Inc.)

Inhibitory activity (%)=[1−{Sample−Control (−)}/{Control (+)−Control (−)}]*100 where Sample indicates a peak intensity ratio: P/IS, when the compound of the present invention was added.

The inhibitory activity results of the compounds of the present invention are shown in the following table. $IC_{50}$ (nM) in the tables indicates a concentration exhibiting 50% enzyme inhibition.

TABLE 24

| No. | IC50 (nM) |
|---|---|
| 1-1 | 14 |
| 1-2 | 6.6 |
| 1-3 | 1.99 |
| 1-4 | 1.93 |
| 1-5 | 2.81 |
| 1-6 | 2.25 |
| 1-7 | 3.04 |
| 1-8 | 1.02 |
| 1-9 | 22.5 |
| 1-10 | 1.91 |
| 1-11 | 1.08 |
| 1-12 | 9.48 |
| 1-13 | 1.93 |
| 1-14 | 46.1 |
| 1-15 | 2.56 |
| 1-16 | 1.44 |
| 1-17 | 58 |
| 1-18 | 3.6 |
| 1-19 | 5.19 |
| 1-20 | 1.97 |
| 1-21 | 3.27 |
| 1-22 | 93.5 |
| 1-23 | 1.2 |
| 1-24 | 1.37 |
| 1-25 | 1.33 |
| 1-26 | 20.1 |
| 1-27 | 7.01 |
| 1-28 | 3.89 |

TABLE 24-continued

| No. | IC50 (nM) |
|---|---|
| 1-29 | 4.91 |
| 1-30 | 193 |
| 1-31 | 2.23 |
| 1-32 | 1.19 |
| 1-33 | 0.730 |
| 1-34 | 1.36 |
| 1-35 | 32.2 |
| 1-36 | 0.617 |
| 1-37 | 21.2 |
| 1-38 | 5.31 |
| 1-39 | 248 |
| 1-40 | 7.33 |
| 1-41 | 1.04 |
| 1-42 | 11.3 |
| 1-43 | 368 |
| 1-44 | 13.4 |
| 1-45 | 1.09 |
| 1-46 | 1.17 |
| 1-47 | 2.73 |
| 1-48 | 419 |
| 1-49 | 4.79 |
| 1-50 | 2.53 |
| 1-51 | 1.32 |
| 1-52 | 15.2 |
| 1-53 | 1.75 |
| 1-54 | 5.88 |
| 1-55 | 1 |
| 1-56 | 1.03 |
| 1-57 | 1.14 |
| 1-58 | 9.78 |
| 1-59 | 0.480 |
| 1-60 | 0.527 |
| 1-61 | 1.41 |
| 1-62 | 1.39 |
| 1-63 | 1.24 |
| 1-64 | 1.26 |
| 1-65 | 0.935 |
| 1-66 | 0.850 |
| 1-67 | 0.671 |
| 1-68 | 4.04 |
| 1-69 | 2.78 |
| 1-70 | 2.6 |
| 1-71 | 1.8 |
| 1-72 | 6.43 |
| 1-73 | 2.82 |
| 1-74 | 1.06 |
| 1-75 | 1.47 |
| 1-76 | 1.94 |
| 1-77 | 2.54 |
| 1-78 | 88.3 |
| 1-79 | 1.13 |
| 1-80 | 1.28 |
| 1-81 | 1.54 |
| 1-82 | 6.51 |
| 1-83 | 4.37 |
| 1-84 | 2.51 |
| 1-85 | 2.88 |
| 1-86 | 131 |
| 1-87 | 2.55 |
| 1-88 | 1.17 |
| 1-89 | 0.761 |
| 1-90 | 1.1 |
| 1-91 | 19.5 |
| 1-92 | 0.585 |
| 1-93 | 9.47 |
| 1-94 | 1.08 |
| 1-95 | 1.48 |
| 1-96 | 208 |
| 1-97 | 3.51 |
| 1-98 | 2.15 |
| 1-99 | 1.28 |
| 1-100 | 4.59 |
| 1-101 | 1.36 |
| 1-102 | 5.65 |
| 1-103 | 7.03 |
| 1-104 | 24.7 |
| 1-105 | 1.71 |
| 1-106 | 4.95 |
| 1-107 | 1.19 |
| 1-108 | 3.43 |
| 1-109 | 1.18 |
| 1-110 | 2.14 |
| 1-111 | 7.61 |
| 1-112 | 3.96 |
| 1-113 | 1.58 |
| 1-114 | 3.1 |
| 1-115 | 14.5 |
| 1-116 | 6.72 |
| 1-117 | 4.83 |
| 1-118 | 3.76 |
| 1-119 | 2.98 |
| 1-120 | 2.57 |
| 1-121 | 6.02 |
| 1-122 | 21.4 |
| 1-123 | 8.48 |
| 1-124 | 6.5 |
| 1-125 | 2.8 |
| 1-126 | 1.59 |
| 1-127 | 2.77 |
| 1-128 | 91.9 |
| 1-129 | 10 |
| 1-130 | 4.51 |
| 1-131 | 9.33 |
| 1-132 | 3.1 |
| 1-133 | 1.39 |
| 1-134 | 4.49 |
| 1-135 | 3.22 |
| 1-136 | 4.97 |
| 1-137 | 1.53 |
| 1-138 | 3.55 |
| 1-139 | 15.8 |
| 1-140 | 11.1 |
| 1-141 | 6.42 |
| 1-142 | 2.88 |
| 1-143 | 3.43 |
| 1-144 | 1.4 |
| 1-145 | 2.9 |
| 1-146 | 9.7 |
| 1-147 | 3.5 |
| 1-148 | 10.6 |
| 1-149 | 23.4 |
| 1-150 | 11.3 |
| 1-151 | 5.33 |
| 1-152 | 8.24 |
| 1-153 | 2.23 |

Test Example 2: Metabolism Stability Test

Using commercially available pooled human hepatic microsomes, the compound of the present invention was reacted for a constant time, a remaining rate was calculated by comparing a reacted sample and an unreacted sample, thereby, a degree of metabolism of the compound of the present invention in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v) solution, mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%.

(Result) Remaining rates at a compound concentration of 0.5 μmol/L are shown in the following table.

Compound I-6: 92.4%
Compound I-13: 76%
Compound I-14: 103%
Compound I-20: 74.5%
Compound I-33: 98.5%
Compound I-46: 78.1%
Compound I-58: 88.4%
Compound I-61: 95.6%
Compound I-66: 105%
Compound I-79: 77.2%
Compound I-126: 100%
Compound I-130: 94.8%
Compound I-137: 101%
Compound I-141: 99.4%
Compound I-142: 106%
Compound I-147: 89.8%
Compound I-151: 104%

Test Example 3: Solubility Test

The solubility of the compound of the present invention was determined under 1% DMSO addition conditions. 10 mmol/L solution of the compound was prepared with DMSO, and 6 μL of the solution of the compound of the present invention was added to 594 μL of pH 6.8 artificial intestinal juice (118 mL of 0.2 mol/L NaOH test solution and water were added to 250 mL of 0.2 mol/L potassium dihydrogen phosphate test solution to reach 1000 mL). The mixture was left standing for 16 hours at 25° C., and the mixture was vacuum-filtered. The filtrate was two-fold diluted with methanol/water=1/1 (V/V), and the compound concentration in the filtrate was measured with HPLC or LC/MS/MS by the absolute calibration method. The dilution concentration and the dilution solvent were changed as necessary.

(Result)
Compound I-6: >50 μmol/L
Compound I-14: 41.8 μmol/L
Compound I-46: >50 μmol/L
Compound I-58: >50 μmol/L
Compound I-66: >50 μmol/L
Compound I-79: >50 μmol/L
Compound I-126: >50 μmol/L
Compound I-130: >50 μmol/L
Compound I-137: >50 μmol/L
Compound I-141: 48.9 μmol/L
Compound I-142: >50 μmol/L
Compound I-147: >50 μmol/L
Compound I-151: >50 μmol/L Test Example 4: Phototoxicity Test An erythrocyte photohemolysis test (Wolfgang J. W. Pepe et al., ATLA29, 145-162, 2001), which is an evaluation method using effect to biomembranes and photoperoxidation as indexes, is conducted as an In vitro phototoxicity test. In this method, a solution of the compound of the present invention is prepared with dimethylsulfoxide as a medium, to which a sheep erythrocyte solution in a ratio of 2.5% (v/v) with respect to the prepared solution is added, and the thus-obtained mixed solution (concentration: 0.1 to 0.0008%) is used. The mixed solution is added to two microplates, and one of the prepared microplates is irradiated with light in UVA and UVB regions (10 J/cm$^2$, 290 to 400 nm) by using an ultraviolet fluorescence lamp (GL20SE lamp, SANKYO DENKI Co., Ltd., and, FL20S-BLB lamp, Panasonic Corporation), and subjected to centrifugation together with the microplate without irradiation with light, and then the absorbance (540 nm or 630 nm) of the supernatant is measured. To determine two indexes (effect to biomembranes and photoperoxidation) for evaluation of phototoxicity, the absorbance of the medium is subtracted from the absorbance obtained from the compound of the present invention for each of the cases with and without irradiation with light, and the thus-calculated values are used for the subsequent calculations. With respect to effect to biomembranes, a photohemolysis rate is determined from the difference in absorbance (540 nm) between the case with irradiation with light and the case without irradiation with light, and, with respect to photoperoxidation, change in absorbance (630 nm) between the case with irradiation with light and the case without irradiation with light is determined. In calculation of a photohemolysis rate, the absorbance (540 nm) obtained from a 2.5% (v/v) sheep erythrocyte solution which has been subjected to forced hemolysis with distilled water is defined as the 100% photohemolysis rate and used as a reference. It is judged to be (−) when the photohemolysis rate is less than 10% and the change in the absorbance at 630 nm is less than 0.05. It is judged to be (+) when the photohemolysis rate is 10% or more and the change in the absorbance at 630 nm is 0.05 or more.

Test Example 5: Cytotoxicity Test

Cells after being exposed to the compound are automatically counted by using the cell image analyzer Toxinsight (Thermo Fisher Scientific) to evaluate the cytotoxicity of the compound of the present invention.

HepG2 cells (derived from human liver cancer cells) are seeded in a 384-well plate at 60000 cells/mL, and a solution of the compound is added to each well after 24 hours. The solution of the compound is a solution of the compound of the present invention in DMSO (five stage dilution from maximum concentration of 50 μmol/L to minimum concentration of about 3.1 μmol/L at 2 fold ratio), and a solution consisting only of DMSO is used as a negative control, and a solution of camptothecin is used as a positive control. The solution of the compound of the present invention in DMSO, the negative control solution, or the positive control solution is added to each well. After 71 hours, a solution of Hoechst 33342 diluted with Dulbecco's phosphate buffer solution (D-PBS) to a final concentration of 1 μg/mL is added to each well, and nuclear staining is performed in an incubator at 37° C. and 5% $CO_2$ for 1 hour. After the staining, the resultant is fixed with 4% paraformaldehyde in a $CO_2$ incubator at 37° C. for 20 minutes. Finally, the wells are washed by D-PBS three times, and nuclei with development of fluorescence are counted for each well by using a Toxinsight (Thermo Fisher Scientific). Four wells are assigned for one concentration, and the mean value and variation (SD) of nucleus counts (counts of cells for which toxicity is not found) in the four wells are calculated. Comparison was made with the negative control group, and an exposure concentration to the compound ($IC_{50}$) at which the mean value was lowered to less than 50% of the mean value for the negative control was calculated. A smaller $IC_{50}$ value is rated as a higher risk of cytotoxicity.

Test Example 6: Anti-Obesity Effect Test

The anti-obesity effect of the compound of the present invention was examined by using C57BL/6j mice (DIO mice) provided with a high-fat diet (TestDiet; 58Y1).

Five-week-old male C57BL/6j mice (CLEA Japan, Inc.) were purchased, and grown with feeding of a high-fat diet under 12-hour light-dark cycles for 4 weeks to produce DIO mice. A medium (0.5% HPMC) was administered twice per day from 3 weeks before administration of the compound. Randomization was performed for grouping (n=7) on the basis of body weight and change in food consumption during the period of administration for conditioning. Forced oral administration of Example Compound or a medium (0.5% HPMC) was performed twice per day from Day 1 to Day 28. Body weight and food consumption were measured every day. Dissection was performed on Day 28, and measurement of the weight of epididymal fat and a biochemical test for the blood collected were conducted.

Test Example 7: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan 0-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by the compound of the present invention was assessed.

The reaction conditions are as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human liver microsomes 0.2 mg protein/mL; concentrations of the compound of the present invention, 1, 5, 10, 20 μmol/L (four points).

As a reaction solution, each five kinds of substrates, human liver microsomes, or compound of the present invention in 50 mmol/L Hepes buffer were added to a 96-well plate at the composition as described above, and NADPH, as a cofactor was added to initiate metabolism reactions. After the incubation at 37° C. for 15 minutes, a methanol/acetonitrile=1/1 (V/V) solution was added to stop the reaction. After the centrifugation at 3000 rpm for 15 minutes, resorufin (CYP1A2 metabolite) in the supernatant was quantified by a fluorescent multilabel counter or LC/MS/MS, and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%). Remaining activity (%) was calculated. $IC_{50}$ was calculated by reverse presumption by a logistic model using the concentration and an inhibition rate.

(Result)
Compound I-6: five kinds >20 μmol/L
Compound I-14: five kinds >20 μmol/L
Compound I-20: five kinds >20 μmol/L
Compound I-33: five kinds >20 μmol/L
Compound I-46: five kinds >20 μmol/L
Compound I-58: five kinds >20 μmol/L
Compound I-66: five kinds >20 μmol/L
Compound I-126: five kinds >20 μmol/L
Compound I-130: five kinds >20 μmol/L
Compound I-141: five kinds >20 μmol/L
Compound I-142: five kinds >20 μmol/L
Compound I-147: five kinds >20 μmol/L
Compound I-151: five kinds >20 μmol/L Test Example 8: BA Test Materials and methods for experiments to evaluate oral absorption
(1) Animals: the mice or SD rats were used.
(2) Breeding conditions: the mice or SD rats were allowed to freely take solid food and sterilized tap water.
(3) Setting of dosage and grouping: Oral administration and intravenous administration were performed with a predetermined dosage. Grouping was set as below. (dosage changed per compound)
Oral administration: 1 to 30 mg/kg (n=2 to 3)
Intravenous administration: 0.5 to 10 mg/kg (n=2 to 3)
(4) Preparation of administration solution: Oral administration was performed in the form of a suspension or a solution. Intravenous administration was performed after solubilization.
(5) Routes of administration: Oral administration was performed mandatory into the stomach by oral sonde. Intravenous administration was performed from caudal vein or femoral vein by syringes with needle.
(6) Evaluation items: blood was collected over time, and the plasma concentration of the compound of the present invention was measured by LC/MS/MS.
(7) Statistical analysis: regarding the transition of the plasma concentration of the compound of the present invention, the area under the plasma concentration-time curve (AUC) was calculated by non-linear least squares program WinNonlin (registered trademark), and the bioavailability (BA) of the compound of the present invention was calculated from the AUCs of the oral administration group and intravenous administration group.
(Result)
Compound I-6: 55.1%
Compound I-20: 63.4%
Compound I-33: 60.5%
Compound I-46: 53.1%
Compound I-58: 88.2%
Compound I-137: 49%
Compound I-141: 67%
Compound I-142: 66.2%

Test Example 9: CYP3A4 (MDZ) MBI Test

CYP3A4 (MDZ) MBI test is a test of investigating mechanism based inhibition (MBI) potential on CYP3A4 by the enhancement of inhibitory degree of a metabolic reaction caused by the compound of the present invention. CYP3A4 inhibition was evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, at pre-reaction time 1, 5, 10, 20 μmol/L (four points).

Pooled human liver microsomes and a solution of the compound of the present invention in K-Pi buffer (pH 7.4) as a pre-reaction solution were added to a 96-well plate at the composition of the pre-reaction. A part of pre-reaction solution was transferred to another 96-well plate, and 1/10 diluted by K-Pi buffer containing a substrate. NADPH as a co-factor was added to initiate a reaction as a marker reaction (without pre-reaction). After a predetermined time of a reaction, methanol/acetonitrile=1/1 (V/V) solution was added to stop the reaction. In addition, NADPH was added to a remaining pre-reaction solution to initiate a pre-reaction (with pre-reaction). After a predetermined time of a pre-reaction, a part was transferred to another plate, and 1/10 diluted by K-Pi buffer containing a substrate to initiate a reaction as a marker reaction. After a predetermined time of a reaction, methanol/acetonitrile=1/1 (V/V) solution was added in order to stop the reaction. The plate on which each index reaction had been performed was centrifuged at 3000 rpm for 15 minutes, and thereafter 1-hydroxylated midazolam in the supernatant was quantified by LC/MS/MS.

The sample adding DMSO as a solvent to a reaction system instead of a solution dissolving the compound of the present invention was adopted as a control (100%). Remaining activity (%) was calculated at each concentration of the compound of the present invention compared to a control, and IC value was calculated by reverse-presumption by a logistic model using a concentration and an inhibition rate. IC at Preincubation 0 min/IC at Preincubation 30 min was defined as a value of Shifted IC, and a case that Shifted IC was 1.5 or more was regarded as Positive, and a case that Shifted IC was 1.0 or less was regarded as Negative.
(Result)
Compound I-6: Negative
Compound I-14: Negative
Compound I-20: Negative
Compound I-46: Negative
Compound I-58: Negative
Compound I-66: Negative
Compound I-126: Negative
Compound I-130: Negative
Compound I-147: Negative
Compound I-151: Negative Test Example 10: Powder Solubility Test Appropriate quantity of the compound of the present invention was put in suitable containers. 200 µL of JP-1 solution (water was added to 2.0 g of sodium chloride and 7.0 mL of hydrochloric acid to reach 1000 mL), 200 µL of JP-2 solution (500 mL of water was added to 500 mL of phosphate buffer (pH 6.8)) or 20 mmol/L sodium taurocholate (TCA)/JP-2 solution (JP-2 solution was added to 1.08 g of TCA to reach 100 mL) was independently added to each container. When total amount was dissolved after adding the test reagent, the compound of the present invention was added appropriately. After sealing and shaking at 37° C. for 1 hour, solution was filtrated and 100 µL of methanol was added to 100 µL of each filtrate to dilute two-fold. The dilution ratio and the dilution solvent were changed as necessary. After checking that there was no bubble and deposit, the container was sealed and shaken. The compound of the present invention was measured using HPLC by absolute calibration curve method.
Compound I-46: JP-2 solution: 8.64 µmol/L Test Example 11: Fluctuation Ames Test Mutagenicity of the compound of the present invention was evaluated.

20 µL of freezing-stored rat typhoid *Bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 8.0 mL of a bacterial solution of the TA98 strain was centrifuged (2000×g, 10 minutes) to remove a culturing solution. The bacteria was suspended in 8.0 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), the suspension was added to 120 mL of an Exposure medium (Micro F buffer containing Biotin: 8 µg/mL, histidine: 0.2 µg/mL, glucose: 8 mg/mL). The TA100 strain was added to 120 mL of the Exposure medium relative to 3.1 mL of the bacterial solution to prepare a test bacterial solution. Each 12 µL of DMSO solution of the compound of the present invention (several stage dilution from maximum dose 50 mg/mL at 2 to 3 fold ratio), DMSO as a negative control, and 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µL of the test bacterial solution and 90 µL of S9 mix under the metabolism activating condition) were mixed, and this was shaking-cultured at 37° C. for 90 minutes. 230 µL of the bacterial solution exposed to the compound of the present invention was mixed with 1150 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which had obtained the proliferation ability by mutation of an amino acid (histidine) synthesizing enzyme gene turns from purple to yellow due to a pH change, the bacterium proliferation well which had turned to yellow in 48 wells per dose was counted, and was assessed by comparing with a negative control group. (−) and (+) means negative and positive in mutagenicity respectively.
Compound I-33: (−)

Test Example 12: hERG Test

For the purpose of assessing risk of an electrocardiogram QT interval prolongation of the compound of the present invention, effects of the compound of the present invention on delayed rectifier $K^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion BIoscience A/S), $I_{Kr}$ induced by application of a leak potential of −50 mV followed by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, $CaCl_2$): 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition of tail peak current for the compound of the present invention relative to the tail peak current after application of the vehicle is calculated to assess influence of the compound of the present invention on $I_{Kr}$.

(Result) % inhibition was shown at 10 μmol/L of test compound.

Compound I-20: 27.8%
Compound I-33: 21.3%
Compound I-66: 14.6%
Compound I-79: 25.5%
Compound I-14: 25.5%
Compound I-126: 14.2%
Compound I-130: 15.4%
Compound I-137: 23.6%
Compound I-141: 14.0%
Compound I-142: 10.6%
Compound I-147: 21.6%
Compound I-151: 25.8%

Test Example 13: (Solution Stability Test)

The compound of the present invention (0.4 mg) was weighed into a 4 mL screw vial, and 2 mL of various media pH=1 (0.1 N HClaq.+30% MeCN), pH=7 (pH 7 phosphate Buffer (100 mM+30% MeCN) or pH=9 (pH 9 carbonate Buffer (100 mM+30% MeCN) was added, respectively. Complete dissolution was confirmed. If not dissolved, filtration was performed with a 0.45 μm filter. The solution or filtrate was placed in an HPLC vial. HPLC sample cooler was set at 40° C., and sequence was set so that sampling was performed by HPLC at 0, 3, 6, 9, 12, 15, and 18 hours. Stability over time was evaluated by setting the area value of 0 hr product to 100%.

(Result)
Residual rate of Compound I-3 at 40° C., 18 hr: 100.2% at pH=1, 100.9% at pH=7, 100.2% at pH=9

Formulation Example

The compound of the present invention can be administered as a pharmaceutical composition by any conventional route, in particular enterally, for example, orally, for example, in the form of tablets or capsules, or parenterally, for example, in the form of injectable solutions or suspensions, topically, for example, in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets, granules, or capsules containing excipients, disintegrants, binders, lubricants and the like and active ingredients. Compositions for injection can be solutions or suspension, may be sterilized, and may contain preservatives, stabilizers, buffering agents, and the like.

INDUSTRIAL APPLICABILITY

Since the compounds of the present invention have MGAT2 inhibitory activity, they are useful as a medicine for MGAT2-associated diseases including obesity, metabolic syndrome, hyperlipidemia, hypertriglyceridemia, hyper-VLDL-triglyceridemia, hyperfattyacidemia, diabetes mellitus, and arteriosclerosis.

The invention claimed is:

1. A compound represented by formula (I):

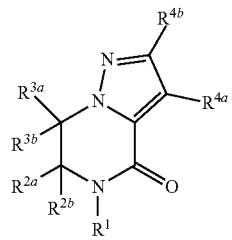

wherein $R^1$ is hydrogen;

$R^{2a}$ and $R^{2b}$ are taken together with an adjacent carbon atom to form ring B;

ring B is represented by formula:

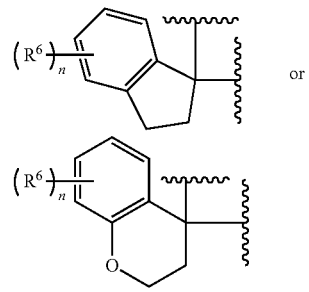

wherein $R^6$s are each independently halogen, or substituted or unsubstituted alkyloxy, and n is 1 or 2;

$R^{3a}$ is hydrogen;

$R^{3b}$ is hydrogen;

$R^{4a}$ is a group represented by formula:

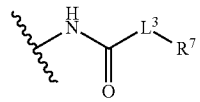

wherein $L^3$ is a single bond or substituted or unsubstituted alkylene, $R^7$ is halogen, substituted or unsubstituted sulfamoyl, substituted or unsubstituted alkyloxy, substituted or unsubstituted alkylsulfonyl, substituted or unsubstituted aromatic heterocyclyl, substituted or unsubstituted non-aromatic heterocyclyl, or a group represented by formula: $-S(=O)(=N-R^N)-R^{S1}$, $R^N$ is hydrogen, and $R^{S1}$ is substituted or unsubstituted alkyl; and $R^{4b}$ is substituted or unsubstituted alkyl, substituted or unsubstituted aromatic carbocyclyl, or substituted or unsubstituted aromatic heterocyclyl, or its pharmaceutically acceptable salt.

2. The compound or its pharmaceutically acceptable salt according to claim 1, wherein ring B is represented by any one of formulas:

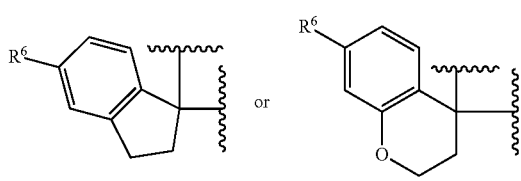

wherein R⁶s are each independently substituted or unsubstituted alkyloxy.

3. The compound or its pharmaceutically acceptable salt according to claim 1, wherein ring B is represented by any one of formulas:

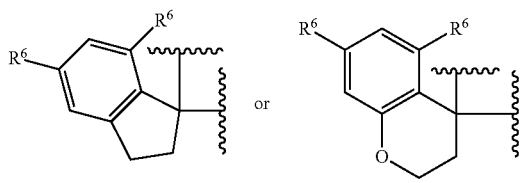

wherein R⁶s are each independently halogen, or substituted or unsubstituted alkyloxy.

4. The compound or its pharmaceutically acceptable salt according to claim 1, wherein $L^3$ is substituted or unsubstituted alkylene, and $R^7$ is halogen, substituted or unsubstituted sulfamoyl, substituted or unsubstituted alkyloxy, substituted or unsubstituted alkylsulfonyl, or a group represented by formula:

—S(=O)(=N—R$^N$)—R$^{s1}$.

5. The compound or its pharmaceutically acceptable salt according to claim 1, wherein $L^3$ is a single bond, and $R^7$ is substituted or unsubstituted aromatic heterocyclyl, or substituted or unsubstituted non-aromatic heterocyclyl.

6. The compound or its pharmaceutically acceptable salt according to claim 1, wherein the compound is selected from the group consisting of Compounds I-006, I-013, I-014, I-020, I-033, I-046, I-058, I-061, I-066, I-079, I-123, I-124, I-126, I-130, I-133, I-136, I-137, I-139, I-141, I-142, I-143, I-145, and I-147, I-151 and I-153:

I-006

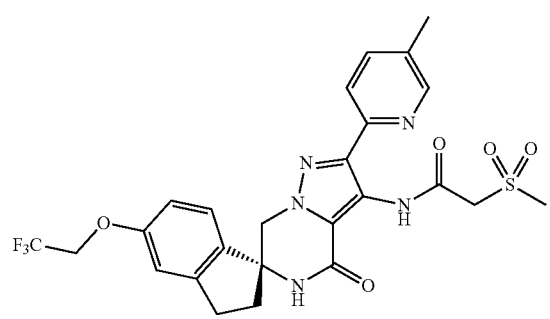

I-013

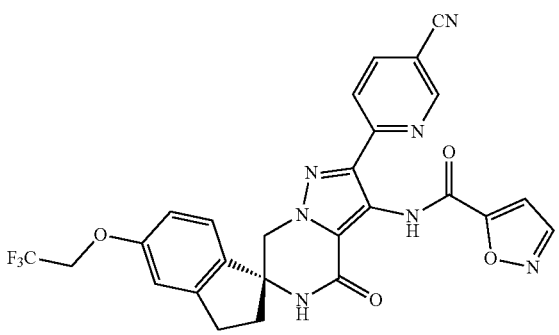

I-014

I-020

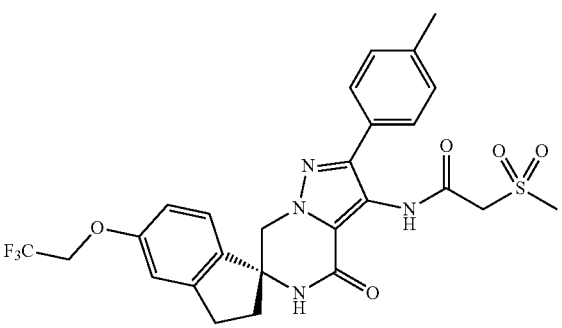

I-033

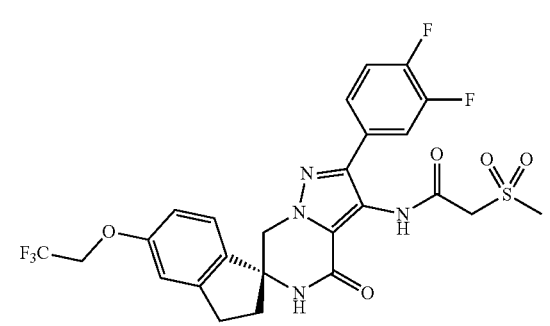

I-046
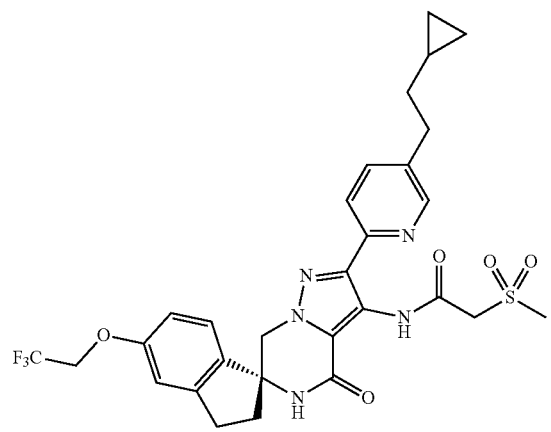
I-058
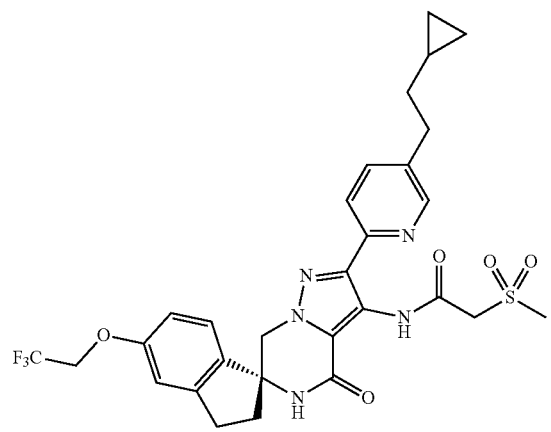
I-061
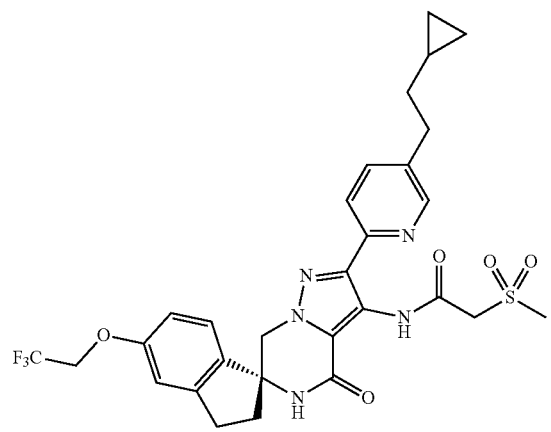
I-066
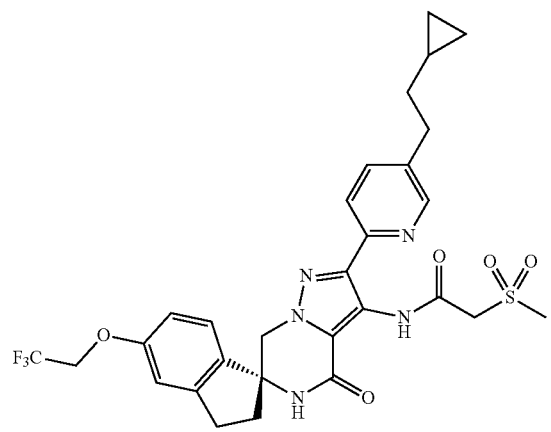
I-079
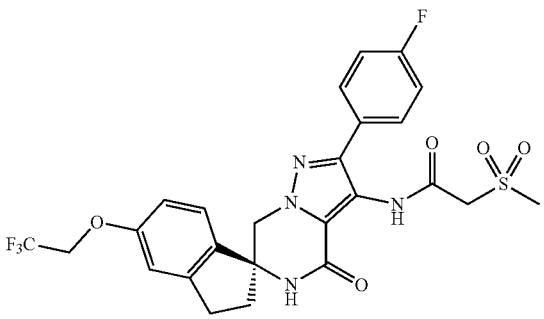
I-123
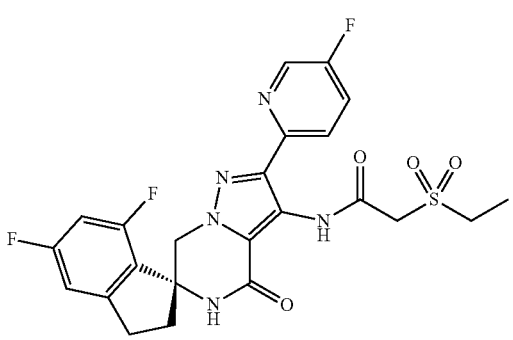
I-124
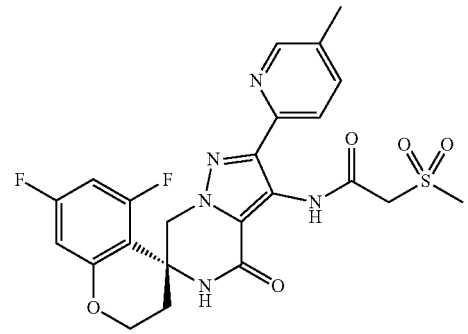
I-126
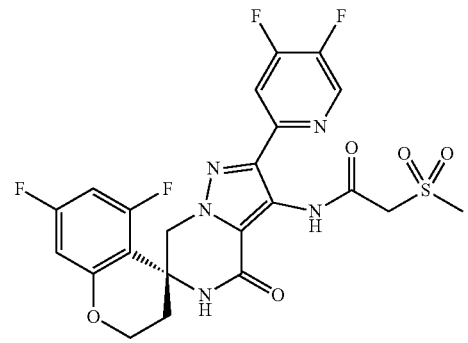

-continued
I-130
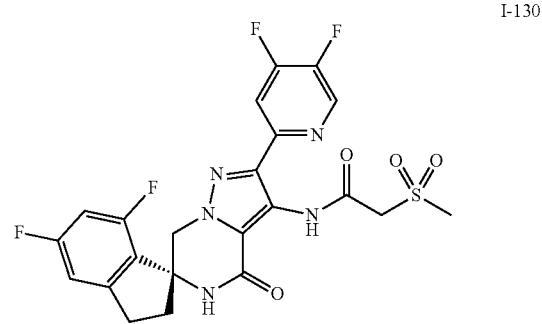
I-133
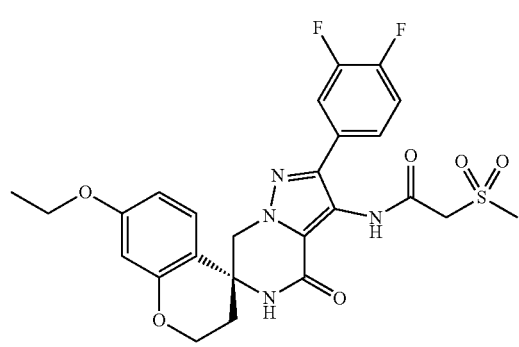
I-136
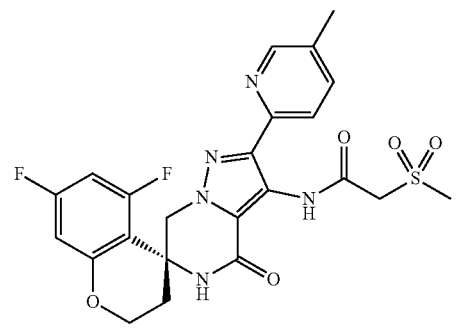
I-137
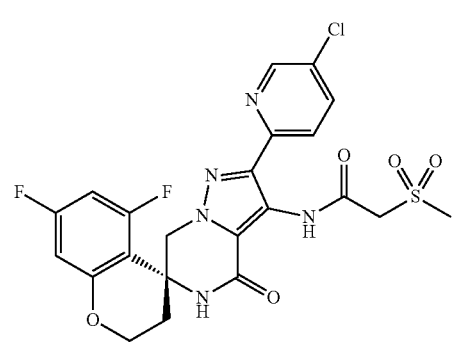
I-139
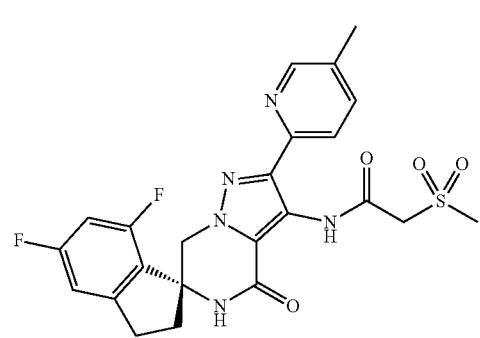
-continued
I-141
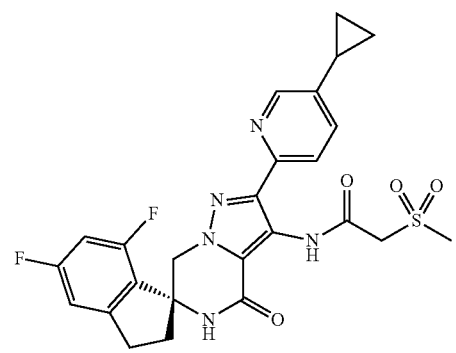
I-142
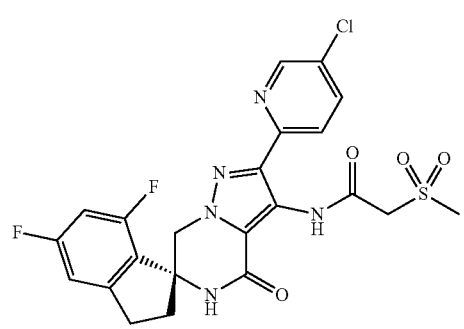
I-143
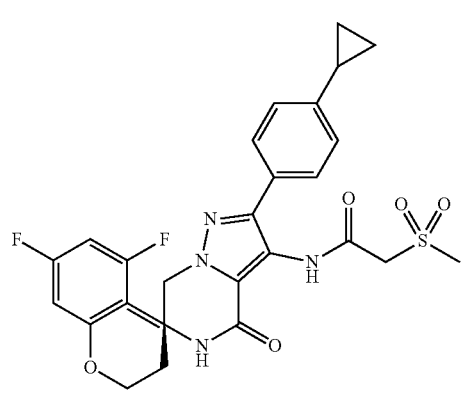
I-145
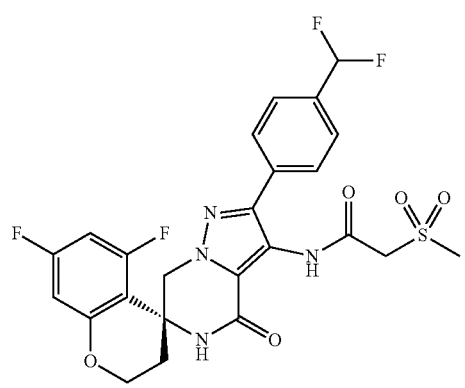

-continued

I-147

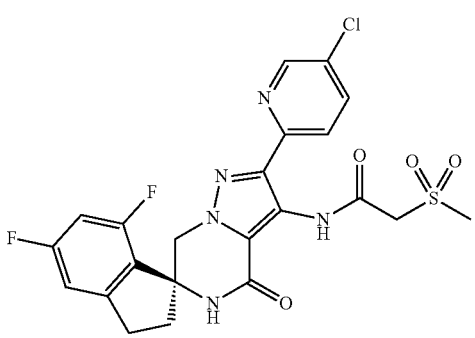

I-151

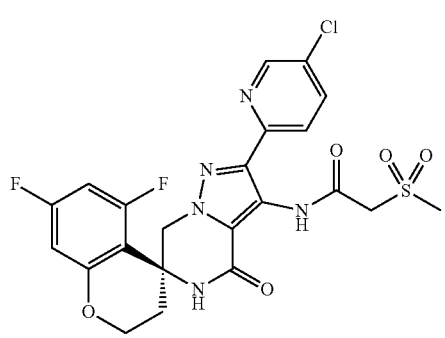

I-153

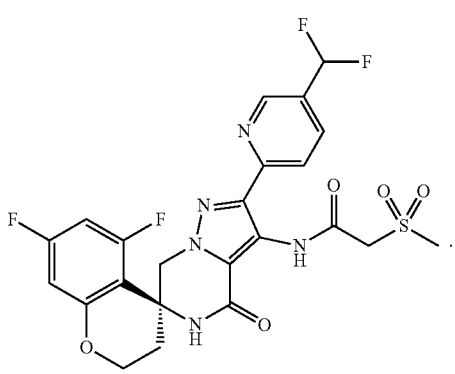

7. A pharmaceutical composition comprising the compound or its pharmaceutically acceptable salt according to claim 1 and a pharmaceutical additive.

8. A method for treating or preventing an MGAT2-associated disease, comprising administering an effective amount of the compound or its pharmaceutically acceptable salt according to claim 1 to a patient in need thereof.

9. A method for treating or preventing obesity, metabolic syndrome, hyperlipidemia, hypertriglyceridemia, hyper-VLDL-triglyceridemia, hyperfattyacidemia, diabetes mellitus, or arteriosclerosis, comprising administering an effective amount of the compound or its pharmaceutically acceptable salt according to claim 1 to a patient in need thereof.

10. A compound represented by formula (I):

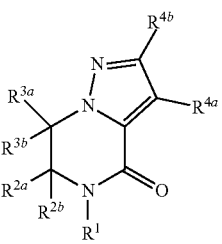

(I)

wherein $R^1$ is hydrogen, hydroxy, substituted or unsubstituted carbamoyl, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocycly-loxycarbonyl, substituted or unsubstituted non-aromatic carbocyclyloxycarbonyl, substituted or unsubstituted aromatic heterocyclyloxycarbonyl, substituted or unsubstituted non-aromatic heterocycly-loxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$R^{2a}$ is a group represented by formula:

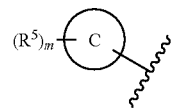

wherein ring C is an aromatic carbocycle, an aromatic heterocycle, a non-aromatic carbocycle, or a non-aromatic heterocycle;

$R^5$s are each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$—$R^{S1}$, and m is an integer of 1 to 5, $R^{2b}$ is substituted or unsubstituted alkyl, or $R^{2a}$ and $R^{2b}$ may be taken together with an adjacent carbon atom to form ring B, ring B is a substituted or unsubstituted non-aromatic carbocycle or a substituted or unsubstituted non-aromatic heterocycle;

$R^{3a}$ is hydrogen, $R^{3b}$ is hydrogen, $R^{4a}$ is a group represented by formula:

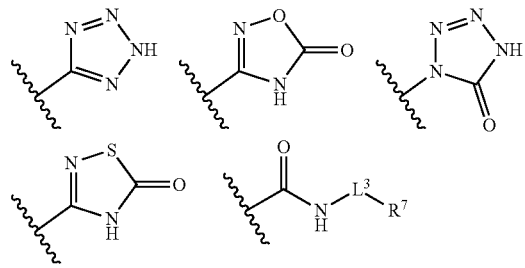

-continued

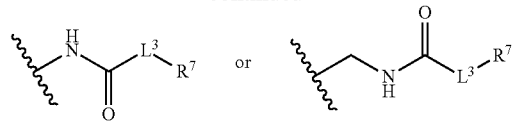

$L^3$ is a single bond or substituted or unsubstituted alkylene, $R^7$ is hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$, provided that, when L$^3$ is a single bond, R$^7$ is not hydrogen or halogen, R$^{4b}$ is halogen, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—R$^{S1}$)—R$^{S2}$, a group represented by formula: —L—S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$, L is each independently a single bond, alkylene, or C(=O), R$^{S1}$ and R$^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or R$^{S1}$ and R$^{S2}$ bonding to the same sulfur atom may be taken together with the sulfur atom to form a substituted or unsubstituted non-aromatic heterocycle;

R$^N$s are each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl, or its pharmaceutically acceptable salt.

11. The compound or its pharmaceutically acceptable salt according to claim 10, wherein ring B is represented by any one of formulas:

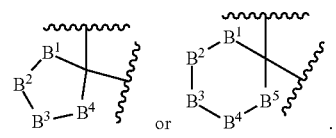

wherein

B$^1$ is CR$^{11a}$R$^{11b}$, NR$^{11c}$, O, or S,
B$^2$ is CR$^{12a}$R$^{12b}$, NR$^{12c}$, O, or S,
B$^3$ is CR$^{13a}$R$^{13b}$, NR$^{13c}$, O, or S,
B$^4$ is CR$^{14a}$R$^{14b}$, NR$^{14c}$, O, or S, and
B$^5$ is CR$^{15a}$R$^{15b}$, NR$^{15c}$, O, or S, R$^{11a}$, R$^{12a}$, R$^{13a}$, R$^{14a}$, and R$^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11b}$, $R^{12b}$, $R^{13b}$, $R^{14b}$ and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, $R^{11c}$, $R^{12c}$, $R^{13c}$, $R^{14c}$, and $R^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or, $R^{11a}$ and $R^{12a}$, $R^{12a}$ and $R^{13a}$, $R^{13a}$ and $R^{14a}$, and/or $R^{14a}$ and $R^{15a}$ may be taken together with adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and/or, $R^{11c}$ and $R^{12a}$, $R^{11c}$ and $R^{12c}$, $R^{12c}$ and $R^{11a}$, $R^{12c}$ and $R^{13a}$, $R^{12c}$ and $R^{13c}$, $R^{13c}$ and $R^{12a}$, $R^{13c}$ and $R^{14a}$, $R^{13c}$ and $R^{14c}$, $R^{14c}$ and $R^{13a}$, $R^{14c}$ and $R^{15a}$, $R^{14c}$ and $R^{15c}$, and/or, $R^{15c}$ and $R^{14a}$ may be taken together with adjacent atoms to form a substituted or unsubstituted aromatic heterocycle or a substituted or unsubstituted non-aromatic heterocycle, and/or, $R^{11a}$ and $R^{13a}$, $R^{11a}$ and $R^{13c}$, $R^{11a}$ and $R^{14a}$, $R^{11a}$ and $R^{14c}$, $R^{11a}$ and $R^{14c}$, $R^{11a}$ and $R^{15a}$, $R^{11a}$ and $R^{15c}$, $R^{11c}$ and $R^{13a}$, $R^{11c}$ and $R^{13c}$, $R^{11c}$ and $R^{14a}$, $R^{11c}$ and $R^{14c}$, $R^{11c}$ and $R^{15a}$, $R^{11c}$ and $R^{15c}$, $R^{12a}$ and $R^{14a}$, $R^{12a}$ and $R^{14c}$, $R^{12a}$ and $R^{15a}$, $R^{12a}$ and $R^{15c}$, $R^{12c}$ and $R^{14a}$, $R^{12c}$ and $R^{14c}$, $R^{12c}$ and $R^{15a}$, $R^{12c}$ and $R^{15c}$, $R^{13a}$ and $R^{15a}$, $R^{13a}$ and $R^{15c}$, $R^{13c}$ and $R^{15a}$, and/or $R^{13c}$ and $R^{15c}$ may be taken together to form a C2-C4 bridge optionally containing heteroatom(s), and/or, $R^{11b}$ and $R^{12b}$, $R^{11b}$ and $R^{12c}$, $R^{11c}$ and $R^{12b}$, $R^{11c}$ and $R^{12c}$, $R^{12b}$ and $R^{13b}$, $R^{12b}$ and $R^{13c}$, $R^{12c}$ and $R^{13b}$, $R^{12c}$ and $R^{13c}$, $R^{13b}$ and $R^{14b}$, $R^{13b}$ and $R^{14c}$, $R^{13c}$ and $R^{14b}$, $R^{13c}$ and $R^{14c}$, $R^{14b}$ and $R^{15b}$, $R^{14b}$ and $R^{15c}$, $R^{14c}$ and $R^{15b}$, and/or $R^{14c}$ and $R^{15c}$ may be taken together to form a bond, and other symbols are as described in claim 10.

12. The compound or its pharmaceutically acceptable salt according to claim 10, wherein ring B is represented by any one of formulas:

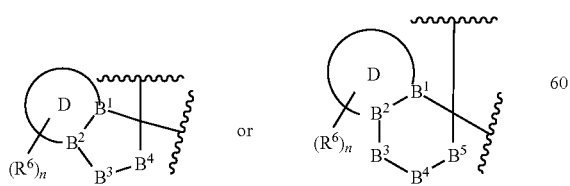

wherein $B^1$ is C, $CR^{11a}$ or N, $B^2$ is C, $CR^{12a}$ or N, $B^3$ is $CR^{13a}R^{13b}$, $NR^{13c}$, O or S, $B^4$ is $CR^{14a}R^{14b}$, $NR^{14c}$, O or S, $B^5$ is $CR^{15a}R^{15b}$, $NR^{15c}$, O or S, $R^{11a}$, $R^{12a}$, $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—$R^{N}$)—$R^{S1}$, a group represented by formula: —N=S(=N—$R^{N}$)(—$R^{S1}$)—$R^{S2}$, or a group represented by formula: —S(=N—$R^{N}$)$_2$—$R^{S1}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—R$^{S1}$)—R$^{S2}$, a group represented by formula: —L—S(=O)(=N—R$^{N}$)—R$^{S1}$, a group represented by formula: —N=S(=N—R$^{N}$)(—R$^{S1}$)—R$^{S2}$, or a group represented by formula: —S(=N—R$^{N}$)$_2$—R$^{S1}$, R$^{13c}$, R$^{14c}$, and R$^{15c}$ are each independently hydrogen, cyano, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, and/or, R$^{11a}$ and R$^{13a}$, R$^{11a}$ and R$^{13c}$, R$^{11a}$ and R$^{14a}$, R$^{11a}$ and R$^{14c}$, R$^{11a}$ and R$^{15a}$, R$^{11a}$ and R$^{15c}$, R$^{12a}$ and R$^{14a}$, R$^{12a}$ and R$^{14c}$, R$^{12a}$ and R$^{15a}$, R$^{12a}$ and R$^{15c}$, R$^{13a}$ and R$^{15a}$, R$^{13a}$ and R$^{15c}$, R$^{13c}$ and R$^{15a}$, and/or R$^{13c}$ and R$^{15c}$ may be taken together to form a C2-C4 bridge optionally containing heteroatom(s), and/or, R$^{11a}$ and R$^{12a}$, R$^{12a}$ and R$^{13b}$, R$^{12a}$ and R$^{13c}$, R$^{13b}$ and R$^{14b}$, R$^{13b}$ and R$^{14c}$, R$^{13c}$ and R$^{14b}$, R$^{13c}$ and R$^{14c}$, R$^{14b}$ and R$^{15b}$, R$^{14b}$ and R$^{15c}$, R$^{14c}$ and R$^{15b}$, and/or R$^{14c}$ and R$^{15c}$ may be taken together to form a bond, ring D is an aromatic carbocycle, a non-aromatic carbocycle, an aromatic heterocycle, or a non-aromatic heterocycle, R$^6$s are each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—$R^{S1}$)—$R^{S2}$, a group represented by formula: —L—S(=O)(=N—$R^N$)—$R^{S1}$, a group represented by formula: —N=S(=N—$R^N$)(—$R^{S1}$)—$R^{S2}$, or a group represented by formula: —S(=N—$R^N$)$_2$—$R^{S1}$, n is an integer of 1 to 4, and other symbols are as described in claim 10.

13. The compound or its pharmaceutically acceptable salt according to claim 12, wherein ring B is represented by any one of formulas:

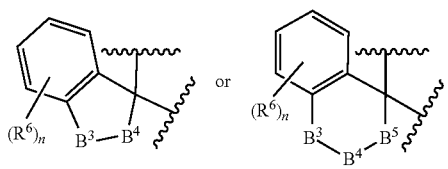

wherein $B^3$, $B^4$, $B^5$, $R^6$ and n are as described in claim 12.

14. The compound or its pharmaceutically acceptable salt according to claim 13, wherein ring B is represented by any one of formulas:

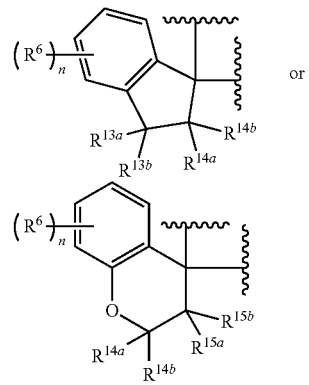

wherein $R^{13a}$, $R^{14a}$, and $R^{15a}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—R$^{S1}$)—R$^{S2}$, a group represented by formula: —L—S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$, $R^{13b}$, $R^{14b}$, and $R^{15b}$ are each independently hydrogen, halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—R$^{S1}$)—R$^{S2}$, a group represented by formula: —L—S(=O)(=N—R$^N$)—R$^{S1}$, a group represented by formula: —N=S(=N—R$^N$)(—R$^{S1}$)—R$^{S2}$, or a group represented by formula: —S(=N—R$^N$)$_2$—R$^{S1}$, and/or, $R^{13b}$ and $R^{14b}$ or $R^{14b}$ and $R^{15b}$ may be taken together to form a bond, $R^6$s are each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkyloxy, substituted or unsubstituted alkenyloxy, substituted or unsubstituted alkylcarbonyloxy, substituted or unsubstituted alkenylcarbonyloxy, substituted or unsubstituted alkylcarbonyl, substituted or unsubstituted alkenylcarbonyl, substituted or unsubstituted alkyloxycarbonyl, substituted or unsubstituted alkenyloxycarbonyl, substituted or unsubstituted alkylsulfanyl, substituted or unsubstituted alkenylsulfanyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by formula: —L—N=S(=O)(—R$^{S1}$)—R$^{S2}$, a group represented by formula: —L—S(=O)(=N—R$^{N}$)—R$^{S1}$, a group represented by formula: —N=S(=N—R$^{N}$)(—R$^{S1}$)—R$^{S2}$, or a group represented by formula: —S(=N—R$^{N}$)$_2$—R$^{S1}$, and n is an integer of 1 to 4.

15. The compound or its pharmaceutically acceptable salt according to claim 12, wherein R$^6$s is each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl.

16. The compound or its pharmaceutically acceptable salt according to claim 10, wherein ring C is an aromatic carbocycle or an aromatic heterocycle, R$^6$s are each independently halogen, cyano, hydroxy, substituted or unsubstituted amino, substituted or unsubstituted alkyl, substituted or unsubstituted alkyloxy, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted non-aromatic heterocyclyloxy, substituted or unsubstituted non-aromatic carbocyclylsulfonyl, or substituted or unsubstituted non-aromatic heterocyclylsulfonyl, and m is 1 to 3.

17. The compound or its pharmaceutically acceptable salt according to claim 10, wherein L$^3$ is substituted or unsubstituted alkylene, and R$^7$ is halogen, substituted or unsubstituted sulfamoyl, substituted or unsubstituted alkyl, substituted or unsubstituted alkyloxy, substituted or unsubstituted alkylsulfonyl, or a group represented by formula: —L—S(=O)(=N—R$^{N}$)—R$^{S1}$.

18. The compound or its pharmaceutically acceptable salt according to claim 10, wherein L$^3$ is a single bond, and R$^7$ is substituted or unsubstituted aromatic heterocyclyl, or substituted or unsubstituted non-aromatic heterocyclyl.

19. The compound or its pharmaceutically acceptable salt according to claim 10, wherein R$^{4b}$ is substituted or unsubstituted alkyl, substituted or unsubstituted aromatic carbocyclyl, or substituted or unsubstituted aromatic heterocyclyl.

20. The compound or its pharmaceutically acceptable salt according to claim 1, wherein ring B is represented by formula:

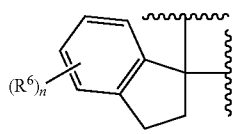

or

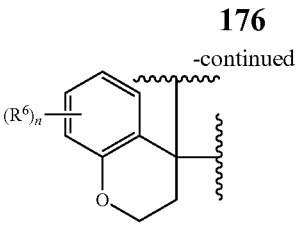

or wherein R$^6$s are each independently halogen, alkyloxy, or haloalkyloxy and n is 1 or 2, L$^3$ is alkylene or alkylene substituted with halogen, R$^7$ is halogen or alkylsulfonyl, R$^{4b}$ is substituted or unsubstituted phenyl, or substituted or unsubstituted 6 membered aromatic heterocyclyl, wherein when R$^{4b}$ is substituted, the substituents are one or more groups selected from the group consisting of halogen, cyano, alkyl, haloalkyl, and cyclopropanyl.

21. The compound or its pharmaceutically acceptable salt according to claim 1, wherein the compound is selected from the group consisting of:

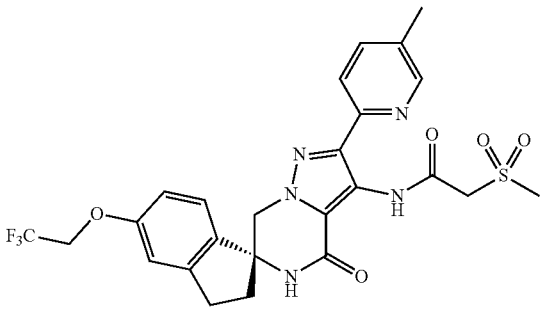

I-006

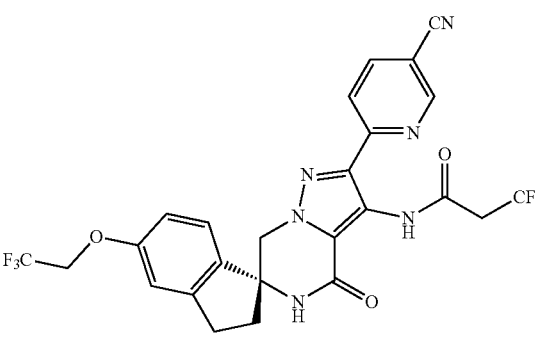

I-014

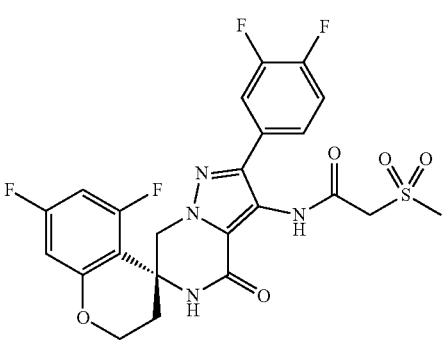

I-126

-continued
I-133
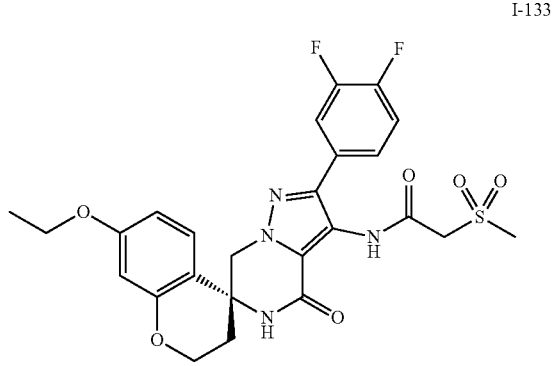
I-121
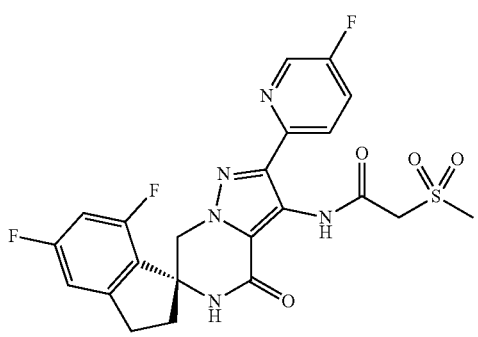
I-142
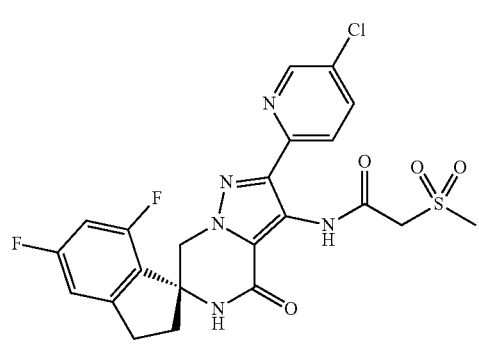
I-123
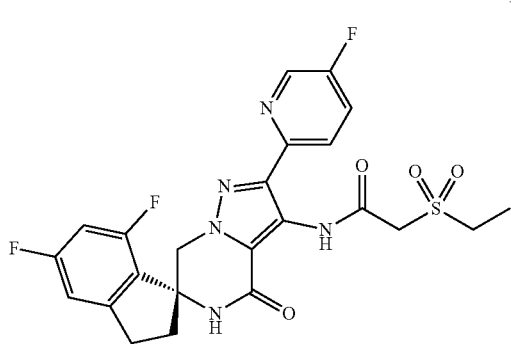
I-147
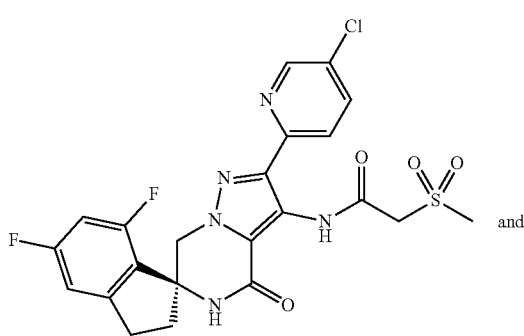
and
I-129
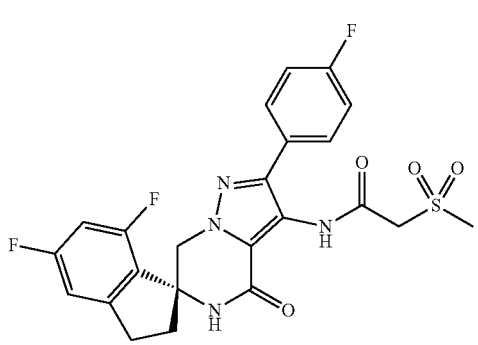
I-151
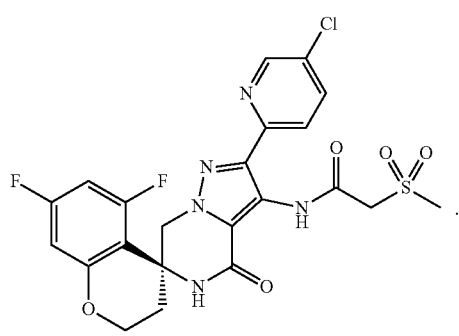
.
I-131
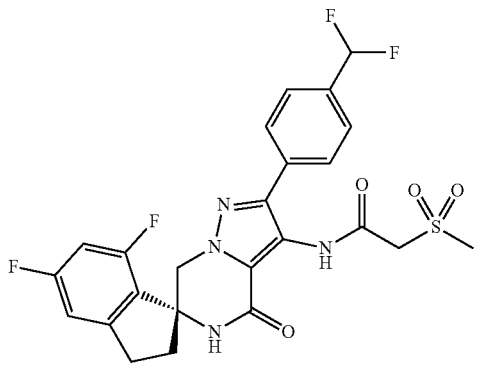
22. The compound or its pharmaceutically acceptable salt according to claim 1, wherein the compound is selected from the group consisting of:

I-138

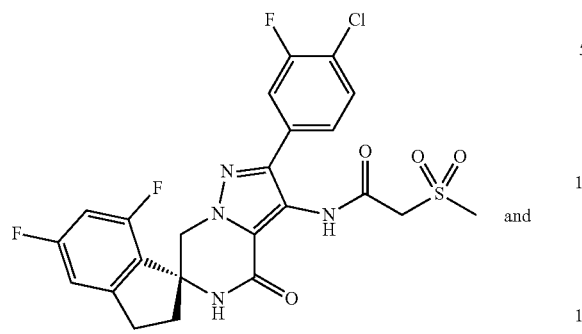

and

I-139

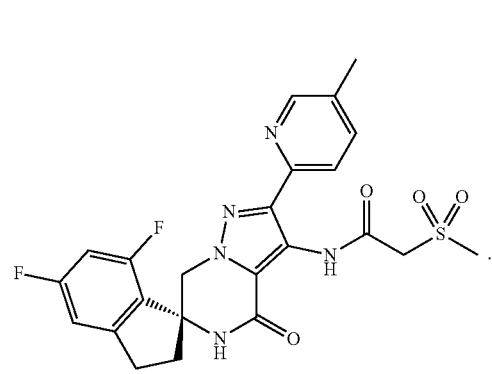

23. The compound or its pharmaceutically acceptable salt according to claim 1, wherein the compound is:

I-141

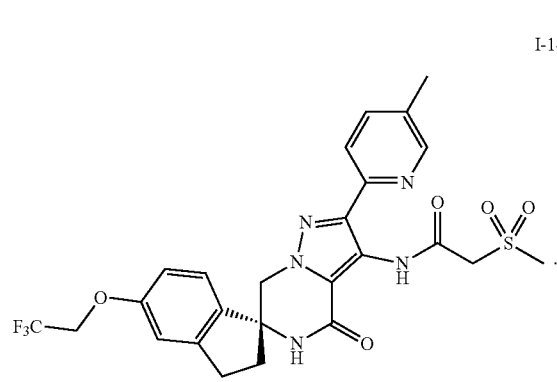

24. The compound or its pharmaceutically acceptable salt according to claim 1, wherein the compound is:

I-033

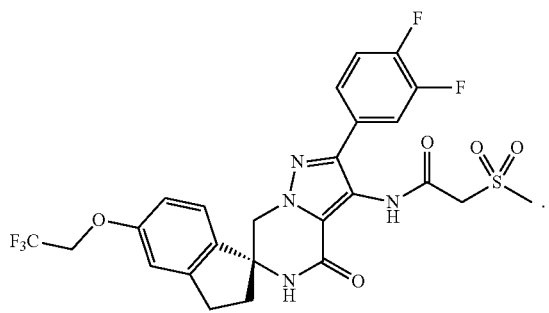

25. The compound or its pharmaceutically acceptable salt according to claim 1, wherein the compound is:

I-079

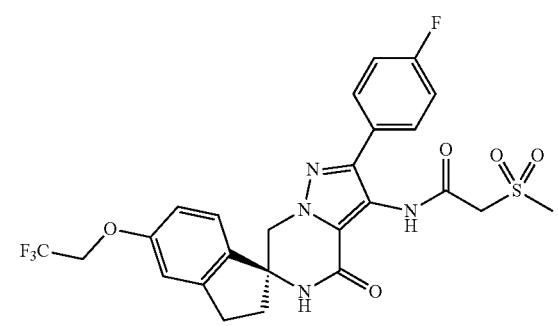

26. The compound or its pharmaceutically acceptable salt according to claim 1, wherein the compound is:

I-141

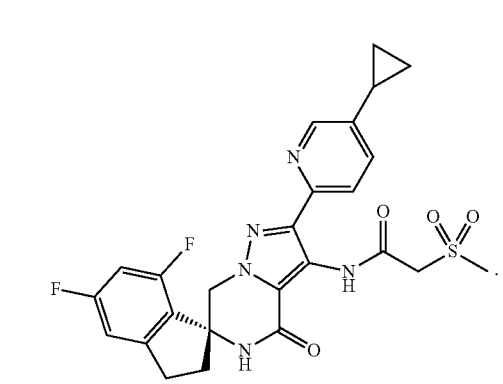

27. The compound or its pharmaceutically acceptable salt according to claim 1, wherein the compound is:

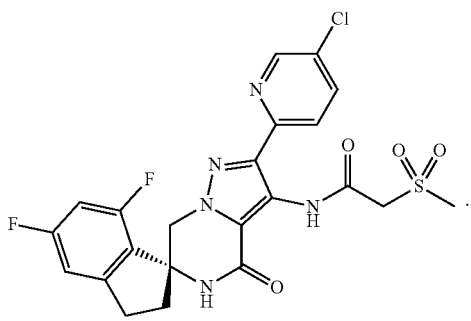
I-142
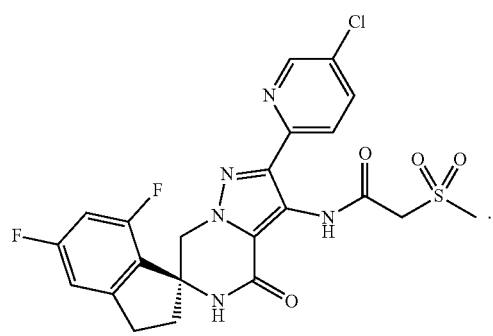
I-147
28. The compound or its pharmaceutically acceptable salt according to claim 1, wherein the compound is:
* * * * *

UNITED STATES PATENT AND TRADEMARK OFFICE
CERTIFICATE OF CORRECTION

PATENT NO. : 12,227,509 B2
APPLICATION NO. : 17/422108
DATED : February 18, 2025
INVENTOR(S) : Yusuke Tateno et al.

Page 1 of 3

It is certified that error appears in the above-identified patent and that said Letters Patent is hereby corrected as shown below:

In the Claims

Claim 6, Column 156, Lines 53-66:

" 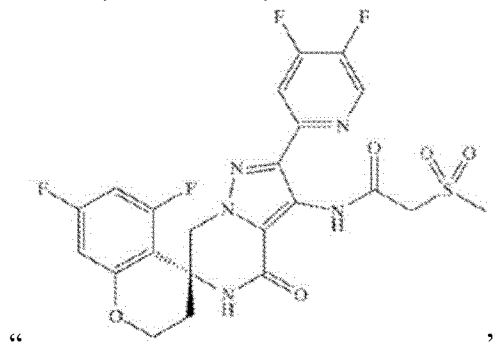 " should be deleted, and

-- 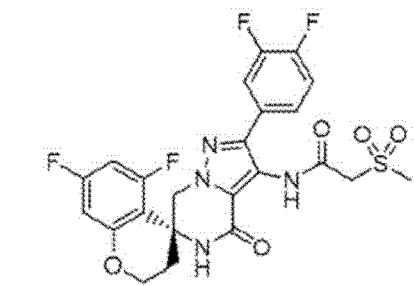 -- should be added.

Claim 6, Column 157, Lines 1-13:

Signed and Sealed this
Fifteenth Day of April, 2025

Coke Morgan Stewart
*Acting Director of the United States Patent and Trademark Office*

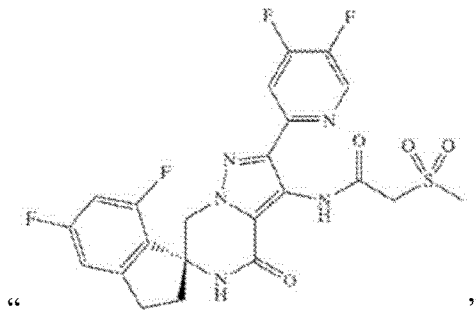 " should be deleted, and
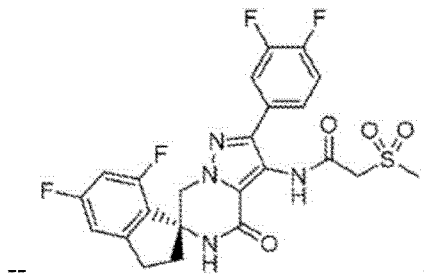 -- should be added.
Claim 6, Column 158, Lines 35-46:
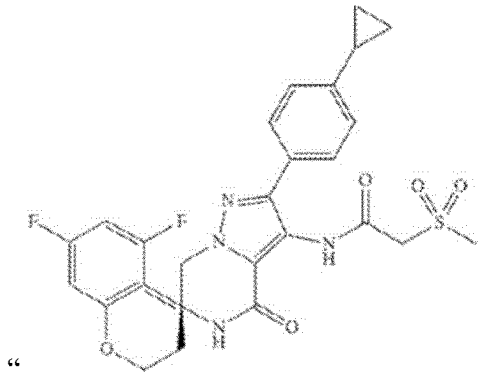 " should be deleted, and
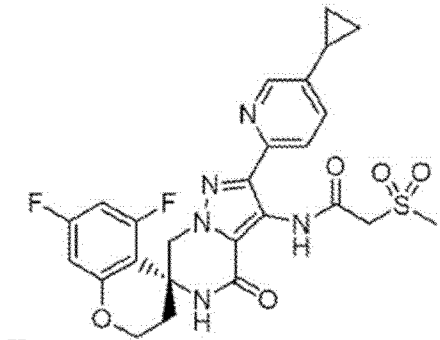 -- should be added.
Claim 6, Column 159, Lines 37-52:

CERTIFICATE OF CORRECTION (continued)
U.S. Pat. No. 12,227,509 B2

" 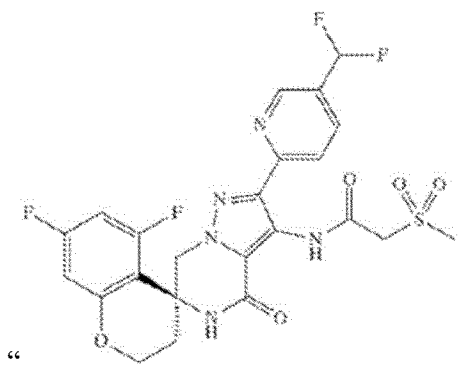 " should be deleted, and

-- 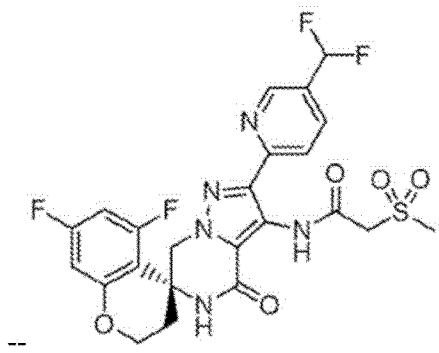 -- should be added.

Claim 23, Column 179, Line 51:
"I-141" should be deleted, and
--I-006-- should be added.